US010959444B2

(12) United States Patent
Poulsen et al.

(10) Patent No.: US 10,959,444 B2
(45) Date of Patent: Mar. 30, 2021

(54) EPS GENE CLUSTER OF TEXTURIZING LACTIC ACID BACTERIA

(71) Applicant: Chr. Hansen A/S, Hoersholm (DK)

(72) Inventors: Vera Kuzina Poulsen, Vaerloese (DK); Gunnar Oeregaard, Vaerloese (DK); Patrick Derkx, Tikoeb (DK)

(73) Assignee: CHR. HANSEN A/S, Hoersholm (DK)

( * ) Notice: Subject to any disclaimer, the term of this patent is extended or adjusted under 35 U.S.C. 154(b) by 161 days.

(21) Appl. No.: 16/062,057

(22) PCT Filed: Dec. 19, 2016

(86) PCT No.: PCT/EP2016/081724
§ 371 (c)(1),
(2) Date: Jun. 13, 2018

(87) PCT Pub. No.: WO2017/108679
PCT Pub. Date: Jun. 29, 2017

(65) Prior Publication Data
US 2019/0021354 A1 Jan. 24, 2019

(30) Foreign Application Priority Data

Dec. 22, 2015 (EP) .................................. 15201995
May 18, 2016 (EP) .................................. 16170128

(51) Int. Cl.
*A23C 9/123* (2006.01)
*C12R 1/46* (2006.01)
*C07K 14/195* (2006.01)
*C12N 9/10* (2006.01)
*C12N 9/14* (2006.01)
*C12N 1/20* (2006.01)

(52) U.S. Cl.
CPC .......... *A23C 9/1238* (2013.01); *C07K 14/195* (2013.01); *C12N 9/1048* (2013.01); *C12N 9/14* (2013.01); *C12R 1/46* (2013.01); *A23Y 2240/41* (2013.01); *C12N 1/20* (2013.01)

(58) Field of Classification Search
None
See application file for complete search history.

(56) References Cited

FOREIGN PATENT DOCUMENTS

CN 101331900 12/2008
EP 0 750 043 A1 12/1996

OTHER PUBLICATIONS

EP0750043. Stingele, Francesca. 1996. Machine translation. p. 1-22.*
Bentley et al., "Genetic Analysis of the Capsular Biosynthetic Locus from All 90 Pneumococcal Serotypes," PLoS Genetics (Mar. 2006) vol. 2, No. 3, e31, pp. 0262-0269.
Dabour et al. "Identification and Molecular Characterization of the Chromosomal Exopolysaccharide Biosynthesis Gene Cluster from *Lactococcus lactis* subsp. *cremoris* SMQ-461," Applied Environmental Microbiology, (Nov. 2005), vol. 71, No. 11, pp. 7414-7425.
Forde et al., "Molecular organization of exopolysaccharide (EPS) encoding genes on the lactococcal bacteriophage adsorption blocking plasmid, pCI658," Plasmid (2003) vol. 49, pp. 130-142.
Goujon et al., "A new bioinformatics analysis tools framework at EMBL-EBI," Nucleic Acids Research (2010) vol. 38, pp. W695-W699.
Groot et al., "Mutational analysis of the Lactococcus lactis NIZO B40 exopolysaccharide (EPS) gene cluster: EPS biosynthesis correlates with unphosphorylated EpsB," Journal of Applied Microbiology (2007) vol. 103, pp. 2645-2656.
Larkin et al., "Clustal W and Clustal X version 2.0," Bioinformatics (2007) vol. 23, No. 21, pp. 2947-2948.
Pan et al, "Antioxidant activity of an exopolysaccharide purified from *Lactococcus lactis* subsp. *lactis* 12," Carbohydrate Polymers, vol. 80 (Jan. 2010) pp. 908-914.
Schmid et al., "Bacterial exopolysaccharides: biosynthesis pathways and engineering strategies," Frontiers Microbiology, vol. 6 (May 2016) No. 496, pp. 1-24.
Susuki et al., "Novel Exopolysaccharides Produced by *Lacococcus lactis* subsp. *lactis*, and the Diversity of epsE Genes in the Exopolysaccharide Biosynthesis Gene Clusters," Bioscience, Biotechnology and Biochemistry, (Oct. 2013) vol. 77, No. 10, pp. 2013-2018.
Van Kranenburg et al., "Functional Analysis of Glycosyltransferase Genes from Lactococcus lactis and Other Gram-Positive Cocci: Complementation, Expression, and Diversity," Journal of Bacteriology (Jun. 1999) vol. 181, pp. 6347-6353.
Whittall et al., "Topology of *Streptococcus pneumoniae* CpsC, a Polysaccharide co-polymerase and BY-kinase adaptor protein," J. Bacteriol. (Published online Oct. 2014) 197: 120, pp. 1-33.
Boels et al., "Increased Exopolysaccharide Production in Lactococcus lactis due to Increased Levels of Expression of the NIZO B40 eps Gene Cluster," Applied and Environmental Microbiology, (Aug. 2003) vol. 69, No. 8, pp. 5029-5031.
Germond et al., "Heterologous expression and characterization of the exopolysaccaride rom *Streptococcus thermophiles* Sfi39," European Journal of Biochemistry, (2001) Vo. 268, pp. 5149-5156.
Kleerebezem et al., "Exopolysaccharides produced by Lactococcus lactis: from genetic engineering to improved rheological properties?," Antonie van Leuwenhoek, (1999) vol. 76, pp. 357-365.
Van Kranenburg et al., "Molecular characterization of the plasmid-encoded eps gene cluster essential for exopolysaccharide biosynthesis in Lactococcus lactis,",Molecular microbiology, (1997) vol. 24, No. 2, pp. 387-397.
Welman et al., "Exopolysaccharides from lactic acid bacteria: perspectives and challenges," Trends in Biotechnology (Jun. 2003) vol. 21, No. 6, pp. 269-274.

(Continued)

Primary Examiner — Paul J Holland
(74) Attorney, Agent, or Firm — Foley & Lardner LLP

(57) ABSTRACT

Novel *Lactococcus lactis* subsp. *lactis* lactic acid bacterium strain having improved texturizing properties and method of using the strain for producing a food product.

21 Claims, 8 Drawing Sheets
Specification includes a Sequence Listing.

(56) References Cited

OTHER PUBLICATIONS

XP-002768398, "Polysaccharide biosynthesis export protein," EBI accession No. UNIPROT: A0A0D6DUZ6, (May 2015).
XP-002768399 "Putative glycosyltransferase," EBI accession No. UNIPROT: G8DU95 (Jan. 2012).
XP-002768400 "Glycosyltransferase, family 2," EBI accession No. UNIPROT: A9QSJ9 (Feb. 2008).

* cited by examiner

| *L. lactis* subsp. | Strain | GenBank nr | *eps* cluster localization |
|---|---|---|---|
| cremoris | NIZO B40 | AF036485 | plasmid |
|  | Ropy352 | EF192213 | plasmid |
|  | HO2 | AF142639 | plasmid |
|  | SMQ-461 | AY741550.2 | chromosome |
|  | A76 | CP003132 | chromosome |
| lactis | KLDS 4.0325 | CP006766 | chromosome |
|  | KF147 | CP001834 | chromosome |
|  | YF11 | APAV00000000 |  |
|  | CNCM I-1631 | AGHX00000000 |  |
|  | 1AA59 | AZQT00000000 |  |

FIGURE 3C

| | KF147 | YF11 | Strain A | Strain E | Strain F | H02 | Strain D | CNCM I-1631 | Strain C | CHCC11848 | KLDS 4.0325 | B40 | A76 | SMQ-461 | 1AA59 | Strain B | Ropy 352 |
|---|---|---|---|---|---|---|---|---|---|---|---|---|---|---|---|---|---|
| KF147 | 100 | 99 | 90 | 82 | 72 | 72 | 75 | 69 | 88 | 75 | 73 | 75 | 68 | 74 | 72 | 83 | 65 |
| YF11 | 99 | 100 | 90 | 82 | 72 | 72 | 75 | 69 | 89 | 76 | 73 | 75 | 67 | 74 | 72 | 83 | 65 |
| Strain A | 90 | 90 | 100 | 93 | 88 | 88 | 89 | 87 | 95 | 88 | 87 | 90 | 83 | 89 | 87 | 91 | 78 |
| Strain E | 82 | 82 | 93 | 100 | 67 | 67 | 71 | 65 | 89 | 75 | 70 | 72 | 61 | 71 | 69 | 82 | 60 |
| Strain F | 72 | 72 | 88 | 67 | 100 | 94 | 80 | 65 | 89 | 70 | 66 | 70 | 58 | 70 | 67 | 81 | 57 |
| H02 | 72 | 72 | 88 | 67 | 94 | 100 | 78 | 66 | 90 | 70 | 66 | 71 | 58 | 70 | 67 | 81 | 58 |
| Strain D | 75 | 75 | 89 | 71 | 80 | 78 | 100 | 68 | 90 | 73 | 70 | 74 | 65 | 73 | 72 | 82 | 62 |
| CNCM I-1631 | 69 | 69 | 87 | 65 | 65 | 66 | 68 | 100 | 95 | 72 | 71 | 71 | 61 | 68 | 66 | 80 | 59 |
| Strain C | 88 | 89 | 95 | 89 | 89 | 90 | 90 | 95 | 100 | 91 | 90 | 91 | 85 | 90 | 89 | 91 | 80 |
| CHCC11848 | 75 | 76 | 88 | 75 | 70 | 70 | 73 | 72 | 91 | 100 | 83 | 76 | 67 | 74 | 72 | 83 | 64 |
| KLDS 4.0325 | 73 | 73 | 87 | 70 | 66 | 66 | 70 | 71 | 90 | 83 | 100 | 72 | 63 | 71 | 68 | 82 | 61 |
| B40 | 75 | 75 | 90 | 72 | 70 | 71 | 74 | 71 | 91 | 76 | 72 | 100 | 85 | 74 | 72 | 82 | 64 |
| A76 | 68 | 67 | 83 | 61 | 58 | 58 | 65 | 61 | 85 | 67 | 63 | 85 | 100 | 65 | 62 | 79 | 53 |
| SMQ-461 | 74 | 74 | 89 | 71 | 70 | 70 | 73 | 68 | 90 | 74 | 71 | 74 | 65 | 100 | 71 | 82 | 63 |
| 1AA59 | 72 | 72 | 87 | 69 | 67 | 67 | 72 | 66 | 89 | 72 | 68 | 72 | 62 | 71 | 100 | 81 | 62 |
| Strain B | 83 | 83 | 91 | 82 | 81 | 81 | 82 | 80 | 91 | 83 | 82 | 82 | 79 | 82 | 81 | 100 | 71 |
| Ropy 352 | 65 | 65 | 78 | 60 | 57 | 58 | 62 | 59 | 80 | 64 | 61 | 64 | 53 | 63 | 62 | 71 | 100 |

*L. lactis lactis* CHCC11848

FIGURE 5 (Continued)

| Gene/ORF | Length, aa | Organism | Accession nr. | Identity, % | Analysis tool | Proposed function and predicted protein domains |
|---|---|---|---|---|---|---|
| epsR | 106 | L. lactis | WP_032944811 | 100 | blastp refseq | XRE family transcriptional regulator |
| | | | IPR010982 | | InterPro | DNA binding |
| epsX | 256 | L. garvieae | WP_040087880 | 98 | blastp refseq | polysaccharide biosynthesis protein |
| | | L. lactis | AAX19699 | 97 | blastp refseq | epsX |
| | | | IPR013830 | | InterPro | SGNH hydrolase-type esterase |
| | | | PF13472 | | Pfam | Lipase_GDSL_2 domain |
| epsA | 260 | L. lactis | AAX19700 | 99 | blastp refseq | epsA |
| | | | IPR003856 | | InterPro | Chain length determinant (Wzz) |
| | | | PF13807 | | Pfam | GNVR (G-rich domain on putative tyrosine kinase) |
| epsB | 232 | L. lactis | WP_017863989 | 98 | blastp refseq | tyrosine protein kinase epsB |
| | | | IPR005702 | | InterPro | tyrosine-protein kinase involved in EPS synthesis |
| epsC | 255 | L. lactis | WP_039114425 | 98 | blastp refseq | tyrosine protein phosphatase |
| | | L. lactis | WP_032490719 | 98 | blastp refseq | epsC |
| | | | IPR016667 | | InterPro | Capsular polysaccharide synthesis, CpsB/CapC |
| epsD | 229 | L. lactis | WP_039114427 | 93 | blastp refseq | sugar transferase |
| | | L. lactis | WP_032490720 | 92 | blastp refseq | epsD |
| | | | IPR003362 | | InterPro | sugar transferase |
| GT1 | 374 | S. thermophilus | AAM93395 | 47 | blastp refseq | cpsF |
| | | L. lactis | ABX75683 | 48 | blastp refseq | GT group 1 |
| | | | IPR028098, IPR001296 | | InterPro | GT subfamily 4 and GT family 1 |

FIGURE 5 (Continued)

| Gene/ORF | Length, aa | Organism | Accession nr. | Identity, % | Analysis tool | Proposed function, predicted protein domains |
|---|---|---|---|---|---|---|
| wzy | 368 | L. lactis | WP_023163591 | 36 | blastp refseq | hypothetical protein |
| | | L. lactis | ABX75684 | 34 | blastp refseq | polysaccharide biosynthesis protein |
| | | S. thermophilus | WP_011227239 | 33 | blastp refseq | EPS polymerization protein |
| | | | PF14897 | | Pfam | transmembrane Wzy-like protein |
| GT2 | 292 | Ruminococcaceae | WP_037279636 | 44 | blastp refseq | WcaA-like protein, colanic acid biosynthesis GT |
| | | Clostridium | WP_023973425 | 40 | blastp refseq | MULTISPECIES: GT family 2 |
| | | S. pneumoniae | CGG06699 | 34 | blastp S. pneumoniae | GT family 2 |
| | | | IPR029044 | | InterPro | nucleotide-diphospho-sugar transferase |
| | | | IPR001173 | | InterPro | GT family 2 |
| GT3 | 299 | L. lactis | WP_012896995 | 51 | blastp refseq | GT family 2 |
| | | S. pneumoniae | CAI33891 | 34 | blastp S. pneumoniae | putative GT |
| | | | IPR029044 | | InterPro | nucleotide-diphospho-sugar transferase |
| | | | IPR001173 | | InterPro | GT family 2 |
| wzx | 474 | L. piscium | CEN27320 | 73 | blastp refseq | polysaccharide biosynthesis export |
| | | L. lactis | WP_023163597 | 69 | blastp refseq | MATE-type (membrane export) protein |
| | | S. pneumoniae | CAI32995 | 39 | blastp S. pneumoniae | flippase Wzx, MATE-type membrane export |
| | | | IPR002797 | | InterPro | Polysaccharide biosynthesis |
| ugd | 389 | L. lactis | WP_043736727 | 96 | blastp refseq | UDP-glucose 6-dehydrogenase |
| | | | PF03721, PF00984, PF03720 | | Pfam | UDP-glucose/GDP-mannose dehydrogenase |
| epsL | 301 | L. garvieae | WP_040087865 | 99 | blastp refseq | EPS biosynthesis protein |
| | | L. lactis | AAX19712 | 94 | blastp refseq | epsL |
| | | | IPR014565 | | InterPro | EPS biosynthesis, EpsL, firmicutes |
| | | | IPR018711 | | InterPro | Periplasmic protein (DUF2233) |
| orfY | 301 | L. lactis | WP_046124629 | 99 | blastp refseq | LytR family transcriptional regulator |
| | | | IPR004474 | | InterPro | Transcriptional attenuator |

SEQUENCE LISTING

```
<160> NUMBER OF SEQ ID NOS: 30

<210> SEQ ID NO 1
<211> LENGTH: 13097
<212> TYPE: DNA
<213> ORGANISM: Lactococcus lactis subsp. lactis
<220> FEATURE:
<223> OTHER INFORMATION: Full EPS operon sequence

<400> SEQUENCE: 1
atgaatgatt tgtttacca tcgtctaaag gaactagttg aatcaagtgg taaatctgca      60
aatcaaatag agagggaatt gggttaccct agaaattctt tgaataatta taagttagga    120
ggagaaccct ctgggacaag attaatagga ctatcggagt attttagtgt gtctccaaaa    180
tatctgatgg gtataattga tgagcctaat gatagttctg caattaatct ttttaaaagt    240
ctaactcaag aagagaaaaa agaaatgtgt ataatttgtc aaaaatggct tttttagaa     300 tatcaaatag aattataaca ataataaatt tagggagttt ttcttattac tatgatgaaa    360
aaaggaattt ttgtaattac tatagtgata tctatagcat tgataattgg aggttttat    420 agttataatt ctaggataaa taatctttca aaaactaata acggaaaaga agttgtaaaa    480
aatagcagtg aaaaaaatca gatagaactt acctataaaa agtattataa aaatttacca    540
aaatcagttc aaaataaaat agatgatatt tcatccaaaa ataaagaagt tactttaact    600
tgtatttggc aatctgattc agttatttct gaacaatttc aacaaaactt acaaaaatat    660
tatggaaata agttttggaa catcaaaaat atcacttaca atggcgaaac tagtgaacaa    720
ttattggctg aaaaagttga aaatcaagta ttagccacta atcctgatgt tgttttatat    780
gaagctccac tttttaatga taaccaaaac attgaagcaa cagcctcact gactagtaat    840
gagcaactta taacaaattt ggctagtgca ggagcggagg taatagttca accctctcca    900
ccgatctatg tggtgttgt gtaccccgta caagaagaac aatttaaaca atctttatct    960
acaaagtatc cctatataga ctactgggct agttaccag acaaaaattc tgatgaaatg   1020 aagggggctgt tttctgataa tggagtatat agaacattaa atgcttcggg gaataaggtt  1080
tggctagatt atattactaa atattttaca gcaaactaat taagttataa ataacaatta   1140
ttaaatattg gagaagaaat gcaggaaaca caggaacaaa cgattgattt aagagggatt   1200
tttaaaatta ttcgcaaaag gttaggttta atattattta gtgctttaat agtcacaata   1260
ttagggagca tctacacatt ttttatagcc tccccagttt acacagcctc aactcaactt   1320
gtcgttaaac taccaaattc ggataattca gcagcctacg ctgacaagt gaccgggaat   1380 attcaaatgg cgaacacaat taaccaagtt attgttagtc cagtcatttt agataaagtt   1440
```

```
caaagtaatt taaatctatc tgatgactct ttccaaaaac aagttacagc agcaaatcaa    1500
acaaattcac aagtcattac gcttactgtt aaatattcta atccttacgt tgctcaaaag    1560
attgcagacg agactgctaa aatatttagt tcagacgcag cgaaactatt gaatgttact    1620
aacgttaata ttctatccaa agcaaaagct caaacaacac ccattagtcc taaacctaaa    1680
ttgtatttag caatatctgt tatagccgga ttagttttag gtttagccat tgctttattg    1740
aaggaattgt ttgataacaa aattaataaa gaagaagata ttgaagctct gggactcacg    1800
gttcttggtg taacaaccta tgctcaaatg agtgatttta ataagaatac gaataaaaat    1860
ggcacgcaat cgggaactaa gtcaagtccg cctagcgacc atgaagtaaa tagatcatca    1920
aaaaggaata aaagatagga gttcaggatg gctaaaaata aagaagcat agacaacaat     1980 cgttatatta ttaccagtgt caatcctcaa tcacctattt ccgaacaata tcgtacgatt    2040
cgtacgacca ttgattttaa aatggcggat caagggatta aaagtttct agtaacatct     2100 tcagaagcag ctgcaggtaa atcaaccgta agtgctaatc tagctgttgc ttttgcacaa    2160
caaggtaaaa aagtactttt aattgatggc gatcttcgta aaccgactgt taacattact    2220
tttaaagtac aaaatagagt aggattaacc aatattttaa tgcatcaatc ttcgattgaa    2280
gatgccatac aagggacaag actttctgaa atcttacaa taattaccctc tggtccaatt    2340 ccacctaatc catcggaatt attagcatct agtgcaatga agaatttgat tgactctgtg    2400
tccgattcct ttgatattgt tttgattgat actccacctc tctctgcagt tactgatgct    2460
caaattttga gtatttatgt aggaggagtg gttcttgttg tacgtgccta tgaaacaaaa    2520
aaagagagtt tagcaaaaac aaaaaaaata ctggaacaag ttaatgtaaa tatattagga    2580
gttgttttgc atgggtaga ctcttctgag tcaccgtcgt attactacta cggagtagag    2640
taattggaat aaattttaat caaataaaag acagaaattt gtagaagagg ggagcaaatg    2700
attgatattc attgccatat tttaccgggg atagatgatg gagctaaaac ttctggtgat    2760
actctgacaa tgctgaaatc agcaattgat gaagggataa cagctatcac tgcaactcct    2820
catcataatc ctcaatttaa taatgaatca ccgcttattt tgaaaaaagt taaggaagtt    2880
caaaatatca ttgacgaaca tcaattacca attgaagttt tacccggaca agaggtgaga    2940
atatatggtg atttattaaa agaattttct gaagggaagt tactgacagc agcgggcact    3000
tcaagttata tactgattga atttccatca aatcatgtgc cagcttatgc taaagaactt    3060
ttttataata ttcaattgga gggacttcaa cctatttggg ttcaccctga gcgtaatagt    3120
gcaatcattg agaaccctga tatattattt gattttattg aacaaggagt actaagtcag    3180
ataacagctt caagtgtcac tggtcatttt ggtaaaaaaa tacaaaagct gtcatttaaa    3240
atgatagaaa accatctgac gcattttgtt gcatcagatg cgcataatgt gacgtcacgt    3300
gcatttaaga tgaaggaagc atttgaaatg attgaagata gttatggttc tggtgtatca    3360
cgaaggttta agataatgc agagtcagtg atttaaaacg aaagttttta tcaagaaaaa     3420
ccaacaaaga tcaaaacaaa aaaattttta ggattatttt aaagggatta aaaggagtaa    3480
ataatggaag ttttttgagga tgcctcatca cctgaatcgg aagaacacaa attagtagta    3540
ttaaaaaatt tttcttatgg agagctgatt ataaaaagag caattgatat cctaggagga    3600
ttagcgggtt cagttttatt tcttatcgcg gctgcattgc tttatgtccc ttacaaaatg    3660
agctcggaaa aagatcaagg gccaatgttc tataaacaaa aacgggttgg aaaaaacggt    3720
aaaatttttt atattttgaa atttagaaca atgataatta atgctgagca gtatctagag    3780
```

```
ctacatccag aagttaaagc cgcctatcat gccaatggta ataaactaga aaatgatccc    3840
cgtgtgacga agattggttc atttattaga caatactcag ttgatgaatt accacaattt    3900
atcaatgtcc ttaaaggaga tatggcatta gtcggtccaa ggccaattca acattttgaa    3960
gcgaaagaat tgggggagcg cctcccttat ttactgatat gtaaacctgg aattactggt    4020
tattggacaa cacatggtcg cagtaaagct ccttttcctc aacgagcaga tttagaactc    4080
tattatctcc aatatcacag caccaagaat gatgtcaagc ttcttatgct tacaattgca    4140
caaattattc acggatcgga cgcatattaa aaacaatga aaaaaagaa attattacta     4200
ataagtcaaa gcggaagagg tggagtaagg aaacatcttt gtgatttact tacttctctt    4260
gattataaaa aatttgagat ttggattgcc tataatgatg atgaggtcga tgagattttt    4320
aaatatacgt tggaaagttt aaggggaaaa gttaaaccaa tcattataaa agaaatggtt    4380
agagaactta atcctaaaca agattggatt gcatttaaga aaattcgtag gtcaataaaa    4440
gagataaaac cagatattgt tcattgccat agttcgaaag cgggaatatt agggcgagca    4500
gctgcaaaaa tagtgggtat aaaacaaata tattacacac ctcacgctta ctcttttctc    4560
gctacagaat tttcagtaaa aaagaaaaga ttattcatta atctagaacg ttttttagt     4620
cattatgcta caactttaac atttaccgta tcagaaggtg aaaagaagc agcactaaaa     4680
aacaaagttg atagcaatga gaaatttaaa gtaatttata atggattgaa agatataaaa    4740
atcttatcta aaatagaagc cagggaaaaa cttggattac cacaagataa atttattttt    4800
ggtaatattg ctcgaatttg tgaacaaaaa aatccaattt attttataga agttgctcaa    4860
aaaaatcctg attattattt tgtttggatt ggtgatggtg aacttcgtga gaaagtcaaa    4920
caagaaattc tctatagaaa cctgaaaaat atttgtttct taggaaatag aaatgatgca    4980
ggaataatgg tcgcggcatt cgatgtgttt atatctactt ctaaatatga aggactgccc    5040
tattcaccta ttgaagctct ccgagctgga gtgcctgttt tgttaagtga tgttgttggt    5100
aataatgaag ttgtcttaag ccatagaaat ggggaagttt ttgatttaaa ttcgtctaat    5160
tggaataaaa gacttgatga atttagaaag tggcaaaaga agaaaacgag tatagagatc    5220
agacaaacgt ttcttaatca cttctcattg gataaatcga taaagaaact aactaagata    5280
tatttgaata atgagtaata ggcaacagtt acatagctat tttcatccaa caagtgattc    5340
tatggctttc ctatgatcaa caaatttagt agttatgttt tattgtagcc taatattcca    5400
aaacaattta aaacattaaa attcaagtaa ctttttagtt aattaaattc ggataggctt    5460
aataaaattg tggattaaat taacttatat gcagattcta ctgagattag gtcatgatc    5520
gcttgtatta attatttcac acataaccag gagtaagatt tatgcttatt tattttcttt    5580
tatttcctat aattatttta ttatatattt ttacaaacaa cggactatta aagagtaaaa    5640
aaatatttat aggactttca ttctccatac tagggattat ttcgtctata cgttctcctc    5700
aagtaggaac cgatacatca acttaccaaa cactttcctt ctatcaaata catgggaataa   5760
aaatattcaa ttcaaacaat ccggagttaa gcagcaaagc tccactttat ggtgtatata    5820
gtcgtattgt aagtatgatt tcagtaaatt tacagaccat tactatagct aattcattgc    5880
tgatagcatt cttatttgga attttttattt atagattgaa aattaatccg ctatattcaa    5940
ctttattatt tattagtatt ggattttttca caagttctct taatacatct cgacagttta   6000
tcgctatcgg tttagtatgc aatgctctgc tatttctatt tgataaaaag gcatttatat    6060
attttgcttt aatcacatta gcaatatcta ttcatcgct agcaatagtt ggattgatat     6120
tttatccgat ttataagatt aaatggacag cagtaaaaat atcctgtttt ctaattgtgt    6180
```

```
tgacaatgac aagcttttc  cttgagtctg tttcgaaaat ttttattcaa tttttcccca   6240
attacgcttt ttacttacaa aatcccgtga cattctttgg tgcttctagc cgtataataa   6300
tgattttaga tattggacta attttaatta ttttattatt ttatgcgttg actaaatact   6360
atcatattaa gtgtagtcaa gaagaagttt ctttgcttat cattttctta attggaccat   6420
tttttgaaat acttgtattt cacaatcaga gtatattact tttgactcaa cgatttctaa   6480
cttttttttc tattttaagt attgctgtaa ttccaggaat gtgtgctaaa gtttcaaaaa   6540
aattcaataa cccagaaaat gtgagttttg cttttttag  tgttatattt attttcacat   6600
tatttacttt ttctgtagaa attcaaaaat attggggagt tattccctat attacttta   6660
tgtaattaga aaggtttatt taaatatgct aatttctgta ataattccaa tgtataatag   6720
aaaatttaca ataagagag  ctatgaacag tgtactttct caagtaccaa ataaaaagga   6780
gtttcaaatt gaattaattg ttgttgatga ctgctccact gacaatagtg ttgaggttgc   6840
tagagaaata aaggatgaac gggtaaaaat tgtcaaactt gataaaaact cgggtgctaa   6900
tgttgcgaga aattatggaa ttaatttagc aaatggtgag ataatcgctt ttaatgattc   6960
agatgatgaa tggcttcctg aaaaactttc taagcaactt gaagtacttc aagaaaaaaa   7020
tatagatttt ttgtgctgta atatggaaac ggatgtttac agtggaaaaa tgaaaatgct   7080
tacgcctaga ccgtcaggtt ttgttccaat tgaagaattg cttggaaaaa attatatagt   7140
aagtactcag aatttgattg gaaaagctga tatgtttaaa tctaatcaat tcagtcatga   7200
aatctctcgt tttcaagact gggagcttat tctacggctt ttgattaagg ggtataggct   7260
ttattttatg gaagaagtat tagtgagaca gtatattcaa ccaaatagtt tatccaaaaa   7320
tttaaaaaat ggtgttttgt ctctccgata tatgcttgag gaattcaaag aagagtatgc   7380
acagcatcct ttacaaaagg cagaggtaat attaactgtt ggtagccatt tacacaatat   7440
gaattatcga tgtgctcaat tttatttaa  atctttgaag ttaagattta gcatgactgt   7500
attggcaaaa gcacttttta tgttttttac ggacttatca agaaagaagg aaagcgaatg   7560
acagagagga ttacagtgat tctttccgca tataacggtg agaaatatat tcaaagtcaa   7620
atagacagta tacttaatca aacatatgat aattttattt tatatattag agatgatgga   7680
tcaactgacg gaactcgaaa aattctgaag caatattctg aaaaagattc acgagtgaaa   7740
gttcaatatg gtgaaaacat aggctatgta aaaagtttt  ttaaaatgct ttctgaagtc   7800
aattcggaat atatagcatt ttctgatcaa gatgatattt ggctgcctga aaagttatca   7860
gtcgctcaag cagctttatc acagaaaaat aagagcgttc ctctcatgtg ggcctcaaat   7920
atatatatat gtgatgaaaa aatgaatgta atttcgattg gtgcaaggaa gagaatgagt   7980
aatttctcaa attctctttt tatgtgtaat actcaaggaa tgacaatgat aattaataat   8040
aaagctagag aaaaggttgt ttctaatcta ccaaaacaaa atatcatgta ccacgattgg   8100
tggatttatc gcgttgttag tgctttcgga gaagttatat ttgattcaga tccatatgta   8160
aagtatagaa gacatgataa aaatgaatct gatatttcat ataattttgt gaataaagtc   8220
actaatatga tgaaccgctt aataaatagc gatatgtata tacgtacgaa gaaagagaca   8280
caagaattta aaataatttt tgattcacaa cttcacaat  caaatagaga tgtattaagt   8340
ttatttgcct caccaaaaag aaaaattcaa aaagtcttct actcaggtag attcaaaaat   8400
tccgtattag atgaactagt acttcgctta ttttttcttt tagacatttt ataattaaaa   8460
aattttttaa tagttataca ttataagata agttgtttgt atagtacttt aatggtatta   8520
```

```
aattatagag gtaagctatt agacgagaat ttttttattt tacaacttgg aaaacagact    8580
ctaacaaggg gaaatgagaa ataaatgaat aataaattaa gagaaggttt tactttttaca   8640 gcaattggta catatagtaa ttttttaatt caaattattg tacaagcaat tttaagtcga    8700
ttattatcgc caagagagta tggaataatt gctatcatgc aagttttat agttttttt     8760 gcaatgctgg tggaagcagg aatgggacct gctatcatac aaaataaaaa gttaacaaac    8820
agagacaata tgaatttatt taacttttca gctattttt ctattatatt tgcgattata    8880
tttggttttt taggattatt acttacaaag atatatatga atccagcata cacttactta   8940
acttggattc agtctatttc aatattattt attgggttaa atattgttcc gactgcactc   9000
cttaataaaa gaaaacaatt caaagctgta aattttagta cagtagtagg ggggatacta   9060
tcgggagtag tcggagttac aatggctttc ctgggatttg gtatttattc actaattgca   9120
agtgccatta caacggcatt tgtaagtttt tgcttaaaca ggtattttgc taatatttgg   9180
tttactaaaa attggaataa atcttctttg atttctattt ggactgtttc gcggaatcag   9240
tttggaacaa attttataaa ttattttcg aataattcag acaatatttt agtaggaaaa    9300
tttatgggag atacagcact agctaattac aataagtctt atcaactgtt aacaatccct   9360
accactttat tgttgaatat agttaatcca gttttacaac caattctctc agattatcaa   9420
gatgatgttg taactataag aaaaacatac tataatattg ttcacttatt ggctctcatc   9480
gggattccta catcaatttt tcttagtatg tctgcaaaac aaattatttt tttcttttt    9540 ggaagtcagt gggaagaagc agtagttccc ttctcttact tagcagttat tgtatggtgt   9600
caaatgacaa catattcaaa tggagcaatc tggcagtcca gaaataaaac aaattatttt   9660
cttttttcaa gtgttatcaa tacttttatt ataattttt ctatcataat aggtatcata   9720
ataggaaata taaatgcggt tgctttattt gttgcaatag gaaattttat aagttttttt   9780
tggaaattct actatattac taaaaatgca ttagaagatt ctataagaaa tctactaaag   9840
attttcatcc atcctattt tttaggattc atcacattta ttgggattag attagagatt   9900
ttaattgatc ctagaaataa ttttttttagt ctacttctaa gaagcttagt attttttttct 9960 attctaatta cctatattat gtttacatct gaaaagaaaa taattgaaga attttttgat  10020
aaatagtcaa tgcatctata agatactaaa ggattccaaa aatatataag gagaaaaaca  10080
tgaaaatagc agttgttggg acaggctatg tcggttttgtc tatttcagtg cttctagcac  10140
aacatcatga agttgttgct ttggatattg ttgaggcgaa agtagatttg attaactcta  10200
aaaaatcgcc tattgttgat aaggagattg agggattttt agcaagtaaa gaattaaatt  10260
tacttgcgac gacggatacg gctcaagcgc taaatagagc tgactttgtg gtcattgcaa  10320
cacctaccaa ttatgatgat gtcaagaatt attttaatac ggattctgta gaagcagtaa  10380
ttgaagaagt ttggaaattt agcccaaatg ctatgattgt tataaaatca actattccag  10440
ttggttttgt ggaaaaaatg cgtgctaaat atgatattga taacattatc ttttctccag  10500
aatttttacg agaaggtcga gcattgtatg acaatcttca tccatctcgc attgttgtgg  10560
gggaacaatc tgagcgtgcc tctcaatttg ctgagctttt aatagaggga gctattgata  10620
aagatatccc agttcttttt acaaacccta ctgaagcaga agcgattaag ctattttcaa  10680
atacatattt agctttacgc gtggcttatt ttaatgaatt agatacttat gctgaagttc  10740
gtggtttaga tacaaaacaa atcattgatg gcgttggatt agatccacga attggaacac  10800
actacaataa tccttcattt ggttatggag ggtattgcct accgaaagat accaaacagc  10860
ttttagctaa ctacgaccaa gttcctgaaa aattaattga ggctgttgtt gaatcaaata  10920
```

```
gtacaagaaa agatcatatt gcagatatga tcattaaacg ttctcctaaa gtggtgggta    10980
tctaccgctt gactatgaag tcaaattctg ataattttag atcaagttca attcaaggaa    11040
ttatgaaacg aattaagggc aagggaattg aagtagttgt ctatgagcca acactaaatg    11100
atactcattt ctacaattct cgggtagttc ataatttgga tgagtttaaa acgatttctg    11160
atgtgattgt ttcaaatcgt tatactaaag aacttgagga tgttaaaact aaagtttata    11220
cgagagattt atttggccgt gactaaacaa caattttgga ggaaaaattg gaacgaaaaa    11280
aaaagaaaaa aagaatatt tgggttataa ttatacctat cttaattttt attacccctta    11340
```

<213> ORGANISM: Lactococcus lactis subsp. lactis

<400> SEQUENCE: 2

```
atgaatgatt tgttttacca tcgtctaaag gaactagttg aatcaagtgg taaatctgca      60
aatcaaatag agagggaatt gggttaccct agaaattctt tgaataatta taagttagga     120
ggagaaccct ctgggacaag attaatagga ctatcggagt attttagtgt gtctccaaaa     180
tatctgatgg gtataattga tgagcctaat gatagttctg caattaatct ttttaaaagt     240
ctaactcaag aagagaaaaa agaaatgtgt ataatttgtc aaaaatggct tttttagaa      300
tatcaaatag aattataa                                                   318
```

<210> SEQ ID NO 3
<211> LENGTH: 768
<212> TYPE: DNA
<213> ORGANISM: Lactococcus lactis subsp. lactis

<400> SEQUENCE: 3

```
atgatgaaaa aaggaatttt tgtaattact atagtgatat ctatagcatt gataattgga      60
ggttttata gttataattc taggataaat aatctttcaa aaactaataa cggaaaagaa     120
gttgtaaaaa atagcagtga aaaaaatcag atagaactta cctataaaaa gtattataaa     180
aatttaccaa atcagttcca aaataaaata gatgatatt catccaaaaa taagaagtt      240
actttaactt gtatttggca atctgattca gttatttctg aacaatttca acaaaactta     300
caaaaatatt atggaaataa gttttggaac atcaaaaata tcacttacaa tggcgaaact     360
agtgaacaat tattggctga aaagttgaa atcaagtat tagccactaa tcctgatgtt     420
gttttatatg aagctccact ttttaatgat aaccaaaaca ttgaagcaac agcctcactg     480
actagtaatg agcaacttat aacaaatttg gctagtgcag gagcggaggt aatagttcaa     540
ccctctccac cgatctatgg tggtgttgtg taccccgtac aagaagaaca atttaaacaa     600
tctttatcta caaagtatcc ctatatagac tactgggcta gttacccaga caaaaattct     660
gatgaaatga aggggctgtt ttctgataat ggagtatata gaacattaaa tgcttcgggg     720
aataaggttt ggctagatta ttattactaaa tattttacag caaactaa                768
```

<210> SEQ ID NO 4
<211> LENGTH: 780
<212> TYPE: DNA
<213> ORGANISM: Lactococcus lactis subsp. lactis

<400> SEQUENCE: 4

```
atgcaggaaa cacaggaaca aacgattgat ttaagaggga ttttaaaat tattcgcaaa       60
aggttaggtt taatattatt tagtgctttta atagtcacaa tattagggag catctacaca    120
ttttttatag cctccccagt ttacacagcc tcaactcaac ttgtcgttaa actaccaaat    180
tcggataatt cagcagccta cgctggacaa gtgaccggga atattcaaat ggcgaacaca    240
attaaccaag ttattgttag tccagtcatt ttagataaag ttcaaagtaa tttaaatcta    300
tctgatgact ctttccaaaa acaagttaca gcagcaaatc aaacaaattc acaagtcatt    360
acgcttactg ttaaatattc taatccttac gttgctcaaa agattgcaga cgagactgct    420
aaaatattta gttcagacgc agcgaaacta ttgaatgtta ctaacgttaa tattctatcc    480
aaagcaaaag ctcaaacaac acccattagt cctaaaccta aattgtattt agcaatatct    540
gttatagccg gattagtttt aggttagcc attgctttat tgaaggaatt gtttgataac    600
aaaattaata aagaagaaga tattgaagct ctgggactca cggttcttgg tgtaacaacc    660
```

```
tatgctcaaa tgagtgattt taataagaat acgaataaaa atggcacgca atcgggaact    720
aagtcaagtc cgcctagcga ccatgaagta aatagatcat caaaaaggaa taaagatag    780
```

<210> SEQ ID NO 5
<211> LENGTH: 696
<212> TYPE: DNA
<213> ORGANISM: Lactococcus lactis subsp. lactis

<400> SEQUENCE: 5

```
atggctaaaa ataaaagaag catagacaac aatcgttata ttattaccag tgtcaatcct     60
caatcaccta tttccgaaca atatcgtacg attcgtacga ccattgattt aaaaatggcg    120
gatcaaggga ttaaaagttt tctagtaaca tcttcagaag cagctgcagg taaatcaacc    180
gtaagtgcta atctagctgt tgcttttgca caacaaggta aaaaagtact tttaattgat    240
ggcgatcttc gtaaaccgac tgttaacatt acttttaaag tacaaaatag agtaggatta    300
accaatattt taatgcatca atcttcgatt gaagatgcca tacaagggac aagactttct    360
gaaaatctta caataattac ctctggtcca attccaccta atccatcgga attattagca    420
tctagtgcaa tgaagaattt gattgactct gtgtccgatt cctttgatat tgtttttgatt    480 gatactccac ctctctctgc agttactgat gctcaaattt tgagtattta tgtaggagga    540
gtggttcttg ttgtacgtgc ctatgaaaca aaaaaagaga gttagcaaa acaaaaaaa    600 atactggaac aagttaatgt aaatatatta ggagttgttt tgcatggggt agactcttct    660
gagtcaccgt cgtattacta ctacggagta gagtaa                             696
```

<210> SEQ ID NO 6
<211> LENGTH: 765
<212> TYPE: DNA
<213> ORGANISM: Lactococcus lactis subsp. lactis

<400> SEQUENCE: 6

```
atgattgata ttcattgcca tattttaccg gggatagatg atggagctaa aacttctggt     60
gatactctga caatgctgaa atcagcaatt gatgaaggga taacagctat cactgcaact    120
cctcatcata atcctcaatt taataatgaa tcaccgctta ttttgaaaaa agttaaggaa    180
gttcaaaata tcattgacga acatcaatta ccaattgaag ttttacccgg acaagaggtg    240
agaatatatg tgattttatt aaaagaattt tctgaaggga agttactgac agcagcgggc    300
acttcaagtt atatactgat gaatttcca tcaaatcatg tgccagctta tgctaaagaa    360
cttttttata atattcaatt ggagggactt caacctattt tggttcaccc tgagcgtaat    420
agtgcaatca ttgagaaccc tgatatatta tttgatttta ttgaacaagg agtactaagt    480
cagataacag cttcaagtgt cactggtcat tttggtaaaa aaatacaaaa gctgtcattt    540
aaaatgatag aaaaccatct gacgcatttt gttgcatcag atgcgcataa tgtgacgtca    600
cgtgcattta agatgaagga agcatttgaa atgattgaag atagttatgg ttctggtgta    660
tcacgaaggt ttaaagataa tgcagagtca gtgattttaa acgaaagttt ttatcaagaa    720
aaaccaacaa agatcaaaac aaaaaaattt ttaggattat tttaa                   765
```

<210> SEQ ID NO 7
<211> LENGTH: 687
<212> TYPE: DNA
<213> ORGANISM: Lactococcus lactis subsp. lactis

<400> SEQUENCE: 7

```
atggaagttt ttgaggatgc ctcatcacct gaatcggaag aacacaaatt agtagtatta    60 aaaaatttt cttatggaga gctgattata aaaagagcaa ttgatatcct aggaggatta   120
gcgggttcag ttttatttct tatcgcggct gcattgcttt atgtccctta caaaatgagc   180
tcggaaaaag atcaagggcc aatgttctat aaacaaaaac gggttggaaa aacggtaaa    240 atttttata ttttgaaatt tagaacaatg ataattaatg ctgagcagta tctagagcta   300
catccagaag ttaaagccgc ctatcatgcc aatggtaata aactagaaaa tgatccccgt   360
gtgacgaaga ttggttcatt tattagacaa tactcagttg atgaattacc acaatttatc   420
aatgtcctta aaggagatat ggcattagtc ggtccaaggc caattcaaca ttttgaagcg   480
aaagaatttg gggagcgcct cccttattta ctgatatgta aacctggaat tactggttat   540
tggacaacac atggtcgcag taaagctcct tttcctcaac gagcagattt agaactctat   600
tatctccaat atcacagcac caagaatgat gtcaagcttc ttatgcttac aattgcacaa   660
attattcacg gatcggacgc atattaa                                       687

<210> SEQ ID NO 8
<211> LENGTH: 1122
<212> TYPE: DNA
<213> ORGANISM: Lactococcus lactis subsp. lactis

<400> SEQUENCE: 8
atgaaaaaaa agaaattatt actaataagt caaagcggaa gaggtggagt aaggaaacat    60
ctttgtgatt tacttacttc tcttgattat aaaaaatttg agatttggat tgcctataat   120
gatgatgagg tcgatgagat ttttaaatat acgttggaaa gtttaagggg aaaagttaaa   180
ccaatcatta taaagaaat ggttagagaa cttaatccta acaagattg gattgcattt    240 aagaaaattc gtaggtcaat aaaagagata aaaccagata ttgttcattg ccatagttcg   300
aaagcgggaa tattagggcg agcagctgca aaaatagtgg gtataaaaca aatatattac   360
acacctcacg cttactcttt tctcgctaca gaattttcag taaaaaagaa aagattattc   420
attaatctag aacgtttttt tagtcattat gctacaactt aacatttac cgtgtcagaa    480 ggtgaaaaag aagcagcact aaaaaacaaa gttgatagca atgagaaatt taaagtaatt   540
tataatggat tgaaagatat aaaaatctta tctaaaatag aagccaggga aaaacttgga   600
ttaccacaag ataaatttat ttttggtaat attgctcgaa tttgtgaaca aaaaaatcca   660
atttatttta tagaagttgc tcaaaaaaat cctgattatt attttgttg gattggtgat    720 ggtgaacttc gtgagaaagt caaacaagaa attctctata gaaacctgaa aaatatttgt   780
ttcttaggaa atagaaatga tgcaggaata atggtcgcgg cattcgatgt gtttatatct   840
acttctaaat atgaaggact gccctattca cctattgaag ctctccgagc tggagtgcct   900
gttttgttaa gtgatgttgt tggtaataat gaagttgtct taagccatag aaatggggaa   960 gttttgatt taaattcgtc taattggaat aaaagacttg atgaattag aaagtggcaa    1020 aagaagaaaa cgagtataga gatcagacaa acgtttctta atcacttctc attggataaa   1080
tcgataaaag aactaactaa gatatatttg aataatgagt aa                     1122

<210> SEQ ID NO 9
<211> LENGTH: 1104
<212> TYPE: DNA
<213> ORGANISM: Lactococcus lactis subsp. lactis

<400> SEQUENCE: 9
atgcttattt attttctttt atttcctata attattttat tatatatttt tacaaacaac    60
```

```
ggactattaa agagtaaaaa aatatttata ggactttcat tctccatact agggattatt      120
tcgtctatac gttctcctca agtaggaacc gatacatcaa cttaccaaac acttttcttc      180
tatcaaatac atggaataaa aatattcaat tcaaacaatc cggagttaag cagcaaagct      240
ccactttatg gtgtatatag tcgtattgta agtatgattt cagtaaattt acagaccatt      300
actatagcta attcattgct gatagcattc ttatttggaa tttttattta tagattgaaa      360
attaatccgc tatattcaac tttattattt attagtattg gattttcac aagttctctt       420 aatacatctc gacagtttat cgctatcggt ttagtatgca atgctctgct atttctattt      480
gataaaaagg catttatata ttttgcttta atcacattag caatatctat tcatacgcta      540
gcaatagttg gattgatatt ttatccgatt tataagatta aatggacagc agtaaaaata      600
tcctgttttc taattgtgtt gacaatgaca agcttttcc ttgagtctgt ttcgaaaatt       660
tttattcaat ttttccccaa ttacgctttt tacttacaaa atcccgtgac attctttggt      720
gcttctagcc gtaataat gattttagat attggactaa ttttaattat tttattattt        780
tatgcgttga ctaaatacta tcatattaag tgtagtcaag aagaagtttc tttgcttatc      840 atttctcttaa ttggaccatt ttttgaaata cttgtatttc acaatcagag tatattactt     900
ttgactcaac gatttctaac ttttttttct attttaagta ttgctgtaat tccaggaatg      960
tgtgctaaag tttcaaaaaa attcaataac ccagaaaatg tgagttttgc tttttttagt     1020
gttatattta ttttcacatt atttactttt tctgtagaaa ttcaaaaata ttggggagtt     1080
attccctata ttacttttat gtaa                                            1104
```

<210> SEQ ID NO 10
<211> LENGTH: 876
<212> TYPE: DNA
<213> ORGANISM: Lactococcus lactis subsp. lactis

<400> SEQUENCE: 10

```
atgctaattt ctgtaataat tccaatgtat aatagaaaat ttacaataaa gagagctatg       60
aacagtgtac tttctcaagt accaaataaa aaggagtttc aaattgaatt aattgttgtt      120
gatgactgct ccactgacaa tagtgttgag gttgctagaa aataaagga tgaacgggta       180 aaaattgtca aacttgataa aaactcgggt gctaatgttg cgagaaatta tggaattaat      240
ttagcaaatg gtgagataat cgcttttaat gattcagatg atgaatggct tcctgaaaaa      300
ctttctaagc aacttgaagt acttcaagaa aaaatatag attttttgtg ctgtaatatg       360
gaaacggatg tttacagtgg aaaaatgaaa atgcttacgc ctagaccgtc aggttttgtt      420
ccaattgaag aattgcttgg aaaaaattat atagtaagta ctcagaattt gattggaaaa      480
gctgatatgt ttaaatctaa tcaattcagt catgaaatct ctcgttttca agactgggag      540
cttattctac ggcttttgat taaggggtat aggctttatt ttatggaaga agtattagtg      600
agacagtata ttcaaccaaa tagttatatcc aaaaattaa aaaatggtgt tttgtctctc     660
cgatatatgc ttgaggaatt caaagaagag tatgcacagc atcctttaca aaaggcagag      720
gtaatattaa ctgttggtag ccatttacac aatatgaatt atcgatgtgc tcaattttat      780
tttaaatctt tgaagttaag atttagcatg actgtattgg caaaagcact ttttatgttt      840
tttacggact tatcaagaaa gaaggaaagc gaatga                               876
```

<210> SEQ ID NO 11
<211> LENGTH: 897
<212> TYPE: DNA

<213> ORGANISM: Lactococcus lactis subsp. lactis

<400> SEQUENCE: 11

```
atgacagaga ggattacagt gattctttcc gcatataacg gtgagaaata tattcaaagt      60
caaatagaca gtatacttaa tcaaacatat gataatttta ttttatatat tagagatgat     120
ggatcaactg acggaactcg aaaaattctg aagcaatatt ctgaaaaaga ttcacgagtg     180
aaagttcaat atggtgaaaa cataggctat gtaaaaagtt ttttttaaaat gctttctgaa    240
gtcaattcgg aatatatagc attttctgat caagatgata tttggctgcc tgaaaagtta    300
tcagtcgctc aagcagcttt atcacagaaa aataagagcg ttcctctcat gtgggcctca    360
aatatatata tatgtgatga aaaaatgaat gtaatttcga ttggtgcaag gaagagaatg    420
agtaatttct caaattctct ttttatgtgt aatactcaag gaatgacaat gataattaat    480
aataaagcta gagaaaaggt tgtttctaat ctaccaaaac aaaatatcat gtaccacgat    540
tggtggattt atcgcgttgt tagtgctttc ggagaagtta tatttgattc agatccatat    600
gtaaagtata aagacatga taaaaatgaa tctgatattt catataatt tgtgaataaa      660
gtcactaata tgatgaaccg cttaataaat agcgatatgt atatacgtac gaagaaagag    720
acacaagaat ttaaaataat ttttgattca caactttcac aatcaaatag agatgtatta    780
agtttatttg cctcaccaaa aagaaaaatt caaaaagtct tctactcagg tagattcaaa    840
aattccgtat tagatgaact agtacttcgc ttatttttttc ttttagacat tttataa      897
```

<210> SEQ ID NO 12
<211> LENGTH: 1422
<212> TYPE: DNA
<213> ORGANISM: Lactococcus lactis subsp. lactis

<400> SEQUENCE: 12

```
atgaataata aattaagaga aggttttact tttacagcaa ttggtacata tagtaatttt      60
ttaattcaaa ttattgtaca agcaatttta agtcgattat tatcgccaag agagtatgga    120
ataattgcta tcatgcaagt ttttatagtt tttttttgcaa tgctggtgga agcaggaatg    180
ggacctgcta tcatacaaaa taaaaagtta acaaacagag acaatatgaa tttatttaac    240
ttttcagcta ttttttctat tatatttgcg attatatttg gttttttagg attattactt    300
acaaagatat atatgaatcc agcatacact tacttaactt ggattcagtc tatttcaata    360
ttatttattg ggttaaatat tgttccgact gcactcctta ataaaagaaa acaattcaaa    420
gctgtaaatt ttagtacagt agtaggggggg atactatcgg gagtagtcgg agttacaatg    480
gctttcctgg gatttggtat ttattcacta attgcaagtg ccattacaac ggcatttgta    540
agttttttgct aaacaggta ttttgctaat atttggttta ctaaaaattg gaataaatct    600
tctttgattt ctatttggac tgtttcgcgg aatcagtttg gaacaaattt tataaattat    660
ttttcgaata attcagacaa tattttagta ggaaaattta tgggagatac agcactagct    720
aattacaata agtcttatca actgttaaca atccctacca ctttattgtt gaatatagtt    780
aatccagttt tacaaccaat tctctcagat tatcaagatg atgttgtaac tataagaaaa    840
acatactata atattgttca cttattggct ctcatcggga ttcctacatc aattttttctt    900
agtatgtctg caaacaaat tatttttttc ttttttggaa gtcagtggga agaagcagta    960
gttcccttct cttacttagc agttattgta tggtgtcaaa tgacaacata ttcaaatgga   1020
gcaatctggc agtccagaaa taaacaaat tattttctttt tttcaagtgt tatcaatact  1080
tttattataa ttttttctat cataataggt atcataatag gaaatataaa tgcggttgct   1140
```

```
ttatttgttg caataggaaa ttttataagt ttttttttgga aattctacta tattactaaa    1200
aatgcattag aagattctat aagaaatcta ctaaagattt tcatccatcc tattttttta    1260
ggattcatca catttattgg gattagatta gagattttaa ttgatcctag aaataatttt    1320
tttagtctac ttctaagaag cttagtattt ttttctattc taattaccta tattatgttt    1380
acatctgaaa agaaaataat tgaagaaatt tttgataaat ag                       1422
```

<210> SEQ ID NO 13
<211> LENGTH: 1167
<212> TYPE: DNA
<213> ORGANISM: Lactococcus lactis subsp. lactis

<400> SEQUENCE: 13

```
atgaaaatag cagttgttgg gacaggctat gtcggtttgt ctatttcagt gcttctagca     60
caacatcatg aagttgttgc tttggatatt gttgaggcga agtagatttt gattaactct    120
aaaaaatcgc ctattgttga taaggagatt gagggatttt tagcaagtaa agaattaaat    180
ttacttgcga cgacggatac ggctcaagcg ctaaatagag ctgactttgt ggtcattgca    240
acacctacca attatgatga tgtcaagaat tattttaata cggattctgt agaagcagta    300
attgaagaag tttggaaatt tagcccaaat gctatgattg ttataaaatc aactattcca    360
gttggttttg tggaaaaaat gcgtgctaaa tatgatattg ataacattat cttttctcca    420 gaattttac gagaaggtcg agcattgtat gacaatcttc atccatctcg cattgttgtg    480
ggggaacaat ctgagcgtgc ctctcaattt gctgagcttt taatagaggg agctattgat    540
aaagatatcc cagttctttt tacaaaccct actgaagcag aagcgattaa gctattttca    600
aatacatatt tagctttacg cgtggcttat tttaatgaat tagatactta tgctgaagtt    660
cgtggtttag atacaaaaca aatcattgat ggcgttggat tagatccacg aattggaaca    720
cactacaata atccttcatt tggttatgga gggtattgcc taccgaaaga taccaaacag    780
cttttagcta actacgacca agttcctgaa aaattaattg aggctgttgt tgaatcaaat    840
agtacaagaa aagatcatat tgcagatatg atcattaaac gttctcctaa gtggtgggt    900 atctaccgct tgactatgaa gtcaaattct gataatttta tgatcaagttc aattcaagga    960 attatgaaac gaattaaggg caagggaatt gaagtagttg tctatgagcc aacactaaat   1020
gatactcatt tctacaattc tcgggtagtt cataatttgg atgagtttaa aacgatttct   1080
gatgtgattg ttttcaaatcg ttatactaaa gaacttgagg atgttaaaac taaagtttat   1140
acgagagatt tatttggccg tgactaa                                      1167
```

<210> SEQ ID NO 14
<211> LENGTH: 903
<212> TYPE: DNA
<213> ORGANISM: Lactococcus lactis subsp. lactis

<400> SEQUENCE: 14

```
ttggaacgaa aaaaaagaa aaaaagaat atttgggtta taattatacc tatcttaatt     60
tttattaccc ttataggagc aggggcttat gccttaagag attcacttat ttctactgat    120
catacgaaaa caaatagttc ggatcaaccg accaaaactt cggcctctaa tggttatgta    180
gagaaaaaag gtaaagaagc tgctgtgggt agtatagcac ttgtagatga tgttggtata    240
ccagaatgga ttaaggttcc ctcaaaggca aatctagata aatttactga tttatctacg    300
aataatatca ctatttatcg aattaataat ccggaagtct aaaaacagt taccaatcgt    360
```

| acagatcaac | ggatgaaaat | gtcagaagtt | atagctaagt | atcctaatgc | tttgattatg | 420 |
| aatgcttccg | cttttgatat | gcagacagga | caagtagttg | gatttcaaat | gaataatgga | 480 |
| aagttaattc | aagactggaa | tccaggtaca | acgactcaat | atgcttttgt | tattaacaaa | 540 |
| gatggttcat | gcaaaattta | tgattcaagt | acacctgctt | caactattat | aaaaacgga | 600 |
| gggcaacaag | cctatgattt | tggtacggca | attatccgtg | atggtaaaat | tcaaccaagt | 660 |
| gatggctcag | tagattggaa | gatccatatt | tttattgcga | atgataaaga | taataatctc | 720 |
| tatgctatt | tgagtgatac | aaatgcaggt | tatgataata | taatgaagtc | agtgtcaaat | 780 |
| ttgaagctcc | aaaatatgct | gttacttgat | agtggtggct | caagtcaact | atctgtcaat | 840 |
| ggtaaaacga | ttgttgctag | tcaagatgat | cgagccgtgc | cggattatat | tgtgatgaaa | 900 |
| taa | | | | | | 903 |

<210> SEQ ID NO 15
<211> LENGTH: 903
<212> TYPE: DNA
<213> ORGANISM: Lactococcus lactis subsp. lactis

<400> SEQUENCE: 15

| atgaatcaaa | aaagaggcg | tcattatcgt | aagaaaaaac | acacagtact | aaaagttatt | 60 |
| tcaattattt | ttgtattagt | aattatcgct | gttgcttcta | tagcctacgt | agcttataga | 120 |
| aatgttgaat | caacctttc | aacatcatat | gaaaatttcc | ctaaaacaac | aagtattgac | 180 |
| ttaaaaaat | ctaaaacatt | caccacactt | atcattgcaa | ctggtaaaaa | taattctaaa | 240 |
| aatacagctt | atgctactgt | tttagcttca | acgaatgtaa | agacaaatca | aactactttc | 300 |
| atgaacttcc | cagttttgc | gacaatgcct | aatcaaaaaa | caatcactga | agtttacaat | 360 |
| acgaatggag | atgatggaat | tttccagatg | gttaaagacc | tattgaatgt | gtccattaac | 420 |
| aaagtaattc | agattgatgt | taataaaatg | ggatcacttg | tacaggctac | tggtggaatc | 480 |
| accatgcaaa | atccaaaggc | attcaatgct | gaaggttatg | agtttaaaca | aggaactgtt | 540 |
| aatttacaaa | ctgctgatca | agtccaagcc | tatatgacac | aaattgacga | tactgatttg | 600 |
| gatgcttcaa | tcactcggat | tcaaaatgtc | tcaatggaac | tctacggaaa | tattcaaaaa | 660 |
| gttgctcata | tgaaaaaact | tgaaagtttc | aattactatc | gcgaaattct | ctatgctttt | 720 |
| tcaaacactg | ttaaaaccaa | tataagtttc | aatgatgcta | aaacgatcgt | tatgagctac | 780 |
| aataaggctc | taagaatac | cggcaagctt | aatctacata | caacagatga | aaatggagct | 840 |
| aaggtcgttt | ctcaaacaga | attagactca | gtcaaaaccc | ttttgaaaa | atctctaaaa | 900 |
| taa | | | | | | 903 |

<210> SEQ ID NO 16
<211> LENGTH: 7097
<212> TYPE: DNA
<213> ORGANISM: Lactococcus lactis subsp. lactis

<400> SEQUENCE: 16

| aaaacaatga | aaaaaagaa | attattacta | ataagtcaaa | gcggaagagg | tggagtaagg | 60 |
| aaacatcttt | gtgatttact | tacttctctt | gattataaaa | aatttgagat | ttggattgcc | 120 |
| tataatgatg | atgaggtcga | tgagattttt | aaatatacgt | tggaaagttt | aaggggaaaa | 180 |
| gttaaaccaa | tcattataaa | agaaatggtt | agagaactta | atcctaaaca | agattggatt | 240 |
| gcatttaaga | aaattcgtag | gtcaataaaa | agagataaaac | cagatattgt | tcattgccat | 300 |
| agttcgaaag | cgggaatatt | agggcgagca | gctgcaaaaa | tagtgggtat | aaaacaaata | 360 |

```
tattacacac ctcacgctta ctcttttctc gctacagaat tttcagtaaa aaagaaaaga      420
ttattcatta atctagaacg ttttttagt cattatgcta caactttaac atttaccgtg       480
tcagaaggtg aaaagaagc agcactaaaa aacaaagttg atagcaatga gaaatttaaa       540
gtaatttata atggattgaa agatataaaa atcttatcta aaatagaagc cagggaaaaa      600
cttggattac cacaagataa atttatttttt ggtaatattg ctcgaatttg tgaacaaaaa     660
aatccaattt attttataga agttgctcaa aaaaatcctg attattattt tgtttggatt     720
ggtgatggtg aacttcgtga gaaagtcaaa caagaaattc tctatagaaa cctgaaaaat      780
atttgtttct taggaaatag aaatgatgca ggaataatgg tcgcggcatt cgatgtgttt      840
atatctactt ctaaatatga aggactgccc tattcaccta ttgaagctct ccgagctgga      900
gtgcctgttt tgttaagtga tgttgttggt aataatgaag ttgtcttaag ccatagaaat      960
ggggaagttt ttgatttaaa ttcgtctaat tggaataaaa gacttgatga atttagaaag     1020
tggcaaaaga agaaaacgag tatagagatc agacaaacgt ttcttaatca cttctcattg     1080
gataaatcga taaagaact aactaagata tatttgaata atgagtaata ggcaacagtt      1140
acatagctat tttcatccaa caagtgattc tatggctttc ctatgatcaa caaatttagt     1200
agttatgttt tattgtagcc taatattcca aaacaattta aaacattaaa attcaagtaa     1260 cttttagtt aattaaattc ggataggctt aataaaattg tggattaaat taacttatat      1320
gcagattcta ctgagattag ggtcatgatc gcttgtatta attatttcac acataaccag     1380
gagtaagatt tatgcttatt tatttttcttt tatttcctat aattatttta ttatatattt    1440
ttacaaacaa cggactatta aagagtaaaa aaatatttat aggactttca ttctccatac     1500
tagggattat ttcgtctata cgttctcctc aagtaggaac cgatacatca acttaccaaa     1560 cactttttctt ctatcaaata catggaataa aaatattcaa ttcaaacaat ccggagttaa     1620
gcagcaaagc tccactttat ggtgtatata gtcgtattgt aagtatgatt tcagtaaatt     1680
tacagaccat tactatagct aattcattgc tgatagcatt cttatttgga attttttattt    1740 atagattgaa aattaatccg ctatattcaa ctttattatt tattagtatt ggattttca      1800 caagttctct taatacatct cgacagttta tcgctatcgg tttagtatgc aatgctctgc     1860
tatttctatt tgataaaaag gcatttatat attttgcttt aatcacatta gcaatatcta     1920
ttcatacgct agcaatagtt ggattgatat tttatccgat ttataagatt aaatggacag     1980
cagtaaaaat atcctgtttt ctaattgtgt tgacaatgac aagcttttttc cttgagtctg     2040 tttcgaaaat ttttattcaa ttttttcccca attacgcttt ttacttacaa aatcccgtga    2100
cattctttgg tgcttctagc cgtataataa tgattttaga tattggacta attttaatta    2160
ttttattatt ttatgcgttg actaaatact atcatattaa gtgtagtcaa gaagaagttt    2220
ctttgcttat cattttctta attggaccat ttttttgaaat acttgtatttt cacaatcaga   2280 gtatattact tttgactcaa cgatttctaa ctttttttc tattttaagt attgctgtaa     2340
ttccaggaat gtgtgctaaa gtttcaaaaa aattcaataa cccagaaaat gtgagttttg     2400 cttttttttag tgttatattt attttcacat tattcacttt ttctgtagaa attcaaaaat    2460
attggggagt tattccctat attacttttta tgtaattaga aaggtttatt taaatatgct    2520
aatttctgta ataattccaa tgtataatag aaaatttaca ataagagag ctatgaacag      2580 tgtacttct caagtaccaa ataaaaagga gtttcaaatt gaattaattg ttgttgatga      2640
ctgctccact gacaatagtg ttgaggttgc tagagaaata aaggatgaac gggtaaaaat     2700
```

```
tgtcaaactt gataaaaact cggtgctaa tgttgcgaga aattatggaa ttaatttagc    2760
aaatggtgag ataatcgctt ttaatgattc agatgatgaa tggcttcctg aaaaactttc    2820
taagcaactt gaagtacttc aagaaaaaaa tatagatttt ttgtgctgta atatggaaac    2880
ggatgtttac agtggaaaaa tgaaaatgct tacgcctaga ccgtcaggtt ttgttccaat    2940
tgaagaattg cttggaaaaa attatatagt aagtactcag aatttgattg aaaagctga    3000
tatgtttaaa tctaatcaat tcagtcatga aatctctcgt tttcaagact gggagcttat    3060
tctacggctt ttgattaagg ggtataggct ttattttatg gaagaagtat tagtgagaca    3120
gtatattcaa ccaaatagtt tatccaaaaa tttaaaaaat ggtgttttgt ctctccgata    3180
tatgcttgag gaattcaaag aagagtatgc acagcatcct ttacaaaagg cagaggtaat    3240
attaactgtt ggtagccatt tacacaatat gaattatcga tgtgctcaat tttattttaa    3300
atctttgaag ttaagattta gcatgactgt attggcaaaa gcactttta tgttttttac     3360
ggacttatca agaaagaagg aaagcgaatg acagagagga ttacagtgat tctttccgca    3420
tataacggtg agaaatatat tcaaagtcaa atagacagta tacttaatca aacatatgat    3480
aatttattt tatatattag agatgatgga tcaactgacg gaactcgaaa aattctgaag    3540
caatattctg aaaaagattc acgagtgaaa gttcaatatg gtgaaaacat aggctatgta    3600
aaaagttttt ttaaaatgct ttctgaagtc aattcggaat atatagcatt ttctgatcaa    3660
gatgatattt ggctgcctga aaagttatca gtcgctcaag cagctttatc acagaaaaat    3720
aagagcgttc ctctcatgtg ggcctcaaat atatatat gtgatgaaaa atgaatgta      3780
atttcgattg gtgcaaggaa gagaatgagt aatttctcaa attctctttt tatgtgtaat    3840
actcaaggaa tgacaatgat aattaataat aaagctagag aaaaggttgt ttctaatcta    3900
ccaaaacaaa atatcatgta ccacgattgg tggatttatc gcgttgttag tgctttcgga    3960
gaagttatat ttgattcaga tccatatgta aagtatagaa gacatgataa aaatgaatct    4020
gatatttcat ataattttgt gaataaagtc actaatatga tgaaccgctt aataaatagc    4080
gatatgtata tacgtacgaa gaaagagaca caagaattta aaataatttt tgattcacaa    4140
cttttcacaat caaatagaga tgtattaagt ttatttgcct caccaaaaag aaaaattcaa    4200
aaagtcttct actcaggtag attcaaaaat tccgtattag atgaactagt acttcgctta    4260
tttttttcttt tagacatttt ataattaaaa aattttttaa tagttataca ttataagata    4320
agttgtttgt atagtacttt aatggtatta aattatagag gtaagctatt agacgagaat    4380
tttttattt tacaacttgg aaaacagact ctaacaaggg gaaatgagaa ataaatgaat    4440
aataaattaa gagaaggttt tactttaca gcaattggta catatagtaa tttttaatt    4500
caaattattg tacaagcaat tttaagtcga ttattatcgc caagagagta tggaataatt    4560
gctatcatgc aagttttat agttttttt gcaatgctgg tggaagcagg aatgggacct    4620
gctatcatac aaaataaaaa gttaacaaac agagacaata tgaatttatt taacttttca    4680
gctattttt ctattatatt tgcgattata tttggttttt taggattatt acttacaaag    4740
atatatatga atccagcata cacttactta acttggattc agtctatttc aatattattt    4800
attgggttaa atattgttcc gactgcactc cttaataaaa gaaaacaatt caaagctgta    4860
aatttttagta cagtagtagg ggggatacta tcgggagtag tcggagttac aatggctttc    4920
ctgggatttg gtatttattc actaattgca agtgccatta caacggcatt tgtaagttt    4980
tgcttaaaca ggtattttgc taatatttgg tttactaaaa attggaataa atcttctttg    5040
atttctatt ggactgtttc gcggaatcag tttggaacaa attttataaa ttattttcg     5100
```

-continued

```
aataattcag acaatatttt agtaggaaaa tttatgggag atacagcact agctaattac    5160
aataagtctt atcaactgtt aacaatccct accactttat tgttgaatat agttaatcca    5220
gttttacaac caattctctc agattatcaa gatgatgttg taactataag aaaaacatac    5280
tataatattg ttcacttatt ggctctcatc gggattccta catcaatttt tcttagtatg    5340
tctgcaaaac aaattatttt tttctttttt ggaagtcagt gggaagaagc agtagttccc    5400
ttctcttact tagcagttat tgtatggtgt caaatgacaa catattcaaa tggagcaatc    5460
tggcagtcca gaaataaaac aaattatttt cttttttcaa gtgttatcaa tacttttatt    5520 ataattttt ctatcataat aggtatcata ataggaaata taaatgcggt tgctttattt    5580
gttgcaatag gaaattttat aagttttttt tggaaattct actatattac taaaaatgca    5640
ttagaagatt ctataagaaa tctactaaag atttcatcc atcctatttt tttaggattc    5700
atcacattta ttgggattag attagagatt ttaattgatc ctagaaataa ttttttttagt    5760 ctacttctaa gaagcttagt attttttttct attctaatta cctatattat gtttacatct    5820
gaaaagaaaa taattgaaga aattttttgat aaatagtcaa tgcatctata agatactaaa    5880
ggattccaaa aatatataag gagaaaaaca tgaaaatagc agttgttggg acaggctatg    5940
tcggtttgtc tatttcagtg cttctagcac aacatcatga agttgttgct ttggatattg    6000
ttgaggcgaa agtagatttg attaactcta aaaaatcgcc tattgttgat aaggagattg    6060 agggatttt agcaagtaaa gaattaaatt tacttgcgac gacggatacg gctcaagcgc    6120
taaatagagc tgactttgtg gtcattgcaa cacctaccaa ttatgatgat gtcaagaatt    6180 atttttaatac ggattctgta gaagcagtaa ttgaagaagt ttggaaattt agcccaaatg    6240
ctatgattgt tataaaatca actattccag ttggttttgt ggaaaaaatg cgtgctaaat    6300
atgatattga taacattatc ttttctccag aattttttacg agaaggtcga gcattgtatg    6360
acaatcttca tccatctcgc attgttgtgg gggaacaatc tgagcgtgcc tctcaatttg    6420
ctgagctttt aatagaggga gctattgata agatatccc agttctttt acaaacccta    6480 ctgaagcaga agcgattaag ctattttcaa atacatattt agcttacgc gtggcttatt    6540 ttaatgaatt agatacttat gctgaagttc gtggtttaga tacaaaacaa atcattgatg    6600
gcgttggatt agatccacga attggaacac actacaataa tccttcattt ggttatggag    6660
ggtattgcct accgaaagat accaaacagc ttttagctaa ctacgaccaa gttcctgaaa    6720
aattaattga ggctgttgtt gaatcaaata gtacaagaaa agatcatatt gcagatatga    6780
tcattaaacg ttctcctaaa gtggtgggta tctaccgctt gactatgaag tcaaattctg    6840 ataatttttag atcaagttca attcaaggaa ttatgaaacg aattaagggc aagggaattg    6900
aagtagttgt ctatgagcca acactaaatg atactcattt ctacaattct cgggtagttc    6960
ataatttgga tgagtttaaa acgatttctg atgtgattgt ttcaaatcgt tatactaaag    7020
aacttgagga tgtaaaaact aaagtttata cgagagattt atttggccgt gactaaacaa    7080
caattttgga ggaaaaa                                                   7097
```

<210> SEQ ID NO 17
<211> LENGTH: 105
<212> TYPE: PRT
<213> ORGANISM: Lactococcus lactis subsp. lactis

<400> SEQUENCE: 17

```
Met Asn Asp Leu Phe Tyr His Arg Leu Lys Glu Leu Val Glu Ser Ser
1               5                   10                  15
```

Gly Lys Ser Ala Asn Gln Ile Glu Arg Glu Leu Gly Tyr Pro Arg Asn
            20                  25                  30

Ser Leu Asn Asn Tyr Lys Leu Gly Glu Pro Ser Gly Thr Arg Leu
        35                  40                  45

Ile Gly Leu Ser Glu Tyr Phe Ser Val Ser Pro Lys Tyr Leu Met Gly
50                  55                  60

Ile Ile Asp Glu Pro Asn Asp Ser Ser Ala Ile Asn Leu Phe Lys Ser
65                  70                  75                  80

Leu Thr Gln Glu Glu Lys Lys Glu Met Cys Ile Ile Cys Gln Lys Trp
                85                  90                  95

Leu Phe Leu Glu Tyr Gln Ile Glu Leu
                100                 105

<210> SEQ ID NO 18
<211> LENGTH: 255
<212> TYPE: PRT
<213> ORGANISM: Lactococcus lactis subsp. lactis

<400> SEQUENCE: 18

Met Met Lys Lys Gly Ile Phe Val Ile Thr Ile Val Ile Ser Ile Ala
1               5                   10                  15

Leu Ile Ile Gly Gly Phe Tyr Ser Tyr Asn Ser Arg Ile Asn Asn Leu
            20                  25                  30

Ser Lys Thr Asn Asn Gly Lys Glu Val Val Lys Asn Ser Glu Lys
        35                  40                  45

Asn Gln Ile Glu Leu Thr Tyr Lys Lys Tyr Tyr Lys Asn Leu Pro Lys
50                  55                  60

Ser Val Gln Asn Lys Ile Asp Asp Ile Ser Ser Lys Asn Lys Glu Val
65                  70                  75                  80

Thr Leu Thr Cys Ile Trp Gln Ser Asp Ser Val Ile Ser Glu Gln Phe
                85                  90                  95

Gln Gln Asn Leu Gln Lys Tyr Tyr Gly Asn Lys Phe Trp Asn Ile Lys
                100                 105                 110

Asn Ile Thr Tyr Asn Gly Glu Thr Ser Glu Gln Leu Leu Ala Glu Lys
            115                 120                 125

Val Glu Asn Gln Val Leu Ala Thr Asn Pro Asp Val Val Leu Tyr Glu
130                 135                 140

Ala Pro Leu Phe Asn Asp Asn Gln Asn Ile Glu Ala Thr Ala Ser Leu
145                 150                 155                 160

Thr Ser Asn Glu Gln Leu Ile Thr Asn Leu Ala Ser Ala Gly Ala Glu
                165                 170                 175

Val Ile Val Gln Pro Ser Pro Ile Tyr Gly Gly Val Val Tyr Pro
                180                 185                 190

Val Gln Glu Glu Gln Phe Lys Gln Ser Leu Ser Thr Lys Tyr Pro Tyr
            195                 200                 205

Ile Asp Tyr Trp Ala Ser Tyr Pro Asp Lys Asn Ser Asp Glu Met Lys
210                 215                 220

Gly Leu Phe Ser Asp Asn Gly Val Tyr Arg Thr Leu Asn Ala Ser Gly
225                 230                 235                 240

Asn Lys Val Trp Leu Asp Tyr Ile Thr Lys Tyr Phe Thr Ala Asn
                245                 250                 255

<210> SEQ ID NO 19
<211> LENGTH: 259
<212> TYPE: PRT

<213> ORGANISM: Lactococcus lactis subsp. lactis

<400> SEQUENCE: 19

```
Met Gln Glu Thr Gln Glu Gln Thr Ile Asp Leu Arg Gly Ile Phe Lys
1               5                   10                  15

Ile Ile Arg Lys Arg Leu Gly Leu Ile Leu Phe Ser Ala Leu Ile Val
                20                  25                  30

Thr Ile Leu Gly Ser Ile Tyr Thr Phe Phe Ile Ala Ser Pro Val Tyr
            35                  40                  45

Thr Ala Ser Thr Gln Leu Val Val Lys Leu Pro Asn Ser Asp Asn Ser
    50                  55                  60

Ala Ala Tyr Ala Gly Gln Val Thr Gly Asn Ile Gln Met Ala Asn Thr
65                  70                  75                  80

Ile Asn Gln Val Ile Val Ser Pro Val Ile Leu Asp Lys Val Gln Ser
                85                  90                  95

Asn Leu Asn Leu Ser Asp Asp Ser Phe Gln Lys Gln Val Thr Ala Ala
            100                 105                 110

Asn Gln Thr Asn Ser Gln Val Ile Thr Leu Thr Val Lys Tyr Ser Asn
        115                 120                 125

Pro Tyr Val Ala Gln Lys Ile Ala Asp Glu Thr Ala Lys Ile Phe Ser
    130                 135                 140

Ser Asp Ala Ala Lys Leu Leu Asn Val Thr Asn Val Asn Ile Leu Ser
145                 150                 155                 160

Lys Ala Lys Ala Gln Thr Thr Pro Ile Ser Pro Lys Pro Lys Leu Tyr
                165                 170                 175

Leu Ala Ile Ser Val Ile Ala Gly Leu Val Leu Gly Leu Ala Ile Ala
            180                 185                 190

Leu Leu Lys Glu Leu Phe Asp Asn Lys Ile Asn Lys Glu Glu Asp Ile
        195                 200                 205

Glu Ala Leu Gly Leu Thr Val Leu Gly Val Thr Thr Tyr Ala Gln Met
    210                 215                 220

Ser Asp Phe Asn Lys Asn Thr Asn Lys Asn Gly Thr Gln Ser Gly Thr
225                 230                 235                 240

Lys Ser Ser Pro Pro Ser Asp His Glu Val Asn Arg Ser Ser Lys Arg
                245                 250                 255

Asn Lys Arg
```

<210> SEQ ID NO 20
<211> LENGTH: 231
<212> TYPE: PRT
<213> ORGANISM: Lactococcus lactis subsp. lactis

<400> SEQUENCE: 20

```
Met Ala Lys Asn Lys Arg Ser Ile Asp Asn Asn Arg Tyr Ile Ile Thr
1               5                   10                  15

Ser Val Asn Pro Gln Ser Pro Ile Ser Glu Gln Tyr Arg Thr Ile Arg
                20                  25                  30

Thr Thr Ile Asp Phe Lys Met Ala Asp Gln Gly Ile Lys Ser Phe Leu
            35                  40                  45

Val Thr Ser Ser Glu Ala Ala Gly Lys Ser Thr Val Ser Ala Asn
    50                  55                  60

Leu Ala Val Ala Phe Ala Gln Gln Gly Lys Val Leu Leu Ile Asp
65                  70                  75                  80

Gly Asp Leu Arg Lys Pro Thr Val Asn Ile Thr Phe Lys Val Gln Asn
                85                  90                  95
```

```
Arg Val Gly Leu Thr Asn Ile Leu Met His Gln Ser Ser Ile Glu Asp
            100                 105                 110

Ala Ile Gln Gly Thr Arg Leu Ser Glu Asn Leu Thr Ile Ile Thr Ser
            115                 120                 125

Gly Pro Ile Pro Pro Asn Pro Ser Glu Leu Leu Ala Ser Ser Ala Met
130                 135                 140

Lys Asn Leu Ile Asp Ser Val Ser Asp Ser Phe Asp Ile Val Leu Ile
145                 150                 155                 160

Asp Thr Pro Pro Leu Ser Ala Val Thr Asp Ala Gln Ile Leu Ser Ile
                165                 170                 175

Tyr Val Gly Gly Val Val Leu Val Val Arg Ala Tyr Glu Thr Lys Lys
            180                 185                 190

Glu Ser Leu Ala Lys Thr Lys Lys Ile Leu Glu Gln Val Asn Val Asn
            195                 200                 205

Ile Leu Gly Val Val Leu His Gly Val Asp Ser Ser Glu Ser Pro Ser
210                 215                 220

Tyr Tyr Tyr Tyr Gly Val Glu
225                 230
```

<210> SEQ ID NO 21
<211> LENGTH: 254
<212> TYPE: PRT
<213> ORGANISM: Lactococcus lactis subsp. lactis

<400> SEQUENCE: 21

```
Met Ile Asp Ile His Cys His Ile Leu Pro Gly Ile Asp Asp Gly Ala
1               5                   10                  15

Lys Thr Ser Gly Asp Thr Leu Thr Met Leu Lys Ser Ala Ile Asp Glu
            20                  25                  30

Gly Ile Thr Ala Ile Thr Ala Thr Pro His His Asn Pro Gln Phe Asn
        35                  40                  45

Asn Glu Ser Pro Leu Ile Leu Lys Lys Val Lys Glu Val Gln Asn Ile
    50                  55                  60

Ile Asp Glu His Gln Leu Pro Ile Glu Val Leu Pro Gly Gln Glu Val
65                  70                  75                  80

Arg Ile Tyr Gly Asp Leu Leu Lys Glu Phe Ser Glu Gly Lys Leu Leu
                85                  90                  95

Thr Ala Ala Gly Thr Ser Ser Tyr Ile Leu Ile Glu Phe Pro Ser Asn
            100                 105                 110

His Val Pro Ala Tyr Ala Lys Glu Leu Phe Tyr Asn Ile Gln Leu Glu
            115                 120                 125

Gly Leu Gln Pro Ile Leu Val His Pro Glu Arg Asn Ser Ala Ile Ile
        130                 135                 140

Glu Asn Pro Asp Ile Leu Phe Asp Phe Ile Glu Gln Gly Val Leu Ser
145                 150                 155                 160

Gln Ile Thr Ala Ser Ser Val Thr Gly His Phe Gly Lys Lys Ile Gln
                165                 170                 175

Lys Leu Ser Phe Lys Met Ile Glu Asn His Leu Thr His Phe Val Ala
            180                 185                 190

Ser Asp Ala His Asn Val Thr Ser Arg Ala Phe Lys Met Lys Glu Ala
            195                 200                 205

Phe Glu Met Ile Glu Asp Ser Tyr Gly Ser Gly Val Ser Arg Arg Phe
210                 215                 220

Lys Asp Asn Ala Glu Ser Val Ile Leu Asn Glu Ser Phe Tyr Gln Glu
```

```
                  225                 230                 235                 240

Lys Pro Thr Lys Ile Lys Thr Lys Lys Phe Leu Gly Leu Phe
                245                 250

<210> SEQ ID NO 22
<211> LENGTH: 228
<212> TYPE: PRT
<213> ORGANISM: Lactococcus lactis subsp. lactis

<400> SEQUENCE: 22

Met Glu Val Phe Glu Asp Ala Ser Ser Pro Glu Ser Glu His Lys
1               5                   10                  15

Leu Val Val Leu Lys Asn Phe Ser Tyr Gly Leu Ile Ile Lys Arg
                20                  25                  30

Ala Ile Asp Ile Leu Gly Gly Leu Ala Gly Ser Val Leu Phe Leu Ile
                35                  40                  45

Ala Ala Ala Leu Leu Tyr Val Pro Tyr Lys Met Ser Ser Glu Lys Asp
            50                  55                  60

Gln Gly Pro Met Phe Tyr Lys Gln Lys Arg Val Gly Lys Asn Gly Lys
65                  70                  75                  80

Ile Phe Tyr Ile Leu Lys Phe Arg Thr Met Ile Ile Asn Ala Glu Gln
                85                  90                  95

Tyr Leu Glu Leu His Pro Glu Val Lys Ala Ala Tyr His Ala Asn Gly
                100                 105                 110

Asn Lys Leu Glu Asn Asp Pro Arg Val Thr Lys Ile Gly Ser Phe Ile
                115                 120                 125

Arg Gln Tyr Ser Val Asp Glu Leu Pro Gln Phe Ile Asn Val Leu Lys
                130                 135                 140

Gly Asp Met Ala Leu Val Gly Pro Arg Pro Ile Gln His Phe Glu Ala
145                 150                 155                 160

Lys Glu Phe Gly Glu Arg Leu Pro Tyr Leu Leu Ile Cys Lys Pro Gly
                165                 170                 175

Ile Thr Gly Tyr Trp Thr Thr His Gly Arg Ser Lys Ala Pro Phe Pro
                180                 185                 190

Gln Arg Ala Asp Leu Glu Leu Tyr Tyr Leu Gln Tyr His Ser Thr Lys
                195                 200                 205

Asn Asp Val Lys Leu Leu Met Leu Thr Ile Ala Gln Ile Ile His Gly
                210                 215                 220

Ser Asp Ala Tyr
225

<210> SEQ ID NO 23
<211> LENGTH: 373
<212> TYPE: PRT
<213> ORGANISM: Lactococcus lactis subsp. lactis

<400> SEQUENCE: 23

Met Lys Lys Lys Lys Leu Leu Leu Ile Ser Gln Ser Gly Arg Gly Gly
1               5                   10                  15

Val Arg Lys His Leu Cys Asp Leu Leu Thr Ser Leu Asp Tyr Lys Lys
                20                  25                  30

Phe Glu Ile Trp Ile Ala Tyr Asn Asp Asp Glu Val Asp Glu Ile Phe
                35                  40                  45

Lys Tyr Thr Leu Glu Ser Leu Arg Gly Lys Val Lys Pro Ile Ile Ile
                50                  55                  60

Lys Glu Met Val Arg Glu Leu Asn Pro Lys Gln Asp Trp Ile Ala Phe
```

```
            65                  70                  75                  80
Lys Lys Ile Arg Arg Ser Ile Lys Glu Ile Lys Pro Asp Ile Val His
                85                  90                  95
Cys His Ser Ser Lys Ala Gly Ile Leu Gly Arg Ala Ala Lys Ile
            100                 105                 110
Val Gly Ile Lys Gln Ile Tyr Tyr Thr Pro His Ala Tyr Ser Phe Leu
        115                 120                 125
Ala Thr Glu Phe Ser Val Lys Lys Arg Leu Phe Ile Asn Leu Glu
    130                 135                 140
Arg Phe Phe Ser His Tyr Ala Thr Thr Leu Thr Phe Thr Val Ser Glu
145                 150                 155                 160
Gly Glu Lys Glu Ala Ala Leu Lys Asn Lys Val Asp Ser Asn Glu Lys
                165                 170                 175
Phe Lys Val Ile Tyr Asn Gly Leu Lys Asp Ile Lys Ile Leu Ser Lys
            180                 185                 190
Ile Glu Ala Arg Glu Lys Leu Gly Leu Pro Gln Asp Lys Phe Ile Phe
        195                 200                 205
Gly Asn Ile Ala Arg Ile Cys Glu Gln Lys Asn Pro Ile Tyr Phe Ile
    210                 215                 220
Glu Val Ala Gln Lys Asn Pro Asp Tyr Tyr Phe Val Trp Ile Gly Asp
225                 230                 235                 240
Gly Glu Leu Arg Glu Lys Val Lys Gln Glu Ile Leu Tyr Arg Asn Leu
                245                 250                 255
Lys Asn Ile Cys Phe Leu Gly Asn Arg Asn Asp Ala Gly Ile Met Val
            260                 265                 270
Ala Ala Phe Asp Val Phe Ile Ser Thr Ser Lys Tyr Glu Gly Leu Pro
        275                 280                 285
Tyr Ser Pro Ile Glu Ala Leu Arg Ala Gly Val Pro Val Leu Leu Ser
    290                 295                 300
Asp Val Val Gly Asn Asn Glu Val Val Leu Ser His Arg Asn Gly Glu
305                 310                 315                 320
Val Phe Asp Leu Asn Ser Ser Asn Trp Asn Lys Arg Leu Asp Glu Phe
                325                 330                 335
Arg Lys Trp Gln Lys Lys Thr Ser Ile Glu Ile Arg Gln Thr Phe
            340                 345                 350
Leu Asn His Phe Ser Leu Asp Lys Ser Ile Lys Glu Leu Thr Lys Ile
        355                 360                 365
Tyr Leu Asn Asn Glu
    370

<210> SEQ ID NO 24
<211> LENGTH: 367
<212> TYPE: PRT
<213> ORGANISM: Lactococcus lactis subsp. lactis

<400> SEQUENCE: 24

Met Leu Ile Tyr Phe Leu Leu Phe Pro Ile Ile Leu Leu Tyr Ile
1               5                   10                  15
Phe Thr Asn Asn Gly Leu Leu Lys Ser Lys Lys Ile Phe Ile Gly Leu
                20                  25                  30
Ser Phe Ser Ile Leu Gly Ile Ile Ser Ser Ile Arg Ser Pro Gln Val
            35                  40                  45
Gly Thr Asp Thr Ser Thr Tyr Gln Thr Leu Phe Phe Tyr Gln Ile His
        50                  55                  60
```

```
Gly Ile Lys Ile Phe Asn Ser Asn Asn Pro Glu Leu Ser Ser Lys Ala
 65                  70                  75                  80

Pro Leu Tyr Gly Val Tyr Ser Arg Ile Val Ser Met Ile Ser Val Asn
                 85                  90                  95

Leu Gln Thr Ile Thr Ile Ala Asn Ser Leu Leu Ile Ala Phe Leu Phe
            100                 105                 110

Gly Ile Phe Ile Tyr Arg Leu Lys Ile Asn Pro Leu Tyr Ser Thr Leu
        115                 120                 125

Leu Phe Ile Ser Ile Gly Phe Phe Thr Ser Ser Leu Asn Thr Ser Arg
    130                 135                 140

Gln Phe Ile Ala Ile Gly Leu Val Cys Asn Ala Leu Leu Phe Leu Phe
145                 150                 155                 160

Asp Lys Lys Ala Phe Ile Tyr Phe Ala Leu Ile Thr Leu Ala Ile Ser
                165                 170                 175

Ile His Thr Leu Ala Ile Val Gly Leu Ile Phe Tyr Pro Ile Tyr Lys
            180                 185                 190

Ile Lys Trp Thr Ala Val Lys Ile Ser Cys Phe Leu Ile Val Leu Thr
        195                 200                 205

Met Thr Ser Phe Phe Leu Glu Ser Val Ser Lys Ile Phe Ile Gln Phe
    210                 215                 220

Phe Pro Asn Tyr Ala Phe Tyr Leu Gln Asn Pro Val Thr Phe Phe Gly
225                 230                 235                 240

Ala Ser Ser Arg Ile Ile Met Ile Leu Asp Ile Gly Leu Ile Leu Ile
                245                 250                 255

Ile Leu Leu Phe Tyr Ala Leu Thr Lys Tyr Tyr His Ile Lys Cys Ser
            260                 265                 270

Gln Glu Glu Val Ser Leu Leu Ile Ile Phe Leu Ile Gly Pro Phe Phe
        275                 280                 285

Glu Ile Leu Val Phe His Asn Gln Ser Ile Leu Leu Leu Thr Gln Arg
    290                 295                 300

Phe Leu Thr Phe Phe Ser Ile Leu Ser Ile Ala Val Ile Pro Gly Met
305                 310                 315                 320

Cys Ala Lys Val Ser Lys Lys Phe Asn Asn Pro Glu Asn Val Ser Phe
                325                 330                 335

Ala Phe Phe Ser Val Ile Phe Ile Thr Leu Phe Thr Phe Ser Val
            340                 345                 350

Glu Ile Gln Lys Tyr Trp Gly Val Ile Pro Tyr Ile Thr Phe Met
        355                 360                 365

<210> SEQ ID NO 25
<211> LENGTH: 291
<212> TYPE: PRT
<213> ORGANISM: Lactococcus lactis subsp. lactis

<400> SEQUENCE: 25

Met Leu Ile Ser Val Ile Pro Met Tyr Asn Arg Lys Phe Thr Ile
 1               5                  10                  15

Lys Arg Ala Met Asn Ser Val Leu Ser Gln Val Pro Asn Lys Lys Glu
                 20                  25                  30

Phe Gln Ile Glu Leu Ile Val Val Asp Asp Cys Ser Thr Asp Asn Ser
             35                  40                  45

Val Glu Val Ala Arg Glu Ile Lys Asp Glu Arg Val Lys Ile Val Lys
         50                  55                  60

Leu Asp Lys Asn Ser Gly Ala Asn Val Ala Arg Asn Tyr Gly Ile Asn
 65                  70                  75                  80
```

Leu Ala Asn Gly Glu Ile Ile Ala Phe Asn Asp Ser Asp Asp Glu Trp
            85                  90                  95

Leu Pro Glu Lys Leu Ser Lys Gln Leu Glu Val Leu Gln Glu Lys Asn
100                 105                 110

Ile Asp Phe Leu Cys Cys Asn Met Glu Thr Asp Val Tyr Ser Gly Lys
            115                 120                 125

Met Lys Met Leu Thr Pro Arg Pro Ser Gly Phe Val Pro Ile Glu Glu
            130                 135                 140

Leu Leu Gly Lys Asn Tyr Ile Val Ser Thr Gln Asn Leu Ile Gly Lys
145                 150                 155                 160

Ala Asp Met Phe Lys Ser Asn Gln Phe Ser His Glu Ile Ser Arg Phe
            165                 170                 175

Gln Asp Trp Glu Leu Ile Leu Arg Leu Leu Ile Lys Gly Tyr Arg Leu
            180                 185                 190

Tyr Phe Met Glu Glu Val Leu Val Arg Gln Tyr Ile Gln Pro Asn Ser
            195                 200                 205

Leu Ser Lys Asn Leu Lys Asn Gly Val Leu Ser Leu Arg Tyr Met Leu
            210                 215                 220

Glu Glu Phe Lys Glu Glu Tyr Ala Gln His Pro Leu Gln Lys Ala Glu
225                 230                 235                 240

Val Ile Leu Thr Val Gly Ser His Leu His Asn Met Asn Tyr Arg Cys
            245                 250                 255

Ala Gln Phe Tyr Phe Lys Ser Leu Lys Leu Arg Phe Ser Met Thr Val
            260                 265                 270

Leu Ala Lys Ala Leu Phe Met Phe Phe Thr Asp Leu Ser Arg Lys Lys
            275                 280                 285

Glu Ser Glu
   290

<210> SEQ ID NO 26
<211> LENGTH: 298
<212> TYPE: PRT
<213> ORGANISM: Lactococcus lactis subsp. lactis

<400> SEQUENCE: 26

Met Thr Glu Arg Ile Thr Val Ile Leu Ser Ala Tyr Asn Gly Glu Lys
1               5                   10                  15

Tyr Ile Gln Ser Gln Ile Asp Ser Ile Leu Asn Gln Thr Tyr Asp Asn
                20                  25                  30

Phe Ile Leu Tyr Ile Arg Asp Asp Gly Ser Thr Asp Gly Thr Arg Lys
            35                  40                  45

Ile Leu Lys Gln Tyr Ser Glu Lys Asp Ser Arg Val Lys Val Gln Tyr
        50                  55                  60

Gly Glu Asn Ile Gly Tyr Val Lys Ser Phe Phe Lys Met Leu Ser Glu
65                  70                  75                  80

Val Asn Ser Glu Tyr Ile Ala Phe Ser Asp Gln Asp Ile Trp Leu
            85                  90                  95

Pro Glu Lys Leu Ser Val Ala Gln Ala Leu Ser Gln Lys Asn Lys
        100                 105                 110

Ser Val Pro Leu Met Trp Ala Ser Asn Ile Tyr Ile Cys Asp Glu Lys
            115                 120                 125

Met Asn Val Ile Ser Ile Gly Ala Arg Lys Arg Met Ser Asn Phe Ser
            130                 135                 140

Asn Ser Leu Phe Met Cys Asn Thr Gln Gly Met Thr Met Ile Ile Asn

```
            145                 150                 155                 160
        Asn Lys Ala Arg Glu Lys Val Val Ser Asn Leu Pro Lys Gln Asn Ile
                        165                 170                 175

Met Tyr His Asp Trp Trp Ile Tyr Arg Val Ser Ala Phe Gly Glu
                    180                 185                 190

Val Ile Phe Asp Ser Asp Pro Tyr Val Lys Tyr Arg His Asp Lys
                        195                 200                 205

Asn Glu Ser Asp Ile Ser Tyr Asn Phe Val Asn Lys Val Thr Asn Met
            210                 215                 220

Met Asn Arg Leu Ile Asn Ser Asp Met Tyr Ile Arg Thr Lys Lys Glu
        225                 230                 235                 240

Thr Gln Glu Phe Lys Ile Ile Phe Asp Ser Gln Leu Ser Gln Ser Asn
                        245                 250                 255

Arg Asp Val Leu Ser Leu Phe Ala Ser Pro Lys Arg Lys Ile Gln Lys
                        260                 265                 270

Val Phe Tyr Ser Gly Arg Phe Lys Asn Ser Val Leu Asp Glu Leu Val
                        275                 280                 285

Leu Arg Leu Phe Phe Leu Leu Asp Ile Leu
            290                 295

<210> SEQ ID NO 27
<211> LENGTH: 473
<212> TYPE: PRT
<213> ORGANISM: Lactococcus lactis subsp. lactis

<400> SEQUENCE: 27

Met Asn Asn Lys Leu Arg Glu Gly Phe Thr Phe Thr Ala Ile Gly Thr
        1               5                   10                  15

Tyr Ser Asn Phe Leu Ile Gln Ile Ile Val Gln Ala Ile Leu Ser Arg
                        20                  25                  30

Leu Leu Ser Pro Arg Glu Tyr Gly Ile Ile Ala Ile Met Gln Val Phe
                    35                  40                  45

Ile Val Phe Phe Ala Met Leu Val Glu Ala Gly Met Gly Pro Ala Ile
            50                  55                  60

Ile Gln Asn Lys Lys Leu Thr Asn Arg Asp Asn Met Asn Leu Phe Asn
        65                  70                  75                  80

Phe Ser Ala Ile Phe Ser Ile Ile Phe Ala Ile Ile Phe Gly Phe Leu
                        85                  90                  95

Gly Leu Leu Leu Thr Lys Ile Tyr Met Asn Pro Ala Tyr Thr Tyr Leu
                        100                 105                 110

Thr Trp Ile Gln Ser Ile Ser Ile Leu Phe Ile Gly Leu Asn Ile Val
                    115                 120                 125

Pro Thr Ala Leu Leu Asn Lys Arg Lys Gln Phe Lys Ala Val Asn Phe
            130                 135                 140

Ser Thr Val Val Gly Gly Ile Leu Ser Gly Val Val Gly Val Thr Met
        145                 150                 155                 160

Ala Phe Leu Gly Phe Gly Ile Tyr Ser Leu Ile Ala Ser Ala Ile Thr
                        165                 170                 175

Thr Ala Phe Val Ser Phe Cys Leu Asn Arg Tyr Phe Ala Asn Ile Trp
                        180                 185                 190

Phe Thr Lys Asn Trp Asn Lys Ser Ser Leu Ile Ser Ile Trp Thr Val
                    195                 200                 205

Ser Arg Asn Gln Phe Gly Thr Asn Phe Ile Asn Tyr Phe Ser Asn Asn
            210                 215                 220
```

-continued

Ser Asp Asn Ile Leu Val Gly Lys Phe Met Gly Asp Thr Ala Leu Ala
225                 230                 235                 240

Asn Tyr Asn Lys Ser Tyr Gln Leu Leu Thr Ile Pro Thr Thr Leu Leu
            245                 250                 255

Leu Asn Ile Val Asn Pro Val Leu Gln Pro Ile Leu Ser Asp Tyr Gln
        260                 265                 270

Asp Asp Val Val Thr Ile Arg Lys Thr Tyr Tyr Asn Ile Val His Leu
    275                 280                 285

Leu Ala Leu Ile Gly Ile Pro Thr Ser Ile Phe Leu Ser Met Ser Ala
290                 295                 300

Lys Gln Ile Ile Phe Phe Phe Gly Ser Gln Trp Glu Glu Ala Val
305                 310                 315                 320

Val Pro Phe Ser Tyr Leu Ala Val Ile Val Trp Cys Gln Met Thr Thr
            325                 330                 335

Tyr Ser Asn Gly Ala Ile Trp Gln Ser Arg Asn Lys Thr Asn Tyr Phe
        340                 345                 350

Leu Phe Ser Ser Val Ile Asn Thr Phe Ile Ile Phe Ser Ile Ile
    355                 360                 365

Ile Gly Ile Ile Ile Gly Asn Ile Asn Ala Val Ala Leu Phe Val Ala
370                 375                 380

Ile Gly Asn Phe Ile Ser Phe Phe Trp Lys Phe Tyr Tyr Ile Thr Lys
385                 390                 395                 400

Asn Ala Leu Glu Asp Ser Ile Arg Asn Leu Leu Lys Ile Phe Ile His
            405                 410                 415

Pro Ile Phe Leu Gly Phe Ile Thr Phe Ile Gly Ile Arg Leu Glu Ile
        420                 425                 430

Leu Ile Asp Pro Arg Asn Asn Phe Phe Ser Leu Leu Leu Arg Ser Leu
    435                 440                 445

Val Phe Phe Ser Ile Leu Ile Thr Tyr Ile Met Phe Thr Ser Glu Lys
450                 455                 460

Lys Ile Ile Glu Glu Ile Phe Asp Lys
465                 470

<210> SEQ ID NO 28
<211> LENGTH: 388
<212> TYPE: PRT
<213> ORGANISM: Lactococcus lactis subsp. lactis

<400> SEQUENCE: 28

Met Lys Ile Ala Val Val Gly Thr Gly Tyr Val Gly Leu Ser Ile Ser
1               5                   10                  15

Val Leu Leu Ala Gln His His Glu Val Val Ala Leu Asp Ile Val Glu
            20                  25                  30

Ala Lys Val Asp Leu Ile Asn Ser Lys Lys Ser Pro Ile Val Asp Lys
        35                  40                  45

Glu Ile Glu Gly Phe Leu Ala Ser Lys Glu Leu Asn Leu Leu Ala Thr
    50                  55                  60

Thr Asp Thr Ala Gln Ala Leu Asn Arg Ala Asp Phe Val Val Ile Ala
65                  70                  75                  80

Thr Pro Thr Asn Tyr Asp Asp Val Lys Asn Tyr Phe Asn Thr Asp Ser
            85                  90                  95

Val Glu Ala Val Ile Glu Glu Val Trp Lys Phe Ser Pro Asn Ala Met
        100                 105                 110

Ile Val Ile Lys Ser Thr Ile Pro Val Gly Phe Val Glu Lys Met Arg
    115                 120                 125

Ala Lys Tyr Asp Ile Asp Asn Ile Ile Phe Ser Pro Glu Phe Leu Arg
    130                 135                 140

Glu Gly Arg Ala Leu Tyr Asp Asn Leu His Pro Ser Arg Ile Val Val
145                 150                 155                 160

Gly Glu Gln Ser Glu Arg Ala Ser Gln Phe Ala Glu Leu Leu Ile Glu
                165                 170                 175

Gly Ala Ile Asp Lys Asp Ile Pro Val Leu Phe Thr Asn Pro Thr Glu
            180                 185                 190

Ala Glu Ala Ile Lys Leu Phe Ser Asn Thr Tyr Leu Ala Leu Arg Val
        195                 200                 205

Ala Tyr Phe Asn Glu Leu Asp Thr Tyr Ala Glu Val Arg Gly Leu Asp
    210                 215                 220

Thr Lys Gln Ile Ile Asp Gly Val Gly Leu Asp Pro Arg Ile Gly Thr
225                 230                 235                 240

His Tyr Asn Asn Pro Ser Phe Gly Tyr Gly Gly Tyr Cys Leu Pro Lys
                245                 250                 255

Asp Thr Lys Gln Leu Leu Ala Asn Tyr Asp Gln Val Pro Glu Lys Leu
            260                 265                 270

Ile Glu Ala Val Val Glu Ser Asn Ser Thr Arg Lys Asp His Ile Ala
        275                 280                 285

Asp Met Ile Ile Lys Arg Ser Pro Lys Val Val Gly Ile Tyr Arg Leu
    290                 295                 300

Thr Met Lys Ser Asn Ser Asp Asn Phe Arg Ser Ser Ile Gln Gly
305                 310                 315                 320

Ile Met Lys Arg Ile Lys Gly Lys Gly Ile Glu Val Val Val Tyr Glu
                325                 330                 335

Pro Thr Leu Asn Asp Thr His Phe Tyr Asn Ser Arg Val Val His Asn
            340                 345                 350

Leu Asp Glu Phe Lys Thr Ile Ser Asp Val Ile Val Ser Asn Arg Tyr
        355                 360                 365

Thr Lys Glu Leu Glu Asp Val Lys Thr Lys Val Tyr Thr Arg Asp Leu
    370                 375                 380

Phe Gly Arg Asp
385

<210> SEQ ID NO 29
<211> LENGTH: 300
<212> TYPE: PRT
<213> ORGANISM: Lactococcus lactis subsp. lactis

<400> SEQUENCE: 29

Leu Glu Arg Lys Lys Lys Lys Lys Asn Ile Trp Val Ile Ile Ile
1               5                   10                  15

Pro Ile Leu Ile Phe Ile Thr Leu Ile Gly Ala Gly Ala Tyr Ala Leu
                20                  25                  30

Arg Asp Ser Leu Ile Ser Thr Asp His Thr Lys Thr Asn Ser Ser Asp
            35                  40                  45

Gln Pro Thr Lys Thr Ser Ala Ser Asn Gly Tyr Val Glu Lys Lys Gly
        50                  55                  60

Lys Glu Ala Ala Val Gly Ser Ile Ala Leu Val Asp Asp Val Gly Ile
65                  70                  75                  80

Pro Glu Trp Ile Lys Val Pro Ser Lys Ala Asn Leu Asp Lys Phe Thr
                85                  90                  95

Asp Leu Ser Thr Asn Asn Ile Thr Ile Tyr Arg Ile Asn Asn Pro Glu

```
            100                 105                 110
Val Leu Lys Thr Val Thr Asn Arg Thr Asp Gln Arg Met Lys Met Ser
            115                 120                 125
Glu Val Ile Ala Lys Tyr Pro Asn Ala Leu Ile Met Asn Ala Ser Ala
            130                 135                 140
Phe Asp Met Gln Thr Gly Gln Val Val Gly Phe Gln Met Asn Asn Gly
145                 150                 155                 160
Lys Leu Ile Gln Asp Trp Asn Pro Gly Thr Thr Thr Gln Tyr Ala Phe
            165                 170                 175
Val Ile Asn Lys Asp Gly Ser Cys Lys Ile Tyr Asp Ser Ser Thr Pro
            180                 185                 190
Ala Ser Thr Ile Ile Lys Asn Gly Gln Gln Ala Tyr Asp Phe Gly
            195                 200                 205
Thr Ala Ile Ile Arg Asp Gly Lys Ile Gln Pro Ser Asp Gly Ser Val
            210                 215                 220
Asp Trp Lys Ile His Ile Phe Ile Ala Asn Asp Lys Asp Asn Asn Leu
225                 230                 235                 240
Tyr Ala Ile Leu Ser Asp Thr Asn Ala Gly Tyr Asp Asn Ile Met Lys
            245                 250                 255
Ser Val Ser Asn Leu Lys Leu Gln Asn Met Leu Leu Leu Asp Ser Gly
            260                 265                 270
Gly Ser Ser Gln Leu Ser Val Asn Gly Lys Thr Ile Val Ala Ser Gln
            275                 280                 285
Asp Asp Arg Ala Val Pro Asp Tyr Ile Val Met Lys
            290                 295                 300

<210> SEQ ID NO 30
<211> LENGTH: 300
<212> TYPE: PRT
<213> ORGANISM: Lactococcus lactis subsp. lactis

<400> SEQUENCE: 30

Met Asn Gln Lys Lys Arg Arg His Tyr Arg Lys Lys His Thr Val
1               5                   10                  15
Leu Lys Val Ile Ser Ile Ile Phe Val Leu Val Ile Ile Ala Val Ala
            20                  25                  30
Ser Ile Ala Tyr Val Ala Tyr Arg Asn Val Glu Ser Thr Phe Ser Thr
            35                  40                  45
Ser Tyr Glu Asn Phe Pro Lys Thr Thr Ser Ile Asp Leu Lys Lys Ser
50                  55                  60
Lys Thr Phe Thr Thr Leu Ile Ile Ala Thr Gly Lys Asn Asn Ser Lys
65                  70                  75                  80
Asn Thr Ala Tyr Ala Thr Val Leu Ala Ser Thr Asn Val Lys Thr Asn
            85                  90                  95
Gln Thr Thr Phe Met Asn Phe Pro Val Phe Ala Thr Met Pro Asn Gln
            100                 105                 110
Lys Thr Ile Thr Glu Val Tyr Asn Thr Asn Gly Asp Asp Gly Ile Phe
            115                 120                 125
Gln Met Val Lys Asp Leu Leu Asn Val Ser Ile Asn Lys Val Ile Gln
            130                 135                 140
Ile Asp Val Asn Lys Met Gly Ser Leu Val Gln Ala Thr Gly Gly Ile
145                 150                 155                 160
Thr Met Gln Asn Pro Lys Ala Phe Asn Ala Glu Gly Tyr Glu Phe Lys
            165                 170                 175
```

```
Gln Gly Thr Val Asn Leu Gln Thr Ala Asp Gln Val Gln Ala Tyr Met
            180                 185                 190

Thr Gln Ile Asp Asp Thr Asp Leu Asp Ala Ser Ile Thr Arg Ile Gln
        195                 200                 205

Asn Val Ser Met Glu Leu Tyr Gly Asn Ile Gln Lys Val Ala His Met
        210                 215                 220

Lys Lys Leu Glu Ser Phe Asn Tyr Tyr Arg Glu Ile Leu Tyr Ala Phe
225                 230                 235                 240

Ser Asn Thr Val Lys Thr Asn Ile Ser Phe Asn Asp Ala Lys Thr Ile
                245                 250                 255

Val Met Ser Tyr Asn Lys Ala Leu Lys Asn Thr Gly Lys Leu Asn Leu
                260                 265                 270

His Thr Thr Asp Glu Asn Gly Ala Lys Val Val Ser Gln Thr Glu Leu
        275                 280                 285

Asp Ser Val Lys Thr Leu Phe Glu Lys Ser Leu Lys
290                 295                 300
```

EPS GENE CLUSTER OF TEXTURIZING LACTIC ACID BACTERIA

CROSS-REFERENCE TO RELATED APPLICATIONS

The present application is the U.S. National Stage of International Application PCT/EP2016/081724, filed Dec. 19, 2016, and claims priority to European Patent Application Nos. 15201995.6, filed Dec. 22, 2015, and 16170128.9, filed May 18, 2016.

FIELD OF THE INVENTION

The present invention relates to novel *Lactococcus lactis* subsp. *lactis* lactic acid bacterium strains, having improved texturizing properties. The present invention also relates to methods of using the strains for making food products.

BACKGROUND OF THE INVENTION

Lactic acid bacteria (LAB) are used extensively by the food industry for fermentation of food.

Conversion of fresh milk to fermented milk by LAB is a way of extending the life time of the milk and provides taste as well as texture.

Thus, important features of the strains used for milk fermentation include fast acidification, stable (no/low) post-acidification, long shelf-life and good texture. Good texture is typically high mouth thickness (measured as high shear stress using a rheometer) and high gel firmness.

Some LAB strains contribute significantly to an improved texture associated with their ability to produce exo- (or extracellular) polysaccharides (EPS), which can be capsular (remain attached to the cell in the form of capsules) or secreted into the media. EPS consists of either a single type of sugar or repeating units made of different sugars. EPS-producing LAB are of interest, since EPS act as natural viscosifiers and texture enhancers of fermented foods. Furthermore, EPS from food-grade LAB with defined rheological properties have potential for development and exploitation as food additives.

Fermented milk can be produced by mesophilic LAB, e.g. *Lactococcus* sp. leading to e.g. sour milk, or thermophilic LAB, e.g. *Streptococcus thermophilus* and *Lactobacillus delbruckii* subsp. *bulgaricus* for yoghurt.

Dairy products, such as fresh cheese, butter milk, sour milk and sour cream, prepared with mesophilic starter cultures, such as combinations of *Lactococcus lactis* subsp *lactis* strains and *Lactococcus lactis* subsp. *cremoris* strains, are in popular demand with consumers.

*Lactococcus* sp. strains generally produce low quantities of EPS.

It is expected to find more texturizing *Lactococcus lactis* subsp. *cremoris* strains than texturizing *Lactococcus lactis* subsp. *lactis* strains, since strains of the subsp. *cremoris* are more specialized to the milk environment, as they are often isolated from milk products, while strains of the subsp. *lactis* can be isolated from, e.g. plants.

Despite EPS production has been reported for some *L. lactis* subsp. *lactis* strains (Pan and Mei 2010, Suzuki et al 2013), the structure of their eps clusters have not been elucidated. Pan and Mei (2010) characterized EPS produced by *L. lactis* subsp. *lactis*, which was isolated from Chinese pickled cabbage, but it is not known if this strain is able to acidify milk and contribute to its texture. No eps genes were reported for this strain (Pan and Mei, 2010). Suzuki et al (2013) reported the sequences of a highly conserved epsD gene and a strain-specific epsE gene in five lactococcal strains, two from the subsp. *lactis* biovar diacetylactis and two from the subsp. *cremoris*. However, neither information on a complete eps gene cluster nor if the EPS produced by these strains is able to enhance milk texture is available. It is worth noticing that not all of the EPS-producing LAB strains are able to acidify milk, but also the ability of LAB strains to produce EPS does not ensure their enhanced texturing properties in milk, which are related to milk gel viscosity and ropiness. The type of EPS and their interaction with milk proteins is the determining factor for texture development. EPS can affect formation of casein gel structure by acting as filler. Thus the effect of EPS on protein matrix and structure formation depends on their concentration, interactions with the protein, and molecular and rheological characteristics. As an example, a production of yoghurt using EPS-producing *S. thermophilus, Lactobacillus casei* and *L. lactis* subsp. *lactis* has been reported (Ai et al, patent CN101331900). It is not clear how the viscosity has been measured, and what is the viscosity of milk fermented with non-EPS producing strains under the same conditions would be, which would indicate the basis level of fermented milk viscosity under the fermentation conditions used, but the viscosity of milk fermented with KS4 (*L. lactis* subsp. *lactis*) is the lowest in comparison with the milk fermented with the remaining strains tested, such as Tx (*S. thermophilus*), KL1 and J1 (*Lactobacillus casei*) (Table 4 of CN101331900). There seems to be a negative correlation between the amount of EPS produced by these strains (Table 3 of CN101331900) and the resulting milk viscosity (Table 4 of CN101331900). For instance, the *S. thermophilus* strain Tx produced the lowest amount of EPS, but resulted in milk with the highest viscosity, while the *L. lactis* subsp. *lactis* strain KS4 produced the highest amount of EPS, but resulted in milk with the lowest viscosity (Table 3 and Table 4 of CN101331900). These results confirm that the EPS structure and interaction with milk components is at least as important for the milk texture development as the amount of EPS produced. No information on the eps gene clusters has been reported for the strains mentioned (CN101331900).

None of the 13 *L. lactis* subsp. *lactis* strains, for which complete genomes or contigs or scaffolds were available in the NCBI database on Apr. 27, 2015, were reported as texturing (see Example 3 for details). Since mesophilic cultures are used for fermented milk products, and texture is an important parameter, there is a growing interest from the industry for texturizing mesophilic strains, e.g. *Lactococcus lactis* subsp. *lactis*.

SUMMARY OF THE INVENTION

It is an object of the present invention to provide novel texturizing lactic acid bacterium strains suitable for use in preparation of food products. In particular, it would be beneficial to provide texturizing *Lactococcus lactis* subsp *lactis* strains suitable for use in preparation of mesophilic food products.

This object has been solved with a texturizing *Lactococcus lactis* subsp. *lactis* strain comprising a novel eps gene cluster as described herein.

As discussed in working examples herein (see e.g. FIG. 1)—herein disclosed novel *lactococcus lactis* subsp. *lactis* CHCC11848 (deposited as DSM 29291) has excellent texturing properties.

The present inventors analyzed the eps gene cluster of CHCC11848 and identified novel gene sequences which are believed to be involved in the production of exopolysaccharide (EPS) and thereby involved in the creation of the excellent texturizing properties of *lactococcus lactis* subsp. *lactis* CHCC11848 strain.

The sequences as represented by SEQ ID NO: 8-13 and 16 disclosed herein are novel over the prior art.

Without being limited to theory there is no substantial reason to believe that it would not be plausible that another *lactococcus lactis* subsp. *lactis* strain (i.e. different from the specific CHCC11848 strain) that comprises eps gene cluster genes/sequences similar to the novel herein discussed characterizing eps gene cluster genes/sequences of the CHCC11848 strain, would not also have improved texturing properties.

Accordingly, a first aspect of the invention relates to a texturizing *Lactococcus lactis* subsp. *lactis* lactic acid bacterium strain comprising an active eps gene cluster capable of producing exopolysaccharide (EPS);

wherein the eps gene cluster is characterized by that it comprises at least one nucleotide sequence selected from the group consisting of:

(a): a nucleotide sequence encoding a polypeptide having polymerase activity and wherein the polypeptide has at least 70% identity with the amino acid sequence encoded by the nucleotide sequence of SEQ ID NO:9 (herein termed wzy);

(b): a nucleotide sequence encoding a polypeptide having polysaccharide transporter activity and wherein the polypeptide has at least 80% identity with the amino acid sequence encoded by the nucleotide sequence of SEQ ID NO:12 (herein termed wzx); and (c): at least one a nucleotide sequence encoding a polypeptide having glycosyltransferase (GT) activity selected from the group consisting of:

(c1): the polypeptide has at least 70% identity with the amino acid sequence encoded by the nucleotide sequence of SEQ ID NO:8 (herein termed GT1);

(c2): the polypeptide has at least 70% identity with the amino acid sequence encoded by the nucleotide sequence of SEQ ID NO:10 (herein termed GT2); and (c3): the polypeptide has at least 70% identity with the amino acid sequence encoded by the nucleotide sequence of SEQ ID NO:11 (herein termed GT3).

As discussed herein—SEQ ID NO:16 sets out the 7097-bp nucleotide sequence of the variable part of the eps cluster of CHCC11848 corresponding to nucleotide 4171 to 11267 of SEQ ID NO:1.

The SEQ ID numbers of the first aspect are all present in the variable part (i.e. SEQ ID NO:16) of the eps cluster of CHCC11848.

In relation to lactic acid bacterium strain the term "exopolysaccharide (EPS)" is well known and the skilled person can routinely determine if a lactic acid bacterium of interest produces EPS.

As known and understood by the skilled person a lactic acid bacterium of interest, which produces EPS, will comprise an active eps gene cluster.

As known to the skilled person an active eps gene cluster comprises genes involved in regulation and modulation of EPS biosynthesis and genes involved in the biosynthesis of an oligosaccharide repeat unit and export, including a glycosyltransferase (GT), a polymerase and a transporter.

In short and as understood by the skilled person, since the lactic acid bacterium strain of the first aspect is capable of producing and exporting exopolysaccharide (EPS) then it will comprise an active eps gene cluster.

In relation to item (a) of the first aspect, it is routine work for the skilled person to determine if a polypeptide of interest has the required polymerase activity.

At the filing date of the present application and in relation to SEQ ID NO:9—the present inventors believed that the closest prior art published functional similar sequence had less than 45% identify to SEQ ID NO:9.

In relation to item (b) of the first aspect—it is routine work for the skilled person to determine if a polypeptide of interest has the required polysaccharide transporter activity. At the filing date of the present application and in relation to SEQ ID NO:12—the present inventors believed that the closest prior art published functional similar sequence had less than 75% identify to SEQ ID NO:12.

In relation to item (b) of the first aspect—the polypeptide having polysaccharide transporter activity may alternatively be referred to as a polypeptide having polysaccharide export activity.

In relation to item (c) of the first aspect—it is routine work for the skilled person to determine if a polypeptide of interest has the required glycosyltransferase (GT) activity.

At the filing date of the present application and in relation to SEQ ID NO:8—the present inventors believed that the closest prior art published functional similar sequence had less than 55% identify to SEQ ID NO:8.

At the filing date of the present application and in relation to SEQ ID NO:10—the present inventors believed that the closest prior art published functional similar sequence had less than 50% identify to SEQ ID NO:10.

At the filing date of the present application and in relation to SEQ ID NO:11—the present inventors believed that the closest prior art published functional similar sequence had less than 55% identify to SEQ ID NO:11.

A second aspect of the invention relates to a method of producing a food product comprising at least one stage in which at least one lactic acid bacterium strain according to the first aspect or any herein discussed embodiments thereof is used.

DEFINITIONS

All definitions of herein relevant terms are in accordance of what would be understood by the skilled person in relation to the herein relevant technical context.

By "texturizing strain" in the present specification and claims is meant a strain which preferably generates fermented milks having under the conditions described below and as exemplified in Example 1 herein, a shear stress preferably greater than 40 Pa measured at shear rate 300 $s^{-1}$.

A strain of *Lactococcus lactis* subsp. *lactis* can be defined as strongly texturizing in that it generates fermented milks having, under the same conditions, a shear stress greater than 50 Pa measured at shear rate 300 $s^{-1}$.

The texturizing lactic acid bacterium strain of the invention may be an isolated strain, e.g., isolated from a naturally occurring source, or may be a non-naturally occurring strain, e.g. made recombinantly. Recombinant strains will differ from naturally occurring strains by at least the presence of the nucleic acid construct(s) used to transform or transfect the mother strain.

The term "Sequence Identity" relates to the relatedness between two nucleotide sequences or between two amino acid sequences.

For purposes of the present invention, the degree of sequence identity between two nucleotide sequences or two amino acid sequences is determined using the sequence alignment method of ClustalW version 2 (ClustalW2) for nucleotide sequence (DNA) or amino acid sequence (protein), respectively, pairwise alignment as described by Larkin et al. (2007, Bioinformatics 23:2947-2948) and Goujon et al. (2010, Nucleic acids research 38 Suppl:W695-699) with default parameters (Alignment Type: Slow; DNA Weight Matrix: IUB; Protein Weight Matrix: Gonnet; Gap Open: 10; Gap Extension: 0.1), available through CLC software.

In the present context, the terms "strains derived from" and "derived strain" should be understood as a strain derived from a strain of the invention by means of e.g. genetic engineering, radiation and/or chemical treatment, and/or selection, adaptation, screening, etc. It is preferred that the derived strain is a functionally equivalent mutant, e.g. a strain that has substantially the same, or improved, properties with respect to texturizing capacity as the mother strain. Such a derived strain is a part of the present invention. Especially, the term "derived strain" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, no more than 10, or no more than 5, treatments are carried out. In a presently preferred derived strain, less than 1%, or less than 0.1%, less than 0.01%, less than 0.001% or even less than 0.0001% of the nucleotides in the bacterial genome have been changed (such as by replacement, insertion, deletion or a combination thereof) compared to the mother strain.

The term "thermophilic" herein refers to microorganisms that thrive best at temperatures above 35° C. The industrially most useful thermophilic bacteria include *Streptococcus* spp. and *Lactobacillus* spp. The term "thermophilic fermentation" herein refers to fermentation at a temperature above about 35° C., such as between about 35° C. to about 45° C. The term "thermophilic fermented milk product" refers to fermented milk products prepared by thermophilic fermentation of a thermophilic starter culture and include such fermented milk products as set-yoghurt, stirred-yoghurt and drinking yoghurt, e.g. Yakult.

The term "mesophilic" herein refers to microorganisms that thrive best at moderate temperatures (15° C.-35° C.). The industrially most useful mesophilic bacteria include *Lactococcus* spp. and *Leuconostoc* spp. The term "mesophilic fermentation" herein refers to fermentation at a temperature between about 22° C. and about 35° C. The term "mesophilic food products" refers to food products prepared by mesophilic fermentation of a mesophilic starter culture. The term "mesophilic fermented milk product" refers to fermented milk products prepared by mesophilic fermentation of a mesophilic starter culture and include such fermented milk products as buttermilk, sour milk, cultured milk, smetana, sour cream, Kefir and fresh cheese, such as quark, tvarog and cream cheese.

The term "mesophilic starter culture" herein refers to any starter cultures culture containing at least one mesophiulic bacterium strain. Mesophilic starter cultures, such as combinations of *Lactococcus lactis* subsp *lactis* strains and *Lactococcus lactis* subsp. *cremoris* strains, are used to produce fermented milk products, such as fresh cheese, butter milk, sour milk and sour cream.

The terms "fermented milk" and "dairy" are used interchangeably herein.

The terms "a" and "an" and "the" and similar referents as used in the context of describing the invention are to be construed to cover both the singular and the plural, unless otherwise indicated herein or clearly contradicted by context. Thus, "a" and "an" and "the" may mean at least one, or one or more.

In connection with the present invention, shear stress may be measured by the following method:

The day after incubation, the fermented milk product was brought to 13° C. and manually stirred gently by means of a stick fitted with a perforated disc until homogeneity of the sample. The rheological properties of the sample were assessed on a rheometer (Anton Paar Physica Rheometer with ASC, Automatic Sample Changer, Anton Paar® GmbH, Austria) by using a bob-cup. The rheometer was set to a constant temperature of 13° C. during the time of measurement. Settings were as follows:

Holding Time (to Rebuild to Somewhat Original Structure)

5 minutes without any physical stress (oscillation or rotation) applied to the sample.

Oscillation step (to measure the elastic and viscous modulus, G' and G", respectively, therefore calculating the complex modulus G*)

Constant strain=0.3%, frequency (f)=[0.5 . . . 8] Hz 6 measuring points over 60 s (one every 10 s)

Rotation step (to measure shear stress at 300 1/s)

Two steps were designed:

Shear rate=[0.3-300] 1/s and 2) Shear rate=[275-0.3] 1/s.

Each step contained 21 measuring points over 210 s (on every 10 s).

The shear stress at 300 1/s was chosen for further analysis, as this correlates to mouth thickness when swallowing a fermented milk product.

Alternatively, the shear stress may be measured by the following method: Shear stress data were obtained by inoculating the same microbial cultures in semi-fat milk (1.5% fat) enriched with 2% skim milk powder; milk was heated at 90° C. for 20 min and cooled down to the inoculation temperature, prior to inoculation with 1% overnight microbial culture. The inoculation took place for 12-15 h at 30° C. in 200-ml scale until pH~4.55 followed by cooling to 4° C. and storage for 5 days at 4° C. After the storage, the fermented milk was stirred gently by means of a stick fitted with a bored disc until homogeneity of the sample. Shear stress of the samples was assessed on a rheometer (Anton Paar Physica Rheometer with ASC, Automatic Sample Changer, Anton Paar® GmbH, Austria) using the following settings:

Wait time (to rebuild to somewhat original structure)

5 minutes without oscillation or rotation

Rotation (to measure shear stress at 300 $s^{-1}$ etc.)

Y'=[0.2707-300] $s^{-1}$ and y'=[275-0.2707] $s^{-1}$ 21 measuring points over 210 s (on every 10 s) going up to 300 $s^{-1}$ and 21 measuring points over 210 s (one every 10 s) going down to 0.2707 $s^{-1}$ For the data analysis, the shear stress at shear rate 300 $s^{-1}$ was chosen.

BRIEF DESCRIPTION OF THE FIGURES

FIG. 3C shows the percent identity matrix of the eps clusters depicted on FIGS. 2 and 3 A on the nucleotide level.

BRIEF DESCRIPTION OF THE SEQUENCE LISTING

Figure 1:
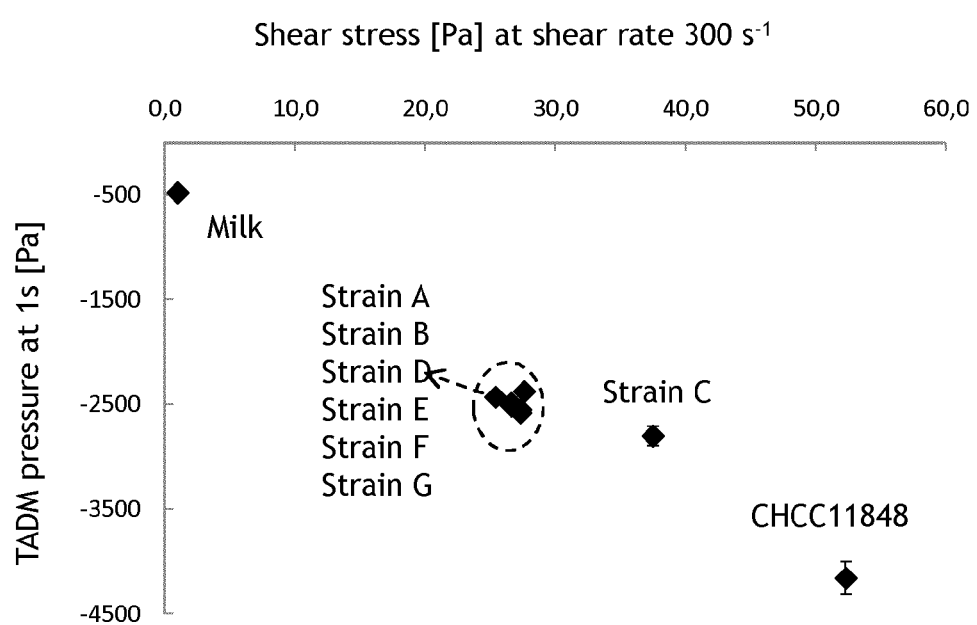
FIG. 1 illustrates TADM (pressure curve derived results) and rheometer data for selected *L. lactis* subsp. *lactis* strains from Chr. Hansen's strain collection. No eps cluster was found in the genome of Strain G, thus this strain is not shown on FIGS. 2-3. TADM data were obtained from 1-ml samples made in micro-titer plates, which were inoculated for 20 hours at 30° C.; thus the sample end pH varies (pH≤4.55), depending on how fast different strains are in acidifying milk. Hamilton liquid handling unit was used to measure pressure during aspiration and dispense (TADM). Shear stress data were obtained by inoculating strains in 200-ml scale until they reach pH~4.55 followed by rheological measurements using a rheometer. "Milk" refers to B-milk, which was not inoculated with any strain.

SEQ ID NO:1 sets out the 13097-bp nucleotide sequence of the EPS cluster of CHCC11848.

SEQ ID NO:2 sets out the open reading frame (ORF) of the epsR gene corresponding to nucleotides 1 to 318 of SEQ ID NO:1.

SEQ ID NO:3 sets out the ORF of the epsX gene corresponding to nucleotides 352 to 1119 of SEQ ID NO:1.

SEQ ID NO:4 sets out the ORF of the epsA gene corresponding to nucleotides 1159 to 1938 of SEQ ID NO:1.

SEQ ID NO:5 sets out the ORF of the epsB gene corresponding to nucleotides 1948 to 2643 of SEQ ID NO:1.

SEQ ID NO:6 sets out the ORF of the epsC gene corresponding to nucleotides 2698 to 3462 of SEQ ID NO:1.

SEQ ID NO:7 sets out the ORF of the epsD gene corresponding to nucleotides 3484 to 4170 of SEQ ID NO:1.

SEQ ID NO:8 sets out the ORF coding a putative GT1 protein corresponding to nucleotides 4177 to 5298 of SEQ ID NO:1 and to nucleotides 7 to 1128 of SEQ ID NO:16.

SEQ ID NO:9 sets out the ORF of a putative wzy gene corresponding to nucleotides 5562 to 6665 of SEQ ID NO:1 and to nucleotides 1392 to 2495 of SEQ ID NO:16.

SEQ ID NO:10 sets out the ORF coding a putative GT2 protein corresponding to nucleotides 6686 to 7561 of SEQ ID NO:1 and to nucleotides 2516 to 3391 of SEQ ID NO:16.

SEQ ID NO:11 sets out the ORF coding a putative GT3 protein corresponding to nucleotides 7558 to 8454 of SEQ ID NO:1 and to nucleotides 3388 to 4284 of SEQ ID NO:16.

SEQ ID NO:12 sets out the ORF of a putative wzx gene corresponding to nucleotides 8605 to 10026 of SEQ ID NO:1 and to nucleotides 4435 to 5856 of SEQ ID NO:16.

SEQ ID NO:13 sets out the ORF of a putative ugd gene corresponding to nucleotides 10080 to 11246 of SEQ ID NO:1 and to nucleotides 5910 to 7076 of SEQ ID NO:16.

SEQ ID NO: 14 sets out the ORF of the epsL gene corresponding to nucleotides 11268 to 12170 of SEQ ID NO:1.

SEQ ID NO: 15 sets out the nucleotide sequence, corresponding to nucleotides 12195 to 1397 of SEQ ID NO:1, of the complementary strand to the ORF of the orfY gene.

SEQ ID NO:16 sets out the 7097-bp nucleotide sequence of the variable part of the eps cluster of CHCC11848 corresponding to nucleotide 4171 to 11267 of SEQ ID No.1.

SEQ ID NO:17 sets out the amino acid sequence encoded by SEQ ID NO:2.

SEQ ID NO:18 sets out the amino acid sequence encoded by SEQ ID NO:3.

SEQ ID NO:19 sets out the amino acid sequence encoded by SEQ ID NO:4.

SEQ ID NO:20 sets out the amino acid sequence encoded by SEQ ID NO:5.

SEQ ID NO:21 sets out the amino acid sequence encoded by SEQ ID NO:6.

SEQ ID NO:22 sets out the amino acid sequence encoded by SEQ ID NO:7.

SEQ ID NO:23 sets out the amino acid sequence encoded by SEQ ID NO:8.

SEQ ID NO:24 sets out the amino acid sequence encoded by SEQ ID NO:9.

SEQ ID NO:25 sets out the amino acid sequence encoded by SEQ ID NO:10.

SEQ ID NO:26 sets out the amino acid sequence encoded by SEQ ID NO:11.

SEQ ID NO:27 sets out the amino acid sequence encoded by SEQ ID NO:12.

SEQ ID NO:28 sets out the amino acid sequence encoded by SEQ ID NO:13.

SEQ ID NO:29 sets out the amino acid sequence encoded by SEQ ID NO:14.

SEQ ID NO:30 sets out the amino acid sequence encoded by the complementary strand of SEQ ID NO:15.

DETAILED DESCRIPTION OF THE INVENTION

A Texturizing *Lactococcus lactis* Subsp. *Lactis* Lactic Acid Bacterium Strain

As discussed above, a first aspect of the invention relates to a texturizing *Lactococcus lactis* subsp. *lactis* lactic acid bacterium strain comprising an active eps gene cluster capable of producing exopolysaccharide (EPS);

wherein the eps gene cluster is characterized by that it comprises at least one nucleotide sequence selected from the group consisting of:

(a): a nucleotide sequence encoding a polypeptide having polymerase activity and wherein the polypeptide has at least 70% identity with the amino acid sequence encoded by the nucleotide sequence of SEQ ID NO:9 (herein termed wzy);

(b): a nucleotide sequence encoding a polypeptide having polysaccharide transporter activity and wherein the polypeptide has at least 80% identity with the amino acid sequence encoded by the nucleotide sequence of SEQ ID NO:12 (herein termed wzx); and (c): at least one a nucleotide sequence encoding a polypeptide having glycosyltransferase (GT) activity selected from the group consisting of:

(c1): the polypeptide has at least 70% identity with the amino acid sequence encoded by the nucleotide sequence of SEQ ID NO:8 (herein termed GT1);

(c2): the polypeptide has at least 70% identity with the amino acid sequence encoded by the nucleotide sequence of SEQ ID NO:10 (herein termed GT2); and (c3): the polypeptide has at least 70% identity with the amino acid sequence encoded by the nucleotide sequence of SEQ ID NO:11 (herein termed GT3).

Preferably, the texturizing lactic acid bacterium of the first aspect is a LAB, wherein (a): the nucleotide sequence encoding a polypeptide having polymerase activity has at least 80% identity with the amino acid sequence encoded by the nucleotide sequence of SEQ ID NO:9 (herein termed wzy);

(b): the nucleotide sequence encoding a polypeptide having polysaccharide transporter activity has at least 85% identity with the amino acid sequence encoded by the nucleotide sequence of SEQ ID NO:12 (herein termed wzx);

(c): the nucleotide sequence encoding a polypeptide having glycosyltransferase (GT):

(c1): has at least 80% identity with the amino acid sequence encoded by the nucleotide sequence of SEQ ID NO:8 (herein termed GT1);

(c2): has at least 80% identity with the amino acid sequence encoded by the nucleotide sequence of SEQ ID NO:10 (herein termed GT2); and (c3): has at least 80% identity with the amino acid sequence encoded by the nucleotide sequence of SEQ ID NO:11 (herein termed GT3).

Preferably, the texturizing lactic acid bacterium of the first aspect is a LAB, wherein (a): the nucleotide sequence encoding a polypeptide having polymerase activity has at least 95% identity with the amino acid sequence encoded by the nucleotide sequence of SEQ ID NO:9 (herein termed wzy);

(b): the nucleotide sequence encoding a polypeptide having polysaccharide transporter activity has at least 95% identity with the amino acid sequence encoded by the nucleotide sequence of SEQ ID NO:12 (herein termed wzx);

(c): the nucleotide sequence encoding a polypeptide having glycosyltransferase (GT):

(c1): has at least 95% identity with the amino acid sequence encoded by the nucleotide sequence of SEQ ID NO:8 (herein termed GT1);

(c2): has at least 95% identity with the amino acid sequence encoded by the nucleotide sequence of SEQ ID NO:10 (herein termed GT2); and (c3): has at least 95% identity with the amino acid sequence encoded by the nucleotide sequence of SEQ ID NO:11 (herein termed GT3).

Preferably, the texturizing lactic acid bacterium of the first aspect is a LAB, wherein (a): the nucleotide sequence encoding a polypeptide having polymerase activity has at least 80% identity (preferably at least 85% identity, more preferably at least 90% identity, more preferably at least 95% identity, more preferably at least 98% identity, most preferably at least 100% identity) with the amino acid sequence encoded by the nucleotide sequence of SEQ ID NO:9 (herein termed wzy).

Preferably, the texturizing lactic acid bacterium of the first aspect is a LAB, wherein (b): the nucleotide sequence encoding a polypeptide having polysaccharide transporter activity has at least 85% identity (preferably at least 90% identity, more preferably at least 95% identity, more preferably at least 98% identity, most preferably at least 100% identity) with the amino acid sequence encoded by the nucleotide sequence of SEQ ID NO:12 (herein termed wzx).

Preferably, the texturizing lactic acid bacterium of the first aspect is a LAB, wherein (c): the nucleotide sequence encoding a polypeptide having glycosyltransferase (GT):

(c1): has at least 80% identity (preferably at least 85% identity, more preferably at least 90% identity, more preferably at least 95% identity, more preferably at least 98% identity, most preferably at least 100% identity) with the amino acid sequence encoded by the nucleotide sequence of SEQ ID NO:8 (herein termed GT1).

Preferably, the texturizing lactic acid bacterium of the first aspect is a LAB, wherein (c): the nucleotide sequence encoding a polypeptide having glycosyltransferase (GT):

(c2): has at least 80% identity (preferably at least 85% identity, more preferably at least 90% identity, more preferably at least 95% identity, more preferably at least 98% identity, most preferably at least 100% identity) with the amino acid sequence encoded by the nucleotide sequence of SEQ ID NO:10 (herein termed GT2).

Preferably, the texturizing lactic acid bacterium of the first aspect is a LAB, wherein (c): the nucleotide sequence encoding a polypeptide having glycosyltransferase (GT):

(c3): has at least 80% identity (preferably at least 85% identity, more preferably at least 90% identity, more preferably at least 95% identity, more preferably at least 98% identity, most preferably at least 100% identity) with the amino acid sequence encoded by the nucleotide sequence of SEQ ID NO:11 (herein termed GT3).

Preferably, the texturizing lactic acid bacterium comprises more than one of the nucleotide sequences specified in the first aspect.

Accordingly, preferably the texturizing lactic acid bacterium of the first aspect and herein described embodiments thereof (i.e. the texturizing lactic acid bacterium as described herein) is a LAB, wherein the eps gene cluster comprises at least:

(a): the nucleotide sequence encoding a polypeptide having polymerase activity of item (a) of the first aspect and herein described embodiments thereof; and (c): at least one (preferably at least two and more preferably at least three) of the nucleotide sequences encoding a polypeptide having glycosyltransferase (GT) activity of item (c) of the first aspect and herein described embodiments thereof.

Preferably, the texturizing lactic acid bacterium of the invention comprises at least one nucleotide sequence selected from the group consisting of:

(a): a nucleotide sequence encoding a polypeptide having polymerase activity and wherein the polypeptide has at least 70%, preferably at least 80%, more preferably 95%, identity with the amino acid sequence encoded by the nucleotide sequence of SEQ ID NO:9 (herein termed wzy); and (c): at least one a nucleotide sequence encoding a polypeptide having glycosyltransferase (GT) activity selected from the group consisting of:

(c1): the polypeptide has at least 70%, preferably at least 80%, more preferably 95%, identity with the amino acid sequence encoded by the nucleotide sequence of SEQ ID NO:8 (herein termed GT1);

(c2): the polypeptide has at least 70%, preferably at least 80%, more preferably 95%, identity with the amino acid sequence encoded by the nucleotide sequence of SEQ ID NO:10 (herein termed GT2); and (c3): the polypeptide has at least 70%, preferably at least 80%, more preferably 95%, identity with the amino acid sequence encoded by the nucleotide sequence of SEQ ID NO:11 (herein termed GT3).

Preferably, the texturizing lactic acid bacterium of the invention comprises at least one nucleotide sequence selected from the group consisting of:

(a): a nucleotide sequence encoding a polypeptide having polymerase activity and wherein the polypeptide has at least 70% identity with the amino acid sequence encoded by the nucleotide sequence of SEQ ID NO:9 (herein termed wzy); and (c): at least one a nucleotide sequence encoding a polypeptide having glycosyltransferase (GT) activity selected from the group consisting of:

(c1): the polypeptide has at least 70% identity with the amino acid sequence encoded by the nucleotide sequence of SEQ ID NO:8 (herein termed GT1);

(c2): the polypeptide has at least 70% identity with the amino acid sequence encoded by the nucleotide sequence of SEQ ID NO:10 (herein termed GT2); and (c3): the polypeptide has at least 70% identity with the amino acid sequence encoded by the nucleotide sequence of SEQ ID NO:11 (herein termed GT3).

Preferably, the texturizing lactic acid bacterium of the invention comprises at least one nucleotide sequence selected from the group consisting of:

(a): a nucleotide sequence encoding a polypeptide having polymerase activity and wherein the polypeptide has at least 80% identity with the amino acid sequence encoded by the nucleotide sequence of SEQ ID NO:9 (herein termed wzy); and (c): at least one a nucleotide sequence encoding a polypeptide having glycosyltransferase (GT) activity selected from the group consisting of:

(c1): the polypeptide has at least 80% identity with the amino acid sequence encoded by the nucleotide sequence of SEQ ID NO:8 (herein termed GT1);

(c2): the polypeptide has at least 80% identity with the amino acid sequence encoded by the nucleotide sequence of SEQ ID NO:10 (herein termed GT2); and (c3): the polypeptide has at least 80% identity with the amino acid sequence encoded by the nucleotide sequence of SEQ ID NO:11 (herein termed GT3).

Preferably, the texturizing lactic acid bacterium of the invention comprises at least one nucleotide sequence selected from the group consisting of:

(a): a nucleotide sequence encoding a polypeptide having polymerase activity and wherein the polypeptide has at least 95% identity with the amino acid sequence encoded by the nucleotide sequence of SEQ ID NO:9 (herein termed wzy); and (c): at least one a nucleotide sequence encoding a polypeptide having glycosyltransferase (GT) activity selected from the group consisting of:

(c1): the polypeptide has at least 95% identity with the amino acid sequence encoded by the nucleotide sequence of SEQ ID NO:8 (herein termed GT1);

(c2): the polypeptide has at least 95% identity with the amino acid sequence encoded by the nucleotide sequence of SEQ ID NO:10 (herein termed GT2); and (c3): the polypeptide has at least 95% identity with the amino acid sequence encoded by the nucleotide sequence of SEQ ID NO:11 (herein termed GT3).

Preferably, the texturizing lactic acid bacterium of the first aspect and herein described embodiments thereof is a LAB, wherein the eps gene cluster comprises the following nucleotide sequences:

(a): a nucleotide sequence encoding a polypeptide having polymerase activity and wherein the polypeptide has at least 70% identity (preferably at least 85% identity, more preferably at least 90% identity) with the amino acid sequence encoded by the nucleotide sequence of SEQ ID NO:9 (herein termed wzy); and (b): a nucleotide sequence encoding a polypeptide having polysaccharide transporter activity and wherein the polypeptide has at least 80% identity (preferably at least 90% identity) with the amino acid sequence encoded by the nucleotide sequence of SEQ ID NO:12 (herein termed wzx); and (c): a nucleotide sequence encoding a polypeptide having glycosyltransferase (GT) activity selected from the group consisting of:

(c1): the polypeptide has at least 70% identity (preferably at least 85% identity, more preferably at least 90% identity) with the amino acid sequence encoded by the nucleotide sequence of SEQ ID NO:8 (herein termed GT1);

(c2): the polypeptide has at least 70% identity (preferably at least 85% identity, more preferably at least 90% identity) with the amino acid sequence encoded by the nucleotide sequence of SEQ ID NO:10 (herein termed GT2); and (c3): the polypeptide has at least 70% identity (preferably at least 85% identity, more preferably at least 90% identity) with the amino acid sequence encoded by the nucleotide sequence of SEQ ID NO:11 (herein termed GT3).

In relation to the embodiment immediately above, it is preferred that the eps gene cluster comprises:

(c): the three nucleotide sequences encoding a polypeptide having glycosyltransferase (GT) activity of item (c) of the embodiment immediately above.

As discussed herein—SEQ ID NO:16 sets out the 7097-bp nucleotide sequence of the variable part of the eps cluster of CHCC11848 corresponding to nucleotide 4171 to 11267 of SEQ ID NO:1.

In a preferred embodiment, the texturizing lactic acid bacterium strain as described herein is a LAB, wherein the eps gene cluster comprises:

(d): a nucleotide sequence having at least 85% identity (preferably at least 90% identity and more preferably at least 95% identity) with the nucleotide sequence of SEQ ID NO:16 (herein termed the variable part of the eps cluster of CHCC11848).

In a preferred embodiment, the texturizing lactic acid bacterium strain as described herein is a LAB, wherein the eps gene cluster comprises:

(d): a nucleotide sequence having at least 85% identity (preferably at least 90% identity and more preferably at least 95% identity) with the nucleotide sequence of SEQ ID NO:1 (herein termed the eps cluster of CHCC11848).

As discussed in working examples herein (see e.g. FIG. 1)—herein disclosed novel *lactococcus lactis* subsp. *lactis* CHCC11848 (deposited as DSM 29291) has excellent texturing properties.

Preferably, the texturizing lactic acid bacterium strain as described herein is a LAB, wherein the texturizing lactic acid bacterium strain is a strain which generates fermented milks having a shear stress greater than 40 Pa, more preferably 41 Pa, more preferably 42 Pa, more preferably 43 Pa, more preferably 44 Pa, more preferably 45 Pa, more preferably 46 Pa, more preferably 47 Pa, more preferably 48 Pa, more preferably 49 Pa, and most preferably 50 Pa, measured at shear rate 300 $s^{-1}$, measured under following conditions: 200 ml semi-fat milk (1.5% fat) enriched with 2 g skim milk powder is heated to 90° C. for 20 min, followed by cooling to inoculation temperature, and inoculated with 2 ml of an overnight culture of the lactic acid bacterium strain, and left at inoculation temperature until pH 4.55 followed by storage at 4° C. for 5 days, followed by gently stirring and measuring the shear stress at shear rate 300 $s^{-1}$, wherein the inoculation temperature is 30° C. The shear stress is measured using the method indicated in Example 1.

The present invention also relates to a *Lactococcus lactis* subsp. *lactis* strain selected from the group consisting of the strain deposited with DSMZ-Deutsche Sammlung von Mikroorganismen and Zellkulturen GmbH, Inhoffenstr. 7B, D-38124 Braunschweig, on Aug. 21, 2014 under the accession no. DSM 29291 and strains derived from DSM 29291, wherein the derived strain is characterized as having at least the same texturizing capability as DSM 29291.

In the present context, the term "derived strain" should be understood as a strain derived from a mother strain by means of e.g. genetic engineering, radiation and/or chemical treatment, and/or selection, adaptation, screening, etc. In specific embodiments the derived strain is a functionally equivalent mutant, e.g. a mutant that has substantially the same, or improved, properties (e.g. regarding texture) as the mother strain. Such a derived strain is part of the present invention. The term "derived strain" includes a strain obtained by subjecting a strain of the invention to any mutagenization treatment including treatment with a chemical mutagen such as ethane methane sulphonate (EMS) or N-methyl-N'-nitro-N-nitroguanidine (NTG), UV light or to a spontaneously occurring mutant. A derived strain may have been subjected to several mutagenization treatments (a single treatment should be understood one mutagenization step followed by a screening/selection step), but typically no more than 20, no more than 10, or no more than 5, treatments are carried out.

In specific embodiments of derived strains, less than 1%, or less than 0.1%, less than 0.01%, less than 0.001% or even less than 0.0001% of the nucleotides in the bacterial genome have been changed (such as by replacement, insertion, deletion or a combination thereof) compared to the mother strain.

Composition Comprising a LAB of the Invention:

The invention also relates to a composition comprising at least one lactic acid bacterium strain according to the invention.

In a specific embodiment the composition comprises at least $1 \times 10^6$ CFU (cell forming units)/ml of the at least one lactic acid bacterium strain according to the invention. It may be preferred that the composition comprises at least $1 \times 10^8$ CFU (cell forming units)/ml of the at least one lactic acid bacterium strain according to the invention.

Method of Producing a Food Product:

The present invention further relates to a method of producing a food product comprising at least one stage in which at least one lactic acid bacterium strain according to the invention is used.

It is evident that a composition comprising at least one lactic acid bacterium strain according to the invention may be used.

In specific embodiments the food product is a dairy product and the method comprises fermenting a milk substrate with the at least one lactic acid bacterium strain according the invention.

Preferably, the method comprises fermenting a milk substrate with a composition comprising at least $1 \times 10^6$ CFU (preferably at least $1 \times 10^8$ CFU) (cell forming units)/ml of the at least one lactic acid bacterium strain according to the invention.

In some embodiments, the food product has an improved texture as compared to a comparable composition without the strain.

The invention also relates to a food product comprising at least one lactic acid bacterium strain according to the invention.

In a specific embodiment the food product is a dairy product, a meat product, a vegetable product, a fruit product or a cereal product. In specific embodiments, the food product is a dairy product.

The term "dairy product" as used herein refers to a food product produced from milk. In the context of the present application, the term "milk" is broadly used in its common meaning to refer to liquids produced by the mammary glands of animals or by plants. In accordance with the present invention the milk may have been processed and the term "milk" includes whole milk, skim milk, fat-free milk, low fat milk, full fat milk, lactose-reduced milk, or concentrated milk. Fat-free milk is non-fat or skim milk product. Low-fat milk is typically defined as milk that contains from about 1% to about 2% fat. Full fat milk often contains 2% fat or more. The term "milk" is intended to encompass milks from different mammals and plant sources. Mammal sources of milk include, but are not limited to cow, sheep, goat, buffalo, camel, llama, mare and deer. Plant sources of milk include, but are not limited to, milk extracted from soy bean, pea, peanut, barley, rice, oat, *quinoa*, almond, cashew, coconut, hazelnut, hemp, sesame seed and sunflower seed. In a specific embodiment, the milk is cow's milk.

As typical dairy products according to the invention there can be mentioned a fermented milk product and cheese.

In a specific embodiment the dairy product is a mesophilic dairy product.

The production of the dairy product is carried out by methods known to the person skilled in the field, and in particular involves the fermentation of milk by at least one strain according to the invention.

Discussion of Eps Gene Cluster of CHCC11848:

Only about 1% of ~1000 *Lactococcus lactis* strains from the Chr. Hansen culture collection were found to enhance the texture of fermented milk, as shown by TADM (total aspiration and dispense monitoring)-based screening using a Hamilton liquid handling unit in 1-ml scale followed by confirmatory rheology assays in 200-ml scale. Most of the texturizing strains were of the subsp. *cremoris* and had similar eps clusters to those from the published *Lactococcus lactis* subsp. *cremoris* strains. However, one of the texturizing strains, CHCC11848, was of the subsp. *lactis* and was found to have a unique eps cluster. The eps cluster of CHCC11848 was found to be unique, as it was found to contain novel glycosyltransferases and other genes likely involved in the modification of the oligosaccharide unit, and the EPS as a product of this clusters is likely to contribute to the enhanced texturing properties of this strain in milk. The eps cluster of CHCC11848 is likely being chromosome-associated, as the eps cluster-containing contig of CHCC11848 was above 414 Kbp, which is approximately 10 times larger than a typical lactococcal plasmid. Lactococcal plasmids found up-to-date are between 1.6 and 80.6 Kbp in size. Moreover, the content of the eps-cluster-containing contig of CHCC11848 was found to be highly similar to the chromosome-associated genetic content of several publicly available *L. lactis* subsp. *lactis* strains, e.g. KF147 and KLDS 4.0325. It is believed that the eps cluster of CHCC11848 is unique in being chromosome-associated as opposed to plasmid-associated. Also, a strain containing a chromosome-associated eps cluster has the advantage over a strain containing a plasmid-associated eps cluster that it has a much more stable EPS producing property, because a plasmid is easily lost from a bacterium cell as opposed to chromosomal genes. In particular, a strain containing a chromosome-associated eps cluster provides a more stable mother strain for use as a basis for developing mutant strains.

The genetic loci for polysaccharide biosynthesis by the Wzy-dependent mechanism are similar in all bacteria and are well studied in *S. pneumonia*. Genetic analysis of the CPS locus from 90 pneumococcal serotypes demonstrated a striking feature of the polysaccharide operon: the presence of many highly divergent forms of each of the key enzyme classes. Thus, there were found 40 homology groups for polysaccharide polymerases, 13 groups of lipases, and a great diversity of glycosyltransferases. The presence of multiple non-homologous or highly divergent forms of these enzymes, together with often different G+C content of the region in which these are encoded, supports the view that these genes have been imported on multiple occasions from different and unknown sources. Many eps gene clusters have undergone rearrangement mediated by insertion sequence (IS) elements and received genes from other organisms by a horizontal gene transfer. Typical of eps operon organization is the presence of IS elements flanking or within the operon. The plethora of glycosyltransferases observed in the loci for polysaccharide production provides an opportunity to continually generate new strains producing unique EPS by gene shuffling. As EPS show an enormous diversity in monosaccharide building blocks, anomeric configuration, conformation, and stereochemistry, the resulting diversity of EPS structures is uncanny: for instance, two glucose residues can be joined together in 30 different ways. According to Carbohydrate-Active enZymes (CAZy) database (cazy.org), glycosyltransferases are currently classified into 97 families (June 2015), which can help in predicting their mode of action. Nevertheless, this does not mean that all enzymes of a family recognize the same donor and acceptor, as poly-specificity is common among glycosyltransferase families, and thus one should be prudent with the over-interpretation of predictions based purely on this classification. In most cases, the factors determining the specificity of glycosyltransferases remain elusive, and it is difficult to predict their mode of action based merely on sequence analysis. Thus, a crucial area for further research is the search for factors or motifs determining the substrate specificity of glycosyltransferases, both in the glycosyltransferases and in the substrates. A complicating aspect, however, is that some glycosyltransferases show promiscuity toward different substrates. The three predicted glycosyltransferase gene products of CHCC11848, which might act sequentially to build the oligosaccharide repeat unit, showed low amino acid similarity with known glycosyltransferases. The structure of the repeat unit could thus also be different from those known to date for *Lactococcus*. The sugar specificity of the glycosyltransferases needed for EPS biosynthesis can probably be predicted according to the sugars present in the EPS. However, the structure of EPS produced by CHCC11848 has not been resolved yet.

*L. lactis* is found in many environments, although the original niche for *L. lactis* is now widely accepted to be plant based. Lactococcal strains that are used in the dairy industry appear to have undergone extensive adaptation to the nutrient-rich dairy environment through a process of reductive evolution, which, when compared to lactococcal strains isolated from plant material, appears to have resulted in a smaller genome size, a higher number of pseudogenes and acquisition of a much more extensive plasmid complement. As most nondairy isolates belong to the lineage containing strains of *L. lactis* subsp. *lactis*, and represent molecular diversity not found within the dairy strains, whereas *L. lactis* subsp. *cremoris* is typically found in dairy fermentations, it is expected result to find more texturizing strains from the subsp. *cremoris* than from the subsp. *lactis*. Thus CHCC11848 is a unique strain from the subsp. *lactis* able to positively contribute to the milk texturing properties.

A typical lactococcal eps operon consists of a conserved part including genes epsR, epsX, epsA, epsB, epsC, and epsD, a variable part, which includes a polymerase, a transporter and one or more glucosyltransferases or other polymer modifying genes, and another conserved part including genes epsL and orfY (Dabour and LaPointe 2005, Forde and Fitzgerald 2003, Nierop Groot and Kleerebezem 2007, van Kranenburg 1997, van Kranenburg 1999). The predicted functions of eps genes divide the eps operon into regions covering regulation (epsR), modulation of EPS synthesis including chain length determination (epsABC), biosynthesis of the oligosaccharide repeat unit including linkage of the first sugar to the lipid carrier (epsD) and subsequent addition of sugar to lipid-linked sugar or other moieties modifying the repeat unit performed by the genes of the variable part of the cluster, as well as polymerization (wzy), and export (wzx). No putative function could be yet assigned to epsX and epsL. NIZO B40 epsL can be disrupted by single crossover using an internal gene fragment or overproduced without any effect on EPS production (van Kranenburg 1999). However it might be that the second copy of epsL, which we have found in a putative cluster for glycosylated techoic acids in several lactococcal strains (see Example 4 for details), takes over, if the one from the eps cluster is not functional.

EpsR is responsible for EPS biosynthesis regulation, and thus certain mutations would affect the EPS production. EpsABC and ATP are believed to form a stable complex acting as a tyrosine kinase—phosphatase system, which controls EPS synthesis, likely through the phosphorylation of EpsD, a glycosylphospho-transferase that catalyzes the first step in the assembly of the EPS repeat unit, and defines the type of sugar added to the lipid carrier for the formation of EPS. All three genes responsible for tyrosine phosphorylation are essential for the complete encapsulation of the pneumococcus, with CpsC being a major virulence factor, crucial via its role in the regulation of the CPS biosynthesis (Whittall et al 2015). In *L. lactis*, the product of the cpsC-like gene, EpsA, is classified as chain length determinant protein, while EpsB is a putative tyrosine protein kinase, and EpsC, a putative tyrosine protein phosphatase. In *L. lactis*, EpsA and EpsB were found to be essential for the EPS production, while EpsC was not strictly required, as the effect of its deletion was the reduced amount of EPS produced (Nierop Groot and Kleerebezem 2007). Gene epsD encoding the initial glycose phosphate transferase, which does not catalyze glycosidic linkage, but is involved in linking the first sugar of the repeat unit to the lipid carrier, was shown to be essential for polysaccharide biosynthesis in *L. lactis*, as its disruption abolished EPS production (Dabour and LaPointe 2005, van Kranenburg et al 1997).

Subsequently, the following genes of the eps cluster typically encoding glycosyltransferases, polymerases and transporters are situated in a variable part of the cluster, and do often have a low degree of similarity to already characterized genes, which makes the prediction of their putative functions difficult. Comparison of polysaccharide synthesis operons from 90 pneumococcal serotypes, where polysaccharide biosynthesis is well studied, revealed that central genes responsible for the synthesis and polymerization of the repeat unit are highly variable and often non-homologous between serotypes (Bentley et al 2006). Wzy-dependent CPS biosynthesis in *S. pneumoniae* resembles peptidoglycan synthesis, whereby repeat units are built on the inner face of the cytoplasmic membrane, transported to the outer face of the membrane by a Wzx transporter, also called flippase, and polymerized by a Wzy polymerase. The polysaccharide polymerase wzy links individual repeat units to form lipid-linked CPS. In *S. pneumonia*, 40 homology groups for polysaccharide polymerases were found. The initial sugar of the repeat oligosaccharide unit is also the donor sugar in the polymerization of the repeat units, and the specificity of the Wzy polymerase determines the linkage type. The predictions for initial sugars, and subsequent repeat-unit polymerization linkage, correlate well with the polymerase homology groups. In *S. pneumonia*, there are 32 polymerase homology groups associated with WchA, five with WciI, four with WcjG and one with WcjH. These associations are mostly exclusive, with only five polymerase homology groups associated with two initial transferases, which indicates a high specificity of the initial transferases (Bentley et al 2006).

Engineering strategies for increased production of EPS aiming at increasing pool of sugar nucleotides (i.e., EPS precursors) to enhance the carbon flux toward the final polymer, overexpression of genes involved in the EPS assembly (e.g., Wzx, Wzy, glycosyltransferases), targeted engineering of regulatory protein, disruption of pathways competing for precursors, or single gene knock-outs were successful for some EPS producers, but failed in other cases (for a review see Schmid et al 2015). Overexpression of the entire eps gene cluster in *L. lactis* NIZO B40 strain resulted in significantly reduced growth rate, suggesting that increased EPS production generates a significant metabolic burden due to the required high-level production of sugar nucleotides, which are utilized in both EPS production and growth (Boels et al 2003). The optimization of manufacturing process parameters might be more promising than engineering EPS biosynthesis for many established industrial EPS producers (Schmid et al 2015).

The nucleotide sequence of SEQ ID NO:1 includes the eps gene cluster of CHCC11848.

Any combination of the above-described elements, aspects and embodiments in all possible variations thereof is encompassed by the invention unless otherwise indicated herein or otherwise clearly contradicted by context.

Embodiments of the present invention are described below, by way of examples only.

EXAMPLES

Example 1. High-Throughput Screening for Texturing Strains and Measurement of Milk Gel Texture Milk (liquid) is typically converted into milk gel (soft solid) when fermented with lactic acid bacteria typically belonging to *Streptococcus thermophilus, Lactobacillus* spp. and
*Lactococcus lactis* spp. Rheometer or texture analyzer are typically used to assess rheological properties of fermented milk gels, such as shear stress. Shear stress measurements are related to perceived mouth thickness, when the texture of milk gels is assessed by a sensory panel. High mouth thickness is considered an important quality factor of fermented milk gels such as yoghurt, and consumer acceptance is often very closely linked to the texture properties such as mouth thickness, which is a function of shear stress.

A liquid handling station, Hamilton Robotics MicroLab Star, equipped with pressure sensor inside the air displacement barrel of the individual pipettes was used in the following experiment. The liquid handler has a pressure sensor located in the headspace of each pipetting channel. Pressure data from each sensor was collected by TADM (Total Aspiration Dispense Monitoring) software of the Hamilton Robotics MicroLab Star liquid handler (Hamilton Robotics).

FIG. 1 shows aspiration pressure values at 1 s (Pa) measured by pipetting using Hamilton liquid handling unit plotted against shear stress (Pa) at shear rate 300 $s^{-1}$ data measured using rheometer for selected milk gel samples obtained by fermenting milk using eight different *L. lactis* subsp. *lactis* strains. "Milk" refers to B-milk, which was not inoculated with any strain, and was used as a control. In the present context, 9.5% B-milk is boiled milk made with reconstituted low fat skim milk powder to a level of dry matter of 9.5% and pasteurized at 99° C. for 30 min, followed by cooling to 40° C.

Pressure versus time data (TADM) were obtained from 1-ml samples made in a 96-well micro-titer plate, where B-milk was inoculated for 20 h at 30° C. in the presence of different strains (1% of inoculum) unless otherwise stated, and then stored at 4° C. for 1 day. Hamilton liquid handling unit was used to measure pressure during aspiration, and pressure values of each sample corresponding to the time point of 1 s were plotted on the y-axis of FIG. 4. A volume of 500 µl was aspirated (350 µL/s).

Shear stress data were obtained by inoculating the same microbial cultures in semi-fat milk (1.5% fat) enriched with 2% skim milk powder; milk was heated at 90° C. for 20 min and cooled down to the inoculation temperature, prior to inoculation with 1% overnight microbial culture. The inoculation took place for 12-15 h at 30° C. in 200-ml scale until pH~4.55 followed by cooling to 4° C. and storage for 5 days at 4° C. After the storage, the fermented milk was stirred gently by means of a stick fitted with a bored disc until homogeneity of the sample. Shear stress of the samples was assessed on a rheometer (Anton Paar Physica Rheometer with ASC, Automatic Sample Changer, Anton Paar® GmbH, Austria) using the following settings:

Wait time (to rebuild to somewhat original structure)
5 minutes without oscillation or rotation
Rotation (to measure shear stress at 300 $s^{-1}$ etc.)
Y'=[0.2707-300] $s^{-1}$ and y'=[275-0.2707] $s^{-1}$ 21 measuring points over 210 s (on every 10 s) going up to 300 $s^{-1}$ and 21 measuring points over 210 s (one every 10 s) going down to 0.2707 $s^{-1}$ For the data analysis, the shear stress at shear rate 300 $s^{-1}$ was chosen.

Strain CHCC11848 had the highest shear stress out of the eight different *L. lactis* subsp. *lactis* strains tested, both according to the TADM and the rheometer measurements (FIG. 1). A significant correlation ($R^2$ of 0.97) was observed between the TADM and the rheometer measurements.

Example 2. Sequencing Genomes of Lactococcal Strains

Total DNA was purified from a culture grown overnight at 30° C. in M17 medium containing 1% lactose and 1% glucose using DNeasy Blood & Tissue Kit (Qiagen). The DNA quality was checked using gel electrophoresis, the DNA concentration was estimated using Nanodrop 2000 spectrophotometer, and 15 µg DNA (approximately 150 ng/µl) were used for sequencing at BGI (HongKong, China) using Illumina HiSeq equipment with pair-end channel module with 2×100 bp read length and an insert size of 500 bp. The assembly of raw reads into contigs was performed using CLC Genomics workbench 7.0 software with default parameters resulted in 48 contigs (average length 57325 bp, average coverage 317), which were used for eps gene mining.

Example 3. Characterization of the Eps Gene Cluster of Lactococcal Strains

Since an enhanced texture is associated with the production of EPS, the texturing and non-texturing lactococcal strains from the CHCC culture collection presented on FIG. 1 were genome-sequenced. Mining for eps gene clusters was performed, and the eps clusters found were compared to those of the publicly available lactococcal genome sequences. We focused on the subsp. *lactis*, as none of the strains from this subsp., for which genome sequences were available, are reported as texturing, indicating that CHCC11848 is a unique strain from the subsp. *lactis* with enhanced texturing properties.

Figures 3A, 3B:
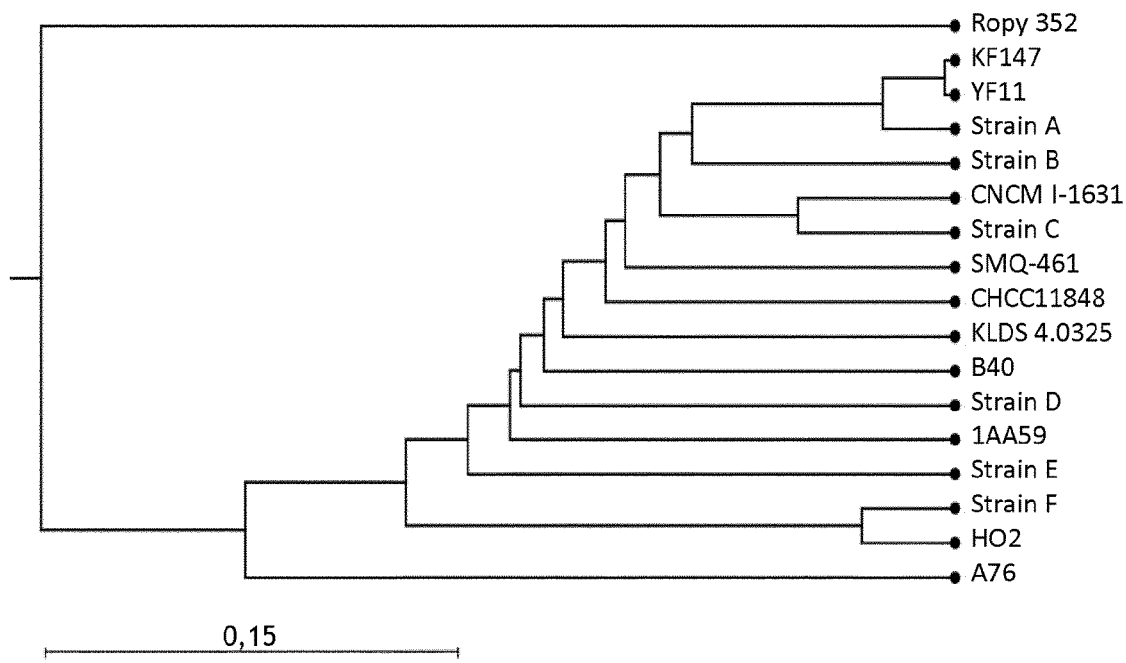
FIG. 3A shows the phylogenetic tree of eps clusters of *L. lactis* subsp. *lactis* strains from Chr. Hansen's culture collection and several publicly available *L. lactis* genomes constructed using "Create Tree" tool within "Alignments and Trees" set of tools of the CLC Main Workbench 7 software (construction method: UPGMA; nucleotide substitution model: Jukes Cantor; bootstrapping was performed using 200 replicates).
FIG. 3B depicts the localization of the eps clusters in publicly available sequences.

In order to find eps gene clusters in the lactococcal strains under investigation, "BLAST" tool of the software "CLC Main Workbench 7" was applied using standard parameters. 13 *Lactococcus lactis* subsp. *lactis* strains, for which complete genomes or contigs were available in the NCBI database on Apr. 27, 2015, were used for eps gene cluster mining: KLDS 4.0325 (GenBank CP006766), Il1403 (GenBank AE005176), CNCM I-1631 (GenBank AGHX00000000), CV56 (GenBank CP002365), Dephy 1 (GenBank CBUJ000000000), KF147 (GenBank CP001834), YF11 (GenBank APAV00000000), IO-1 (GenBank AP012281), A12 (GenBank CBLU000000000), 1AA59 (GenBank AZQT00000000), JCM 5805=NBRC 100933 (GenBank BBSI00000000), K214 plasmid pK214 (GenBank NC_009751), NCDO2118 (GenBank CP009054), and NCDO 2118 plasmid pNCDO2118 (GenBank CP009055). No eps clusters were found in CV56, Il1403, IO-1, JCM 5805, A12, Dephy 1, K214 plasmid pK214, NCDO 2118 genome and plasmid pNCDO2118. The eps clusters found in the remaining five strains, together with the eps clusters from five different *L. lactis* subsp. *cremoris* strains such as NIZO B40 (GenBank AF036485), SMQ-461 (GenBank AY741550.2), Ropy352 (GenBank EF192213), HO2 (GenBank AF142639), and A76 (GenBank CP003132), were used as eps cluster references for BLAST analysis of the lactococcal strains from the CHCC culture collection (FIG. 3B). Mining for eps gene clusters in the lactococcal strains from CHCC culture collection was performed first using the assembled genomes (containing contigs), and in the case no eps genes were found in the assembled genomes, "Map Reads to reference" tool of CLC Main Workbench 7 software was applied using standard parameters. The latter was performed to ensure that no raw reads representing eps genes that were not assembled into contigs were present in the raw genome data.

Both BLAST analysis results and results of alignment of the eps gene clusters from different lactococcal strains to each other using "Create Alignment" tool within "Alignments and Trees" set of tools of the CLC Main Workbench 7 software were used to make annotations of ORF of the strains from the CHCC culture collection. "Create Tree" tool within "Alignments and Trees" set of tools of the CLC Main Workbench 7 software (construction method: UPGMA; nucleotide substitution model: Jukes Cantor; bootstrapping was performed using 200 replicates) was used to create a phylogenetical tree based on *L. lactis* subsp. *lactis* and *cremoris* alignment files (FIG. 3A). The identity of sequences was calculated using percent identity matrix by ClustalW2 (available through CLC software) (FIG. 3C). InterPro (www.ebi.ac.uk/interpro/) and Pfam (pfam.xfam.org) tools were used for functional characterization of proteins by classifying them into families, predicting hydrophobicity profile, domains and important sites.

Figure 2:
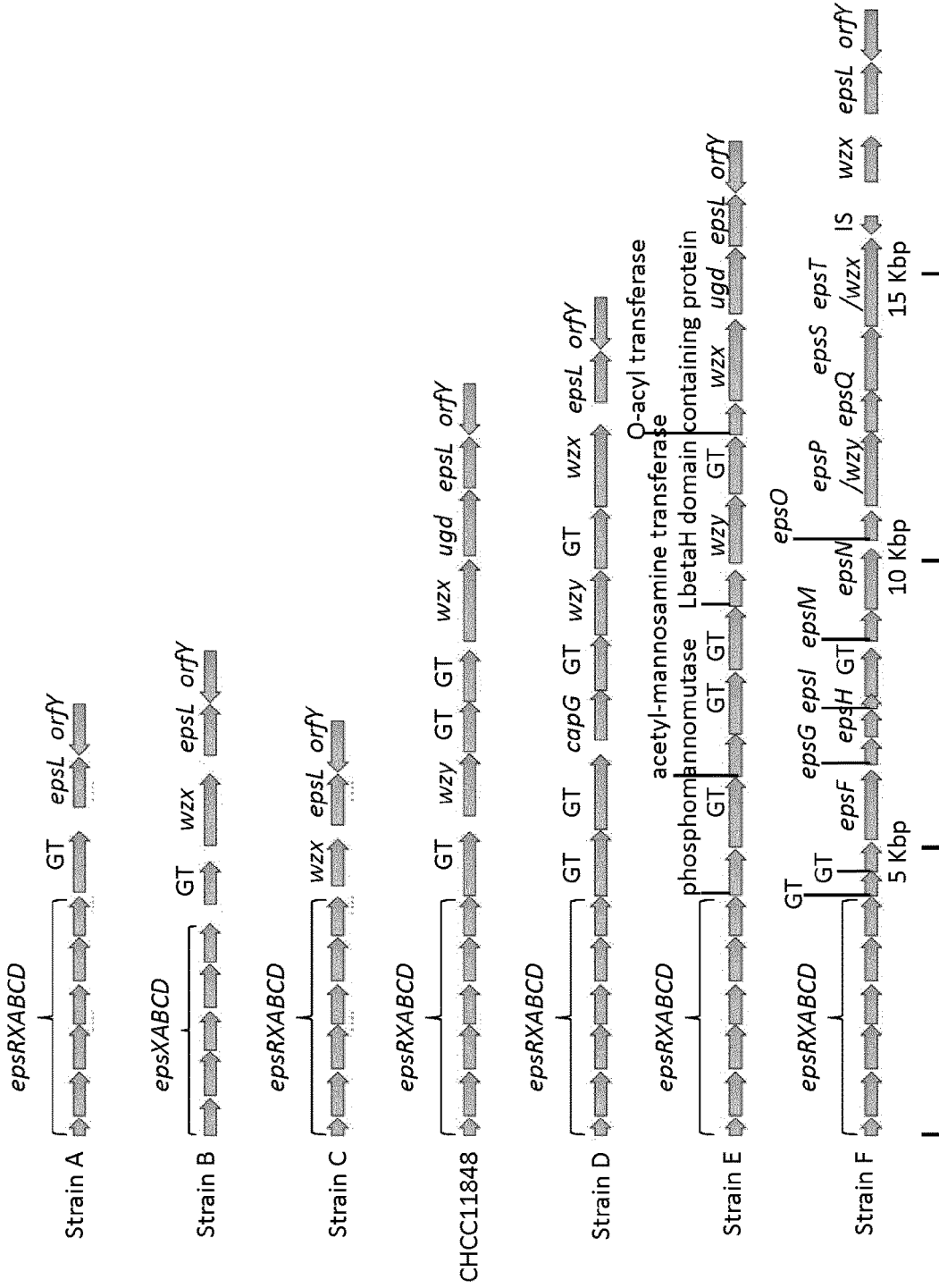
FIG. 2 depicts an overview of eps clusters of *L. lactis* subsp. *lactis* strains from Chr. Hansen's culture collection and several publicly available *L. lactis* genomes, described on FIG. 3 B. ORFs are annotated according to their proven or predicted functions, based on BLAST analysis on NCBI web-page against refseq protein database using default parameters. Because of differences in the eps gene nomenclature, some automatic annotations belonging to the publicly available sequences were renamed here to enable the eps gene cluster comparisons. The ORFs of eps clusters from Chr. Hansen's culture collection strains structurally similar to those from publicly available sequences were annotated in the same way, for instance the eps cluster of Strain F was annotated as in HO2. GT, glycosyltransferase; IS, transposase; hypot, hypothetical protein.

A large eps cluster diversity was observed in the lactococcal strains under investigation (FIG. 2). Only two strains from the subsp. *lactis*, KF147 and YF11, were found to have very similar (99% identical from epsX to epsL) eps clusters, based on their nucleotide sequence analysis by ClustalW2 (FIG. 3A, 3C), but containing a significant number of single nucleotide polymorphisms (SNP), e.g. 13 SNP in epsX (10 resulting in amino acid changes), 13 SNP in epsA (four resulting in amino acid changes), four in epsB (one resulting in amino acid change), six in epsC (three resulting in amino acid changes), 29 SNP in epsD (14 amino acid changes). Despite the eps cluster of CHCC11848 seemed somewhat similar to those of publicly available lactococcal strains and those from the CHCC culture collection (FIG. 2), the similarity was highest in the conserved regions of the cluster, from epsR to epsD and from epsL to orfY. When comparing the eps cluster of CHCC11848 with that of KLDS 4.0325, the identity of the conserved region of the eps cluster from epsX to epsD was 97%, from epsL to orfY, 98%, while the identity of the variable region, between epsD and epsL was 71% on the nucleotide level.

Example 4. Characterization of the Eps Gene Cluster of CHCC11848

Figure 4:
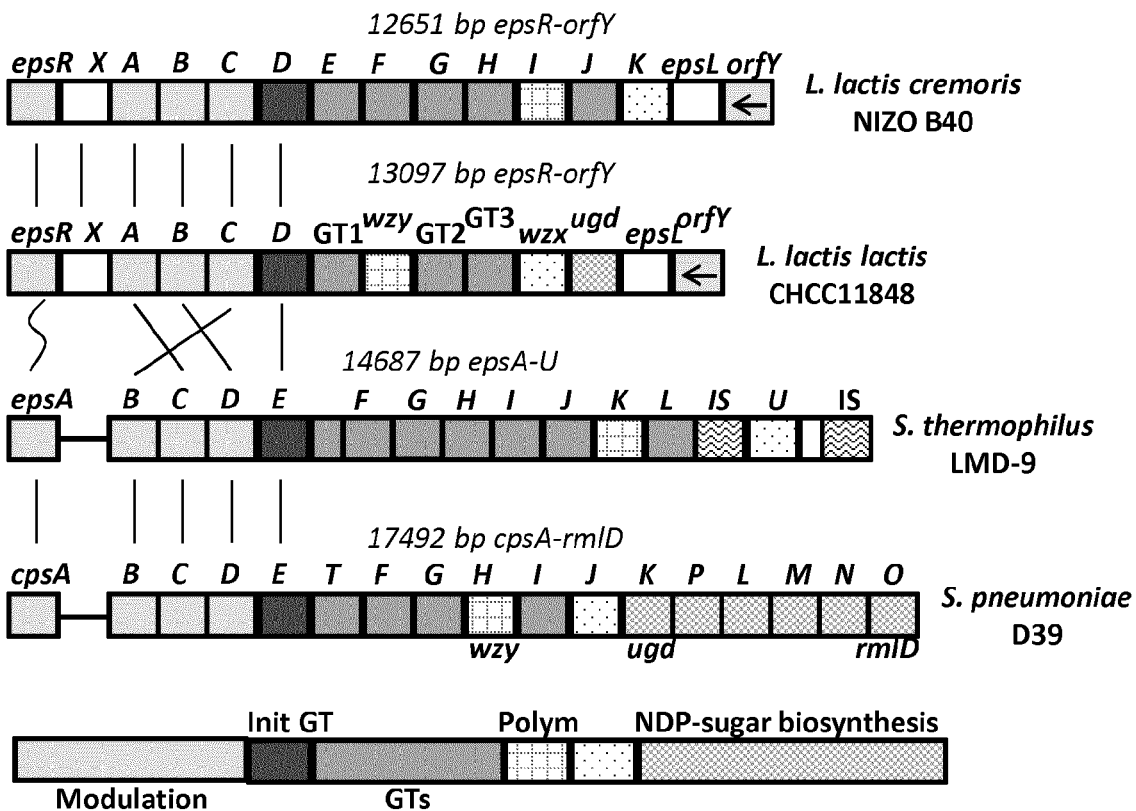
FIG. 4 shows the genetic organization of the eps clusters of *L. lactis* strains NIZO B40, CHCC11848, *S. thermophilus* LMD-9, and *S. pneumoniae* D39. Gene functional grouping marked with different colors. Relative localizations of eps genes with similar functions are indicated with connection lines. Arrows represent genes oriented in the opposite transcriptional sense. Genes with unknown functions are in white; genes not likely being involved in the EPS biosynthesis are in grey; transposase-like ORF are in black; truncated genes are shown as short boxes. GT, glycosyltransferase; init, initial; polym, polymerization; transp, transport; NDP-sugar, nucleotide diphospho-sugar.
Figure 5:
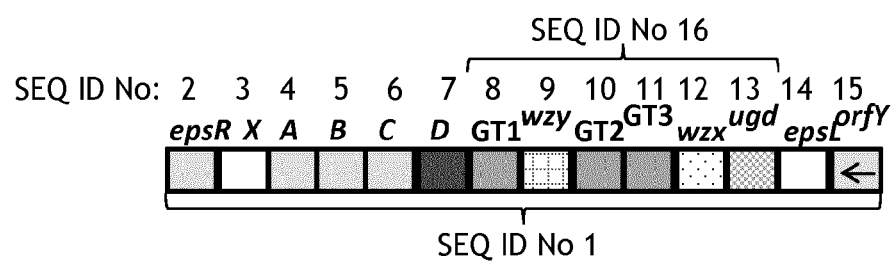
FIG. 5 depicts the gene organization of identified ORFs, predicted properties of the hypothetical proteins encoded by the eps gene cluster from CHCC11848, and comparison of the predicted proteins with those in other bacteria. BLAST analysis performed on May 13, 2015 using blastp tool of NCBI (default parameters) against Non-redundant (nr) protein, refseq_protein, and *S. pneumoniae* (taxid:1313) databases; the top scores from each analyses are shown. Protein domains were identified using InterPro and Pfam tools. However, the results of blastp analysis against nr are shown only when they were different from those obtained from the refseq_protein database. E value (expectation value) is the number of alignments that are expected to occur by chance in a database search with similarity scores to the query equal to or better than that of the result sequence; it is indicated as an exponent of 10. GT, glycosyltransferase; IS, transposase; hypot, hypothetical protein; EPS, exopolysaccharide; aa, amino acid.

The eps operon of CHCC11848 included 14 open reading frames (ORF) covering 13 kb and oriented in the same transcriptional sense except for the last gene of the cluster, orfY (FIG. 4, FIG. 5). As for many lactococcal strains including NIZO B40, HO2 and SMQ-461, orfY was found at the 3' end of the eps gene cluster and was oriented in the opposite transcriptional sense (FIG. 4). This gene was followed by a putative cadmium resistance protein cadA. Based on the amino acid similarity, putative functions could be assigned to 12 out of 14 ORFs identified (FIG. 5). The predicted functions of eps genes divide the eps operon into regions covering regulation (epsR), modulation of EPS synthesis including chain length determination (epsABC), biosynthesis of the oligosaccharide repeat unit including linkage of the first sugar to the lipid carrier (epsD) and subsequent addition of sugar or other moieties modifying the repeat unit (GT1, GT2, GT3, ugd), as well as polymerization (wzy), and export (wzx). No putative function could be yet assigned to epsX and epsL.

The organization of the eps gene cluster from *L. lactis* is similar to that of the gene clusters encoding EPS biosynthesis in *S. thermophilus* and CPS biosynthesis in *S. pneumoniae* (FIG. 4). We have named the conserved genes of CHCC11848 according to the nomenclature commonly used for the lactococcal eps genes (Dabour and LaPointe 2005, Forde and Fitzgerald 2003, Nierop Groot and Kleerebezem 2007, van Kranenburg 1997, van Kranenburg 1999). However, eps genes with the same names often have different functions in different organisms, as the genes are often designated alphabetically by order of occurrence in a given locus and not based on their functions. Thus, epsB is *L. lactis* encodes tyrosine protein kinase, while the corresponding gene in *S. thermophilus* is named epsD, and in *S. pneumoniae*, cpsD (or wxe) (FIG. 4). In NIZO strain B40, the EPS polymeraze is named epsI, and the export gene, epsK, while in SMQ-461, the genes with corresponding functions are names epsH and epsM. The original nomenclature for *S. pneumoniae* capsules utilizes cps followed by the serotype number and gene designation, where genes are designated alphabetically by order of occurrence in a given locus, while an alternative nomenclature is based on functions (e.g. wzg), but lacks the ability to readily distinguish serotype. The nomenclature of the *S. thermophilus* eps genes is closely related to that of the pneumococcal one; however the genes are generally named eps and not cps. In order to annotate the genes of CHCC11848, we made protein functional characterization using InterPro and Pfam tools, additionally to the BLAST analysis (FIG. 5).

CHCC11848 was found to contain highly conserved epsR, which was assigned for EPS biosynthesis regulation, as it contains a DNA binding domain, and is identical to a lactococcal putative transcriptional regulator from XRE family (FIG. 5). The corresponding transcriptional regulators of EPS synthesis in e.g. *S. thermophilus* LMD-9 and *S. pneumoniae* D39, epsA and cpsA, respectively, belong to the LytR family of transcriptional regulators, similarly to orfY from CHCC11848. While EpsA and CpsA contained three putative transmembrane segments at the N terminus and a large hydrophobic segment, OrfY had a similar hydrophobicity profile, but only one transmembrane segment. LytR group of transcriptional regulators represent a different regulatory mechanism from EpsR that has not been investigated to date.

Both EpsX and EpsL shared highly significant similarity (98 and 99% identity, respectively) with related sequences from lactococcal strains (FIG. 5). However, there are no available experiments to assess their functions to date. NIZO B40 epsL can be disrupted by single crossover using an internal gene fragment or overproduced without any effect on EPS production (van Kranenburg 1999). The hydrophobicity plot of EpsL of CHCC11848 showed a large hydrophobic, a cytoplasmic, and a transmembrane segment. It was predicted that EpsL is a periplasmic protein containing DUF2233 domain of unknown function (FIG. 5). Curiosly we found epsL-like genes as a part of lactococcal eps clusters, when present, but also in techoic acid clusters. For instance, *L. lactis* strain KF147 was found to contain two epsL-like genes in its genome, one in the putative techoic acid cluster (protein id ABX75721, locus tag LLKF_0940 of GenBank sequence CP001834) and one in the eps gene cluster (protein id ABX75689, locus tag LLKF_0142). Strains CV56 and Il1403, which do not seem to have an eps cluster, were found to contain one epsL-like gene each in their putative techoic acid clusters. The hydrophobicity profile of EpsX showed that it possesses a large cytoplasmic, a non-cytoplasmic, and a transmembrane segment; the latter could function as a membrane anchor. The cytoplasmic region of EpsX included a domain with similarity to GDSL-like Lipase/acylhydrolase family of presumed lipases and related enzymes, and to SGNH-hydrolase superfamily enzymes belonging to a diverse family of lipases and esterases. The role of epsX and epsL in the EPS biosynthesis remains to be established.

Strains CV56 and Il1403 both have putative (lipo)techoic acid clusters. CV56 contains a gene encoding O-antigen export system ATP-binding protein in its putative lipotechoic acid cluster; it represents a lipopolysaccharide exporter (locus tag CVCAS_0185 of the GenBank sequence CP002365, protein id ADZ62853, protein name RFB1 aka RfbB, accession nr Q48476 in the transporter classification database tcdb.org), which is required for translocation of lipopolysaccharide O-antigen side-chains across the cytoplasmic membrane. The ABC transporter found within the putative lipotechoic acid cluster of Il1403 (protein id AAK04301, locus tag L4342 of the NCBI sequence NC_002662) was 79% identical to that of CV56, based on ClustalW2 analysis, and was classified as ABC transporter required for O-antigen biosynthesis and multicellular development, RfbAB (accession nr Q50863 in tcdb.org). Techoic acid ABC transporter ATP binding protein found within putative techoic acid clusters of CV56 (protein id ADZ63531, locus tag CVCAS_0878 of the GenBank sequence CP002365) and Il1403 (protein id AAK05013, locus tag L137446 of the NCBI sequence NC_002662) were 99.8% identical, based on ClustalW2 analysis, and were classified as techoic acid exporters TagGH (accession nr P42954 in tcdb.org).

EpsABC and ATP are believed to form a stable complex acting as a tyrosine kinase-phosphatase system, which controls EPS synthesis, likely through the phosphorylation of EpsD, a glycosylphospho-transferase that catalyzes the first step in the assembly of the EPS repeat unit, and defines the type of sugar added to the lipid carrier for the formation of EPS. All three genes responsible for tyrosine phosphorylation are essential for the complete encapsulation of the pneumococcus, with CpsC being a major virulence factor, crucial via its role in the regulation of the CPS biosynthesis.

In CHCC11848, the product of the cpsC-like gene, EpsA, has been classified as chain length determinant protein, while EpsB was found to be a putative tyrosine protein kinase, and EpsC, a putative tyrosine protein phosphatase. The three proteins have a high degree of similarity to the corresponding proteins in other organisms (FIG. 5), but have a different order in the eps cluster of CHCC11848 than in *S. thermophilus* LMD-9 and *S. pneumoniae* D39 (FIG. 4). Gene epsD is likely to encode the initial glycose phosphate transferase, which does not catalyze glycosidic linkage, but is involved in linking the first sugar of the repeat unit to the lipid carrier. The initial glycose phosphate transferase was shown to be essential for polysaccharide biosynthesis, as its disruption abolished EPS production. While the majority of pneumococcal serotypes contain wchA, and where wchA is absent, the products of the fifth cps gene fall into homology groups WciI, WcjG or WcjH, the epsD of CHCC11848 containing a large cytoplasmic segment and one transmembrane segment was found to belong to the WcjG group (FIG. 5).

Subsequently, the following genes of the eps cluster of CHCC11848 encoding glycosyltransferases may transfer various nucleotide sugars including UDP-glucose, UDP-galactose, dTDP-rhamnose, UDP-GlcNAc and UDP-galactofuranose to form the repeating units in a glycosidic linkage-dependent manner. All three predicted glycosyltransferase gene products of CHCC11848 showed relatively low amino acid similarity with known glycosyltransferases (FIG. 5). The three glycosyltransferases GT1, GT2, GT3 together with ugd encoding UDP-glucose 6-dehydrogenase are potentially involved in sequential building of the repeat unit, although their specific functions and therefore order of action have not been demonstrated. The protein encoded by ugd was previously found in *L. lactis* pCI658-encoded eps operon. It converts UDP-glucose to UDP-glucuronic acid, which is possibly one of the components of the EPS structure of CHCC11848. However, chemical structure and sugar composition of the EPS repeat unit of CHCC11848 remain to be determined. Comparison of polysaccharide synthesis operons from 90 pneumococcal serotypes revealed that central genes responsible for the synthesis and polymerization of the repeat unit are highly variable and often non-homologous between serotypes (Bentley et al 2006). Wzy-dependent CPS biosynthesis in *S. pneumoniae* resembles peptidoglycan synthesis, whereby repeat units are built on the inner face of the cytoplasmic membrane, transported to the outer face of the membrane by a Wzx flippase, and polymerized by a Wzy polymerase. The polysaccharide polymerase wzy links individual repeat units to form lipid-linked CPS. In *S. thermophilus* LMD-9, epsK encoding polysaccharide polymerase has nine transmembrane segments, and the corresponding polymerase in *S. pneumoniae* D39, epsH or wzy, has 11 transmembrane segments, both representing an O-antigen ligase like membrane protein. Based on sequence identity analysis by ClustalW2, the putative polymerase of CHCC11848, Wzy, had only 12 and 14% identity to the polymerases from LMD-9 and D39, respectively. The hydrophobicity plot for Wzy from CHCC11848 showed 10 transmembrane segments and seems related to a protein family that includes EpsG from *Bacillus subtilis* and Wzy from *Acinetobacter baumannii* (FIG. 5). Despite being classified as belonging to the same protein type by BLAST analysis and InterPro and Pfam tools, polymerases from LMD-9 and D39 were found only being 14% identical to each other on the amino acid level. In *S. pneumonia*, 40 homology groups for polysaccharide polymerases were found. The initial sugar of the repeat oligosaccharide unit is also the donor sugar in the polymerization of the repeat units, and the specificity of the Wzy polymerase determines the linkage type. The predictions for initial sugars, and subsequent repeat-unit polymerization linkage, correlate well with the polymerase homology groups. In *S. pneumonia*, there are 32 polymerase homology groups associated with WchA, five with WciI, four with WcjG and one with WcjH. These associations are mostly exclusive, with only five polymerase homology groups associated with two initial transferases, which indicates a high specificity of the initial transferases (Bentley et al 2006). The gene product of wzx of CHCC11848 shares moderate similarity with other predicted lactococcal flippases and has 12 predicted transmembrane regions.

DEPOSIT AND EXPERT SOLUTION

The applicant requests that a sample of micro-organisms deposited for the present application as described below may only be made available to an expert, until the date on which the patent is granted.

30 *Lactococcus lactis* subsp. *lactis* CHCC11848 was deposited with DSMZ-Deutsche Sammlung von Mikroorganismen and Zellkulturen GmbH, Inhoffenstr. 7B, D-38124 Braunschweig, on Aug. 21, 2014 under the accession no. DSM 29291.

The deposit was made according to the Budapest treaty on the international recognition of the deposit of microorganisms for the purposes of patent procedure.

REFERENCES

1. Ai Q, Liu H, Zhang H, Zhong D. New *Lactobacillus* strains that produce bile salt hydrolase (BSH) and exopolysaccharide (EPS), useful for preparing yogurt that can lower blood cholesterol and has improved stability due to the exopolysaccharide. Patent CN 101 331 900 A
2. Boels I C, Van Kranenburg R, Kanning M W, Chong B F, De Vos W M, Kleerebezem M. 2003. Increased exopolysaccharide production in *Lactococcus lactis* due to increased levels of expression of the NIZO B40 eps gene cluster. Appl Environ Microbiol. 69: 5029-5031.
3. Bentley S D, Aanensen D M, Mavroidi A, Saunders D, Rabbinowitsch E, Collins M, Donohoe K, Harris D, Murphy L, Quail M A, Samuel G, Skovsted I C, Kaltoft M S, Barrell B, Reeves P R, Parkhill J, Spratt B G. 2006. Genetic analysis of the capsular biosynthetic locus from all 90 pneumococcal serotypes. PLoS Genet. 2:e31.
4. Dabour N, LaPointe G. 2005. Identification and Molecular Characterization of the Chromosomal Exopolysaccharide Biosynthesis Gene Cluster from *Lactococcus lactis* subsp. *cremoris* SMQ-461. Appl Environ Microbiol. 71: 7414-7425.
5. Forde A, Fitzgerald G F. 2003. Molecular organization of exopolysaccharide (EPS) encoding genes on the lactococcal bacteriophage adsorption blocking plasmid, pCI658. Plasmid. 49: 130-142.
6. Goujon M, McWilliam H, Li W, Valentin F, Squizzato S, Paern J, Lopez R. 2010. A new bioinformatics analysis tools framework at EMBL-EBI. Nucleic Acids Res. 38: W695-W699.
7. Larkin M A, Blackshields G, Brown N P, Chenna R, McGettigan P A, McWilliam H, Valentin F, Wallace I M, Wilm A, Lopez R, Thompson J D, Gibson T J, Higgins D G. 2007. Clustal W and Clustal X version 2.0. Bioinformatics. 23: 2947-2948.

8. Nierop Groot M N, Kleerebezem M. 2007. Mutational analysis of the *Lactococcus lactis* NIZO B40 exopolysaccharide (EPS) gene cluster: EPS biosynthesis correlates with unphosphorylated EpsB. J Appl Microbiol. 103: 2645-2656
9. Pan D, Mei X. 2010. Antioxidant activity of an exopolysaccharide purified from *Lactococcus lactis* subsp. *lactis* 12. Carbohydrate Polymers 80: 908-914
10. Schmid J, Sieber V, Rehm B. 2015. Bacterial exopolysaccharides: biosynthesis pathways and engineering strategies. Front Microbiol. 6: 496.
11. Suzuki C, Kobayashi M, Kimoto-Nira H. Novel exopolysaccharides produced by *Lactococcus lactis* subsp. *lactis*, and the diversity of epsE genes in the exopolysaccharide biosynthesis gene clusters. 2013. Biosci Biotechnol Biochem. 77: 2013-2018.
12. van Kranenburg R, Marugg J D, van Swam I I, Willem N J, de Vos W M. 1997. Molecular characterization of the plasmid-encoded eps gene cluster essential for exopolysaccharide biosynthesis in *Lactococcus lactis*. Mol Microbiol. 2: 387-397
13. van Kranenburg R, Vos H R, van Swam I I, Kleerebezem M, de Vos W M. 1999. Functional analysis of glycosyltransferase genes from *Lactococcus lactis* and other gram-positive cocci: complementation, expression, and diversity. J Bacteriol. 181: 6347-6353
14. Whittall J J, Morona R, Standish A J. 2015. Topology of *Streptococcus pneumoniae* CpsC, a Polysaccharide co-polymerase and BY-kinase adaptor protein. J Bacteriol 197: 120.

The invention claimed is:

1. A fermented dairy product comprising a texturizing *Lactococcus lactis* subsp. *lactis* acid bacterium strain comprising an active eps gene cluster capable of producing exopolysaccharide (EPS), wherein the eps gene cluster comprises one or more nucleotide sequences selected from:
   (a) a nucleotide sequence encoding a polypeptide having polymerase activity, wherein the polypeptide has at least 95% sequence identity with the amino acid sequence encoded by the nucleotide sequence of SEQ ID NO:9 ("wzy");
   (b) a nucleotide sequence encoding a polypeptide having polysaccharide transporter activity, wherein the polypeptide has at least 95% sequence identity with the amino acid sequence encoded by the nucleotide sequence of SEQ ID NO:12 ("wzx"); and
   (c) one or more nucleotide sequences encoding a polypeptide having glycosyltransferase (GT) activity selected from:
      (i) a polypeptide having at least 95% sequence identity with the amino acid sequence encoded by the nucleotide sequence of SEQ ID NO:8 ("GT1");
      (ii) a polypeptide having at least 95% sequence identity with the amino acid sequence encoded by the nucleotide sequence of SEQ ID NO:10 ("GT2"); and
      (iii) a polypeptide having at least 95% sequence identity with the amino acid sequence encoded by the nucleotide sequence of SEQ ID NO:11 ("GT3");
   wherein said fermented dairy product is produced by a process comprising fermenting a milk substrate with said texturizing *Lactococcus lactis* subsp. *lactis* acid bacterium strain, and wherein said fermented dairy product has improved texture as compared to a fermented dairy product produced without said texturizing *Lactococcus lactis* subsp. *lactis* acid bacterium strain.

2. The fermented dairy product of claim 1, wherein the texturizing *Lactococcus lactis* subsp. *lactis* acid bacterium strain generates fermented milk having a shear stress greater than 40 Pa when measured at shear rate 300 s$^{-1}$ when tested under the following conditions:
   providing 200 ml semi-fat milk (1.5% fat) enriched with 2 g skim milk powder, heating the milk to 90° C. for 20 minutes, followed by cooling to an inoculation temperature of 30° C., inoculating with 2 ml of an overnight culture of the texturizing strain, maintaining the milk at inoculation temperature until pH 4.55 is reached, followed by storage at 4° C. for 5 days, followed by gently stirring and measuring the shear stress at shear rate 300 s$^{-1}$.

3. The fermented dairy product of claim 1, wherein the dairy product has a shear stress greater than 40 Pa when measured at a shear rate of 300 s$^{-1}$.

4. The fermented dairy product of claim 1, wherein the texturizing *Lactococcus lactis* subsp. *lactis* lactic acid bacterium strain comprises:
   (a) a nucleotide sequence encoding a polypeptide having polymerase activity, wherein the polypeptide has at least 95% sequence identity with the amino acid sequence encoded by the nucleotide sequence of SEQ ID NO:9 ("wzy");
   (b) a nucleotide sequence encoding a polypeptide having polysaccharide transporter activity, wherein the polypeptide has at least 95% sequence identity with the amino acid sequence encoded by the nucleotide sequence of SEQ ID NO:12 ("wzx");
   (c) a nucleotide sequence encoding a polypeptide having glycosyltransferase (GT) activity, wherein the polypeptide has at least 95% sequence identity with the amino acid sequence encoded by the nucleotide sequence of SEQ ID NO:8 ("GT1");
   (d) a nucleotide sequence encoding a polypeptide having glycosyltransferase (GT) activity, wherein the polypeptide has at least 95% sequence identity with the amino acid sequence encoded by the nucleotide sequence of SEQ ID NO:10 ("GT2"); and
   (e) a nucleotide sequence encoding a polypeptide having glycosyltransferase (GT) activity, wherein the polypeptide has at least 95% sequence identity with the amino acid sequence encoded by the nucleotide sequence of SEQ ID NO:11 ("GT3").

5. The fermented dairy product of claim 4, wherein the texturizing *Lactococcus lactis* subsp. *lactis* lactic acid bacterium strain comprises:
   (a) the nucleotide sequence of SEQ ID NO:9 ("wzy");
   (b) the nucleotide sequence of SEQ ID NO:12 ("wzx");
   (c) the nucleotide sequence of SEQ ID NO:8 ("GT1");

(d) the nucleotide sequence of SEQ ID NO:10 ("GT2"); and (e) the nucleotide sequence of SEQ ID NO:11 ("GT3").

6. The fermented dairy product of claim 1, wherein the texturizing *Lactococcus lactis* subsp. *lactis* lactic acid bacterium strain is selected from the group consisting of the strain deposited with Deutsche Sammlung von Mikroorganismen and Zellkulturen GmbH, under Accession No. DSM 29291 and strains derived therefrom, wherein the strains derived therefrom have the same or improved texturizing capabilities in a dairy product as the lactic acid bacterium strain deposited under Accession No. DSM 29291.

7. The fermented dairy product of claim 1, wherein the texturizing *Lactococcus lactis* subsp. *lactis* lactic acid bacterium strain is the lactic acid bacterium strain deposited under Accession No. DSM 29291.

8. The fermented dairy product of claim 1, wherein the milk substrate is fermented with at least $1\times10^6$ CFU/ml of the texturizing lactic acid bacterium strain.

9. The fermented dairy product of claim 1, wherein the milk substrate is fermented with at least $1\times10^8$ CFU/ml of the texturizing lactic acid bacterium strain.

10. The fermented dairy product of claim 1, wherein the fermented dairy product is a cheese.

11. The fermented dairy product of claim 1, wherein the dairy product is a mesophilic dairy product.

12. The fermented dairy product of claim 11, wherein the mesophilic dairy product is selected from buttermilk, sour milk, cultured milk, smetana, sour cream, kefir, and fresh cheese.

13. A fermented dairy product comprising a texturizing *Lactococcus lactis* subsp. *lactis* lactic acid bacterium strain comprising an active eps gene cluster capable of producing exopolysaccharide (EPS), wherein the eps gene cluster comprises one or more nucleotide sequences selected from:
  (a) a nucleotide sequence encoding a polypeptide having polymerase activity, wherein the polypeptide has at least 95% sequence identity with the amino acid sequence encoded by the nucleotide sequence of SEQ ID NO:9 ("wzy");
  (b) a nucleotide sequence encoding a polypeptide having polysaccharide transporter activity, wherein the polypeptide has at least 95% sequence identity with the amino acid sequence encoded by the nucleotide sequence of SEQ ID NO:12 ("wzx"); and
  (c) at least one nucleotide sequence encoding a polypeptide having glycosyltransferase (GT) activity selected from:
    (i) a polypeptide having at least 95% sequence identity with the amino acid sequence encoded by the nucleotide sequence of SEQ ID NO:8 ("GT1");
    (ii) a polypeptide having at least 95% sequence identity with the amino acid sequence encoded by the nucleotide sequence of SEQ ID NO:10 ("GT2"); and
    (iii) a polypeptide having at least 95% sequence identity with the amino acid sequence encoded by the nucleotide sequence of SEQ ID NO:11 ("GT3"),
  wherein said fermented dairy product has improved texture as compared to a fermented dairy product without said texturizing *Lactococcus lactis* subsp. *lactis* lactic acid bacterium strain.

14. The fermented dairy product of claim 13, wherein the texturizing *Lactococcus lactis* subsp. *lactis* lactic acid bacterium strain generates fermented milk having a shear stress greater than 40 Pa when measured at shear rate 300 s$^{-1}$ when tested under the following conditions:

providing 200 ml semi-fat milk (1.5% fat) enriched with 2 g skim milk powder, heating the milk to 90° C. for 20 minutes, followed by cooling to an inoculation temperature of 30° C., inoculating with 2 ml of an overnight culture of the texturizing strain, maintaining the milk at inoculation temperature until pH 4.55 is reached, followed by storage at 4° C. for 5 days, followed by gently stirring and measuring the shear stress at shear rate 300 s$^{-1}$.

15. The fermented dairy product of claim 13, wherein the texturizing *Lactococcus lactis* subsp. *lactis* lactic acid bacterium strain comprises:
  (a) a nucleotide sequence encoding a polypeptide having polymerase activity, wherein the polypeptide has at least 95% sequence identity with the amino acid sequence encoded by the nucleotide sequence of SEQ ID NO:9 ("wzy");
  (b) a nucleotide sequence encoding a polypeptide having polysaccharide transporter activity, wherein the polypeptide has at least 95% sequence identity with the amino acid sequence encoded by the nucleotide sequence of SEQ ID NO:12 ("wzx");
  (c) a nucleotide sequence encoding a polypeptide having glycosyltransferase (GT) activity, wherein the polypeptide has at least 95% sequence identity with the amino acid sequence encoded by the nucleotide sequence of SEQ ID NO:8 ("GT1");
  (d) a nucleotide sequence encoding a polypeptide having glycosyltransferase (GT) activity, wherein the polypeptide has at least 95% sequence identity with the amino acid sequence encoded by the nucleotide sequence of SEQ ID NO:10 ("GT2"); and
  (e) a nucleotide sequence encoding a polypeptide having glycosyltransferase (GT) activity, wherein the polypeptide has at least 95% sequence identity with the amino acid sequence encoded by the nucleotide sequence of SEQ ID NO:11 ("GT3").

16. The fermented dairy product of claim 15, wherein the texturizing *Lactococcus lactis* subsp. *lactis* lactic acid bacterium strain comprises:
  (a) the nucleotide sequence of SEQ ID NO:9 ("wzy");
  (b) the nucleotide sequence of SEQ ID NO:12 ("wzx");
  (c) the nucleotide sequence of SEQ ID NO:8 ("GT1");
  (d) the nucleotide sequence of SEQ ID NO:10 ("GT2"); and
  (e) the nucleotide sequence of SEQ ID NO:11 ("GT3").

17. The dairy product of claim 13, wherein the texturizing *Lactococcus lactis* subsp. *lactis* lactic acid bacterium strain is selected from the group consisting of the strain deposited with Deutsche Sammlung von Mikroorganismen and Zellkulturen GmbH, under Accession No. DSM 29291 and strains derived therefrom, wherein the strains derived therefrom have the same or improved texturizing capabilities in a dairy product as the lactic acid bacterium strain deposited under Accession No. DSM 29291.

18. The fermented dairy product of claim 13, wherein the texturizing *Lactococcus lactis* subsp. *lactis* lactic acid bacterium strain is the lactic acid bacterium strain deposited under Accession No. DSM 29291.

19. The fermented dairy product of claim 13, wherein the dairy product is a cheese.

20. The fermented dairy product of claim 13, wherein the dairy product is a mesophilic dairy product.

21. The fermented dairy product of claim 20, wherein the mesophilic dairy product is selected from buttermilk, sour milk, cultured milk, smetana, sour cream, kefir, and fresh cheese.

* * * * *